US006979447B2

(12) United States Patent
Jameson et al.

(10) Patent No.: US 6,979,447 B2
(45) Date of Patent: Dec. 27, 2005

(54) IMMUNOMODULATION AND EFFECT ON CELL PROCESSES RELATING TO SEROTONIN FAMILY RECEPTORS

(75) Inventors: Bradford A. Jameson, Philadelphia, PA (US); Anna A. Tretiakova, Philadelphia, PA (US); Ross Albert, Philadelphia, PA (US); Harold Carter Davidson, Philadelphia, PA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 88 days.

(21) Appl. No.: 10/112,261

(22) Filed: Mar. 29, 2002

(65) Prior Publication Data

US 2003/0100570 A1 May 29, 2003

Related U.S. Application Data

(60) Provisional application No. 60/353,883, filed on Jan. 31, 2002, provisional application No. 60/345,295, filed on Oct. 25, 2001, and provisional application No. 60/280,296, filed on Mar. 30, 2001.

(51) Int. Cl.$^7$ .................. A61K 39/00; G01N 33/574
(52) U.S. Cl. ............... 424/184.1; 435/7.23; 435/7.24
(58) Field of Search ................. 424/184.1; 435/7.23, 435/7.24

(56) References Cited

U.S. PATENT DOCUMENTS

| | | | |
|---|---|---|---|
| 5,104,858 A | 4/1992 | Hait et al. | |
| 5,190,931 A | 3/1993 | Inouye | |
| 5,658,955 A | 8/1997 | Hitzig | |
| 5,703,088 A | 12/1997 | Sharpe et al. | |
| 6,004,490 A | 12/1999 | Tsai | |
| 2004/0029860 A1 | 2/2004 | Gil-Ad et al. | |
| 2004/0072824 A1 | 4/2004 | Telerman et al. | |
| 2004/0132719 A1 | 7/2004 | Finer et al. | |
| 2005/0013853 A1 | 1/2005 | Gil-Ad et al. | |

FOREIGN PATENT DOCUMENTS

| | | |
|---|---|---|
| WO | 92/04014 | 3/1992 |
| WO | WO 92/07065 | 4/1992 |
| WO | WO 99/43319 | 9/1999 |

OTHER PUBLICATIONS

Stryer et al, in Biochemistry, Third edition, W H Freeman Company, New York, pp. 31–33, 1998.*
Ngo et al, 1994, The Protein Folding Problem and Tertiary Structure Prediction, pp. 492–495.*
Attwood et al, The Babel of Bioinformatics, 2000, Science vol. 290 No. 5491: 471–473.*
Skolnick et al, From genes to protein structure and function: novel applications of computational approaches in the genomic era, Jan., 2000, TIBTECH 18: 34–39.*
Serafeim et al, Blood 99(7): 2545–2553, Apr. 1, 2002.*
Oksenberg et al, Nature 360(6400): 161–3, Nov. 1992.*
Alberati–Giani et al., 1998, Amino Acids 14:251–255.
Ameisen et al., 1989, J. Immunol. 142:3171–3179.
Aune et al., 1990, J. Immunol. 145:1826–1831.
Aune et al., 1993, J. Immunol. 151:1175–1183.
Aune et al., 1994, J. Immunol. 153:489–498.
Balaian et al., 2000, Eur. J. Immunol. 30:938–943.
Barnes et al., 1999, NeuroPharm. 38:1083–1152.
Boess et al., 1994, Neuropharmacology 33:275–317.
Breeveld, 2000, Lancet 355:735–740.
Bromley et al., 2001, Ann. Rev. Immunol. 19:375–396.
Colcher et al., 1998, Q. J. Nucl. Med. 42:225–241.
Coligan et al., 1999, In: Current Protocols in Immunology, Section 3.1.3–3.1.5.
Coligan et al., 1999, Current Protocols in Immunology, Section 14.1.3–14.1.6.
Cowen, 1991, British J. Psych., 159:7–14.
De Vivo et al., 1986, J. Pharmacol. Exp. Ther. 238:248–252.
Diehl et al., 2000, J. Molec. Med. 78:363–366.
Dutton et al., 1998, Ann. Rev. Immunol. 16:201–223.
Ensminger et al., 2000, Transplantation 69:2609–2612.
Foon et al., 1976, J. Immunol. 117:1545–1552.
Forbes et al., 1993, J. Med. Chem. 36:1104–1107.
Forbes et al., 1996, J. Med. Chem. 39:4966–4977.
Freundlich et al., 1997, Meth. Enzymol. 283:159–173.
Frumento et al., 2001, Transplant. Proc. 33:428–430.
Gershon et al., 1975, J. Exp. Med. 142:732–747.
Graca et al., 2000, J. Immunol. 165: 4783–4786.
Hampel et al., 1989, Biochemistry 28:4929–4933.
Hasselhoff et al., 1988, Nature 334:585–591.
Hillegass et al., 1999, Am. Heart J. 138:S24–S32.
Honey et al., 1999, J. Immunol. 163: 4805–4810.
Kenyon et al., 1999, Proc. Natl. Acad. Sci. USA. 96:8132–8136.
Khan et al., 1986, Int. Arch. Allergy Appl. Immunol. 81:378–380.
Khan et al., 2001, Science 292:1681–1686.
Kinney et al., 2002, Am. J. Public Health 92:24–26.
Kirk et al., 1999, Nature Medicine 5:686–693.
Kohm et al., 2000, Immunology Today 21:539–542.

(Continued)

*Primary Examiner*—Christina Chan
*Assistant Examiner*—Phuong Huynh
(74) *Attorney, Agent, or Firm*—Drinker, Riddle & Reath, LLP

(57) ABSTRACT

The present invention relates to the discovery that signaling via a serotonin type 1B, 2, 4 and 6 receptor is important in T cell activation such that inhibiting such signaling can be used to modulate the immune response. This immunomodulation is useful for the treatment of immune diseases or conditions, and for the development of potential therapeutics for such diseases or conditions. It has been further discovered that, in cells proceeding through the cell cycle process, inhibition of serotonin signaling inhibits the process and induces apoptosis and morphological changes to a cell. These effects of inhibiting serotonergic signaling can be useful for effecting selective cell killing and for identifying compounds that inhibit the signaling.

9 Claims, 33 Drawing Sheets

OTHER PUBLICATIONS

Kut et al., 1992, Immunopharmacol. Immunotoxicol. 14:783–796.
Laberge et al. 1996, J. Immunol. 156:310–315.
Lucki, 1992, Neurosci. & Biobehav. Rev., 16:83–93.
Marazziti et al. 2001, Neuropsychobiology 43:123–126.
Markees et al., 1998, J. Clin. Invest. 101: 2446–2452.
Mellor et al., 2001, Nature Immunol. 2:64–68.
Meyniel et al., 1997, Immunol. Lett. 55:151–160.
Mossner et al., 1998, Brain, Behavior, and Immunity 12:249–271.
Munn et al. 1998, Science 281:1191–1193.
Munn et al., 1999, J. Exp. Med. 189:1363–1373.
Pan et al., 2000, Transpl. Immunol. 8:189–194.
Price et al., 1997, Naunyn–Schmiedeberg's Arch. Pharmacol. 356:312–320.
Pulendran et al. 1999, Proc. Natl. Acad. Sci. USA 96:1036–1041.
Roszman et al., 1984, Soc. Neurosci. 10:726.
Ruat et al., 1993, Biochem. Biophys. Res. Commun. 193:268–276.
Ruat et al., 1993, Proc. Natl. Acad. Sci. USA 90:8547–8551.
Saha et al., 2001, Neuroimmunomodulation 9:23–33.
Santambrogio et al., 1993, J. Neuroimmunol. 45:113–120.
Siegel et al. 1998, Proc. Natl. Acad. Sci. USA 95:162–166.
Slauson et al., 1984, Cell. Immunol. 84:240–252.
Stefulj et al., 2000, Brain, Behavior, and Immunity 14:219–224.
Tretiakova et al., 2000, Nature Biotechnology 18:984–988.
Weintraub, 1990, Scientific American 262:40–46.
Widner et al., 2000, Immunol. Today 20:469–473.
Wills–Karp, 1999, Annu. Rev. Immunol. 17:255–281.
Young et al., 1993, Immunology 80:395–400.
Schleuning et al., 1994, "Inhibition of cyclosporine A/FK 506 resistant, lymphokine–induced T–cell activation by phenothiazine derivatives", Naunyn–Schmiedeberg's Arch. Pharmacol., 350:100–103.
Travis et al. 1998, British Journal of Psychiatry, 173:236–241.

* cited by examiner

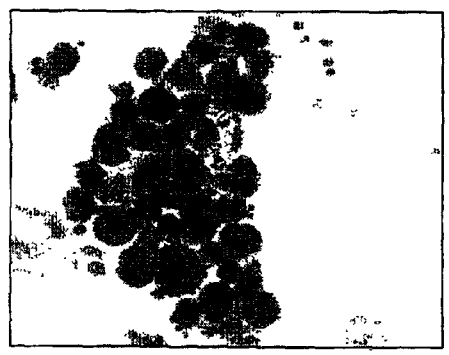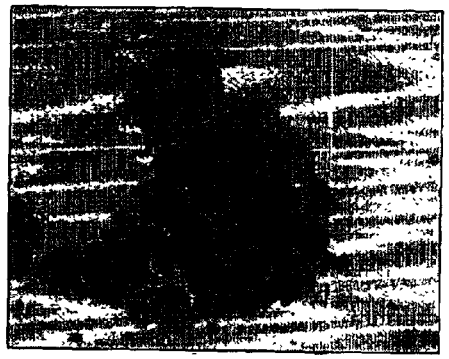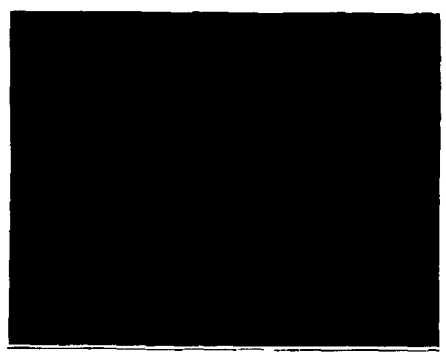
FIG.28

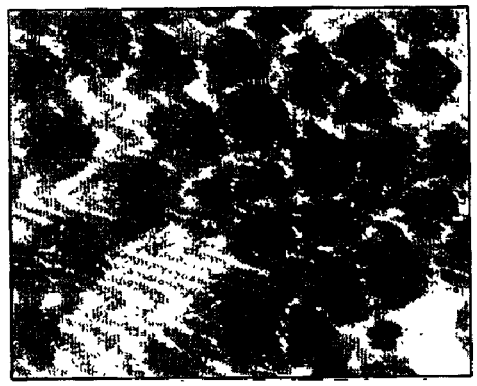
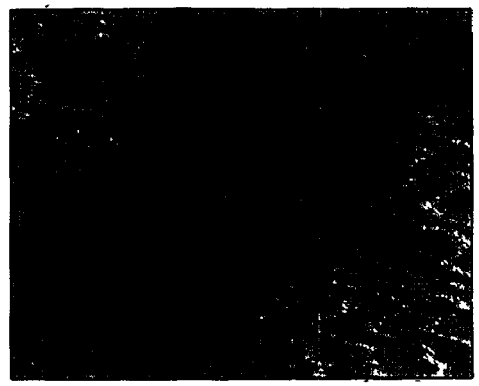
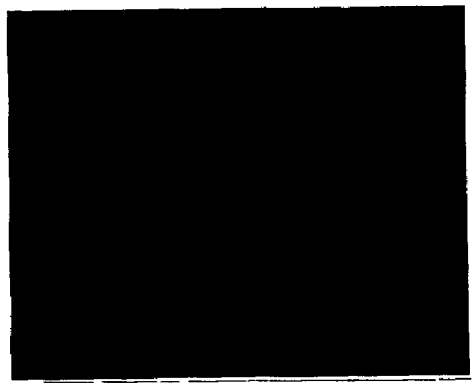
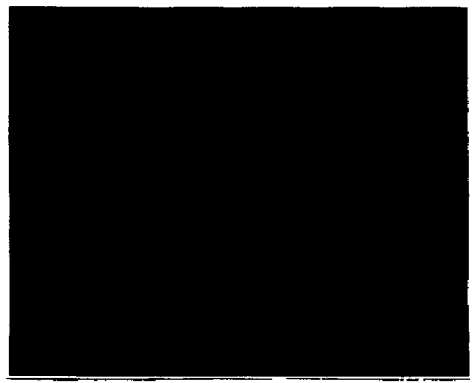
FIG.29

IMMUNOMODULATION AND EFFECT ON CELL PROCESSES RELATING TO SEROTONIN FAMILY RECEPTORS

CROSS-REFERENCE TO RELATED APPLICATIONS

The present application is entitled to priority under 35 U.S.C. §119(e), to U.S. Provisional Application No. 60/353,883, filed on Jan. 31, 2002, U.S. Provisional Application No. 60/345,295, filed on Oct. 25, 2001, and U.S. Provisional Application No. 60/280,296, filed on Mar. 30, 2001, all of which are hereby incorporated by reference in their entirety herein.

STATEMENT REGARDING FEDERALLY SUPPORTED RESEARCH OR DEVELOPMENT

This research was supported in part by U.S. Government funds (RO1 NS37726), and the U.S. Government may therefore have certain rights in the invention.

BACKGROUND OF THE INVENTION

Serotonin (also referred to as 5-hydroxytryptamine or 5-HT) is a neurotransmitter that has been strongly implicated in the pathophysiology and treatment of a wide variety of neuropsychiatric disorders. Serotonin exerts its effects through a diverse family of serotonin receptor molecules (referred to herein as "5-HT receptors" or "5-HTRs"). Classically, members of the serotonin receptor family have been grouped into seven (7) subtypes pharmacologically, i.e., according to their specificity of various serotonin antagonists. Thus, while all the 5-HT receptors specifically bind with serotonin, they are pharmacologically distinct and are encoded by separate genes. To date, fourteen (14) mammalian serotonin receptors have been identified and sequenced. More particularly, these fourteen separate 5-HT receptors have been grouped into seven (7) pharmacological subtypes, designated 5-HT1, 5-HT2, 5-HT3, 5-HT4, 5-HT5, 5-HT6, and 5-HT7. Several of the subtypes are further subdivided such that the receptors are grouped pharmacologically as follows: 5-HT1A, 5-HT1B, 5-HT1D, 5-HT1E, 5-HT1F, 5-HT2A, 5-HT2B, 5-HT2C, 5-HT3A, 5-HT3B, 5-HT4, 5-HT5A, 5-HT6, 5HT7. However, when the nucleic and amino acid sequences of the receptors are compared, the percent identity among the subtypes is not correlated to the pharmacological groupings.

Of the fourteen different mammalian serotonin receptors that have been cloned, all but one are members of the G-protein coupled receptor superfamily; that is, they are generally coupled to different second messenger pathways linked through guanine-nucleotide regulatory (G) proteins. For instance, serotonin receptors 5-HT1A, 5-HT1B, and 5-HT1D, inhibit adenylate cyclase, and 5-HT2 receptors activate phospholipase C pathways, stimulating breakdown of polyphosphoinositides. The 5-HT2 receptor belongs to the family of rhodopsin-like signal transducers that are distinguished by their seven-transmembrane configuration and their functional linkage to G-proteins.

The subtypes of serotonin receptors have been historically distinguished on the basis of their pharmacological binding profiles, on second messenger coupling, and based on physiological roles known for the better characterized serotonin receptors. Most of the data in the field used to characterize 5-HT receptors is not based on the properties of a single purified receptor protein or gene, but rather based on experimental observations using a model tissue.

As stated previously elsewhere herein, fourteen separate serotonin receptors have been identified encompassing seven subtypes based on, inter alia, structural homology, second messenger system activation, and drug affinity for certain ligands. Molecular cloning has indicated that 5-HT receptors belong to at least two protein superfamilies: G-protein-associated receptors that have seven putative transmembrane domains (TMDs) (5-HT1A, 1B, 1D, 1E, 5-HT2) and ligand-gated ion channel receptors that have four putative TMDs (5-HT3). The 5-HT2 subfamily is further divided into three classes: 5-HT2A, 5-HT2B, and 5-HT2C. 5HT2A and 5-HT2C receptor antagonists are thought to be useful in treating depression, anxiety, psychosis, and eating disorders. 5-HT2A and 5-HT2C receptors share about 51% amino acid homology overall and approximately 80% homology in the transmembrane domains. Studies of the 5-HT2A receptor in recombinant mammalian cell lines revealed that the receptor possessed two affinity states, high and low.

Both the 5-HT2A and 5-HT2C receptors are coupled to phospholipase C and mediate responses through the phosphatidylinositol pathway. Studies with agonists and antagonists display a wide range of receptor responses suggesting that there is a wide diversity of regulatory mechanisms governing receptor activity. The 5-HT2A and 5-HT2C receptors have also been implicated as the site of action of hallucinogenic drugs.

In the central nervous system (CNS), serotonin is thought to be involved in learning and memory, sleep, thermoregulation, motor activity, pain, sexual and aggressive behaviors, appetite, neuroendocrine regulation, and biological rhythms. Serotonin has also been linked to pathophysiological conditions such as anxiety, depression, obsessive-compulsive disorders, schizophrenia, suicide, autism, migraine, emesis, alcoholism and neurodegenerative disorders.

Serotonin regulates a wide variety of sensory, motor and behavioral functions in the mammalian CNS. This biogenic amine neurotransmitter is synthesized by neurons of the brain stem that project throughout the CNS, with highest density in basal ganglia and limbic structures (Steinbusch, 1984, In: Handbook of Chemical Neuroanatomy 3:68–125, Bjorklund et al., Eds., Elsevier Science Publishers, B.V.). Serotonergic transmission is thought to be involved with a variety of behaviors and psychiatric disorders including anxiety, sleep regulation, aggression, feeding and depression (Cowen, 1991, British J. Psych., 159:7–14; and Lucki, 1992, Neurosci. & Biobehav. Rev., 16:83–93). Understanding how 5-HT mediates its diverse physiological actions requires the identification and isolation of the pertinent 5-HT receptors.

Recently, studies have suggested that serotonin may play a role in the immune system since data demonstrate that serotonin receptors are present on various cells of the immune system. The "mind/body" problem has fascinated people of disparate disciplines for centuries. It has always been understood that there is a link between severe emotions or stress and the immune system. Serotonin is a widely disseminated neurotransmitter and known to play a major role in mood disorders and depression. Its role in modulating the immune response, however, has not been appreciated, much less understood.

It has long been known that the survival of a fetus in utero is an immunological paradox. The fetus, in theory, should undergo allograft rejection by the mother. In most cases, the fetus in not rejected, thus the paradox. Understanding how the maternal immune system selectively suppresses the allograft rejection with regard to the fetus while leaving all of the other immune responses intact has been "the holy grail" of immunology. If one understood the process and could reproduce it therapeutically, it would open a fundamentally new door for potential treatments for autoimmune diseases as well as remarkable new methods for treating the rejection symptoms that accompany transplantation procedures. However, until the present invention, the need for improved therapeutics for autoimmune disease and allograft rejection has been unmet. The present invention meets these needs.

In 1998, Munn et al. (1998, Science 281:1191–1193) solved a major piece of the puzzle. This research group showed that the "rapid T cell-induced rejection of all allogeneic concepti occurred when pregnant mice were treated with a pharmracologic inhibitor of indoleamine 2,3-dioxygenase (IDO), a tryptophan-catabolizing enzyme expressed by trophoblasts and macrophages. Thus, by catabolizing tryptophan, the mammalian conceptus suppresses T cell activity and defends itself against rejection." In other words, shortly after a female becomes pregnant she produces an enzyme (IDO) that sends tryptophan on the first step of the metabolic pathway towards the production of niacin. This obviously implies that tryptophan must, somehow, play a key role in mounting and maintaining an immune response and/or that producing kynurenine (the first step of the niacin pathway) has a suppressive effect. Although it has become clear that the induction of IDO will inhibit T cell proliferation and may play a role in allograft acceptance (Alberati-Giani et al., 1998, Amino Acids 14:251–255; Munn et al., 1999, J. Exp. Med. 189:1362–1373; Widner et al., 2000, Immunol. Today 20:469–473; Pan et al., 2000, Transpl. Immunol. 8:189–194; Mellor et al., 2001, Nature Immunol. 2:64–68), it was absolutely unclear why tryptophan catabolism inhibits the immune responses.

Tryptophan is one of the ten essential amino acids required for building new proteins in the cell. It is possible, though not likely, that the catabolism of tryptophan results in starvation and, therefore, accounts for the observed T cell inhibition. However, none of the other nine essential amino acids have been implicated in the control of T cell responses. Nevertheless, there is a strong correlation between the local depletion of tryptophan levels and inhibition of T cell function (Munn et al., 1999, J. Exp. Med. 189:1362–1373; Widner et al., 2000, Immunol. Today 20:469–473; Frumento et al., 2001, Transplant. Proc. 33:428–430).

Tryptophan is the only known source for producing 5-hydroxytryptamine (also known as serotonin). If the modulation of local tryptophan levels were to be related to the observed modulation in T cell reactivity via the serotonergic pathway, then, obviously, serotonin must play a central role in T cell activation. However, although serotonin is one of the most widely studied biologically active molecules in the history of biochemistry, its role in the T cell activation pathway has not been identified or exploited until the present invention.

There have been reports in the literature about the immunomodulatory effects of adding serotonin exogenously to mitogenically stimulated lymphocyte cultures. Under some circumstances, serotonin has been shown to stimulate the activated T cells (Foon et al., 1976, J. Immunol. 117:1545–1552; Kut et al., 1992, Immunopharmacol. Immunotoxicol. 14:783–796; Young et al., 1993, Immunology 80:395–400), whereas most laboratories report that high concentrations of added serotonin inhibit the proliferation (Slauson et al., 1984, Cell. Immunol. 84:240–252; Khan et al., 1986, Int. Arch. Allergy Appl. Immunol. 81:378–380; Mossner & Lesch, 1998, Brain, Behavior, and Immunity 12:249–271). Thus, the prior art is, at best, unclear as to what role, if any, serotonin might play in modulating the immune response.

Over the intervening years, it has been shown that of the fourteen known pharmacologically distinct serotonin receptors, lymphocytes express type 2a, type 2b, type 2c, type 6 and type 7 on resting cells (Ameisen et al., 1989, J. Immunol. 142:3171–3179; Stefulj et al., 2000, Brain, Behavior, and Immunity 14:219–224) and that the type 1a and type 3 receptors are up-regulated upon activation (Aune et al., 1993, J. Immunol. 151:1175–1183; Meyniel et al., 1997, Immunol. Lett. 55:151–160; Stefulj et al., 2000, Brain, Behavior, and Immunity 14:219–224). Although the functional role of these receptors on lymphocytes has never been clearly defined, it is generally known that the serotonin receptors, except for the type 3 receptors which are cation channels, are 7 transmembrane domain, G-coupled receptors (for a review see Barnes and Sharp, 1999, NeuroPharm. 38:1083–1152). More specifically, the type 1 receptors act on adenylate cyclase, resulting in a down-regulation of cAMP (De Vivo & Maayani, 1986, J. Pharmacol. Exp. Ther. 238:248–252). Forskolin, for example, is a pharmacological agonist of adenylate cyclase and an up-regulator of cAMP, and, therefore, an inhibitor of T cell activation. Forskolin inhibition of T cells, on-the-other-hand, can be rescued by the addition of serotonin (Aune et al., 1990, J. Immunol. 145:1826–1831; Aune et al., 1993, J. Immunol. 151:1175–1183).

In contrast to the type 1a receptors, the type 6 and type 7 receptors, present on resting T cells, act by up-regulating cAMP in response to serotonin (Ruat et al., 1993, Biochem. Biophys. Res. Commun. 193:268–276; Ruat et al., 1993, Proc. Natl. Acad. Sci. USA 90:8547–8551). It is almost a counterintuitive arrangement, the type 6 and 7 receptors present on the resting cells should act to slow the T cell response, whereas the type 1a should counteract the signals sent from the 6 and 7 receptors. The type 2a and 2c receptors couple positively to phospholipase C and lead to increased accumulation of inositol phosphates and intracellular $Ca^{2+}$, thereby turning on the Protein Kinase C signal transduction cascade (for a review see Boess and Martin, 1994, Neuropharmacology 33:275–317).

With regard to the functional control of the immune response, Gershon et al. (1975, J. Exp. Med. 142:732–738), hypothesized that serotonin was required for mounting a T cell-mediated delayed-type hypersensitivity (DTH) response in mice. However, the authors of this study attributed the dependence of the DTH response on serotonin to the vasoactive properties of this biogenic amine.

A series of studies from the Miles Research Center in West Haven, Conn., showed the presence and involvement of the 5-HT 1a receptors in human and murine T cells (Aune et al., 1990, J. Immunol. 145:1826–1831; Aune et al., 1993, J. Immunol. 151:1175–1183; Aune et al., 1994, J. Immunol. 153:1826–1831). These studies established that IL-2-stimulated human T cell proliferation could be inhibited by a blockade of tryptophan hydroxylase, i.e., the first enzyme involved in the conversion of tryptophan to serotonin, and that the inhibition could be reversed by the addition of 5-hydroxy tryptophan, i.e., the metabolic product of the inhibited enzyme. Furthermore, they could block human T cell proliferation in vitro with a 5-HT 1a-specific receptor antagonist. In a murine model, they demonstrated that a type 1a receptor antagonist, but not a type 2 receptor antagonist, was able to inhibit the in vivo contact sensitivity response, but not antibody responses, to oxazalone.

Using both type 1a and type 2 receptor antagonist, Laberge et al. (1996, J. Immunol. 156:310–315) serotonin could induce the chemotactic factor, IL-16, from CD8+ T cells and that this activity could be specifically inhibited by the addition of type 2 receptor inhibitors, but not antagonists of the 1a receptor. Thus, although the prior art indicated that serotonin plays a role in the immune system, it was not clear what that role was and there was nothing to suggest that the immune system could be modulated by use of receptor antagonists.

There are a handful of references suggesting that serotonin may play a role the immune response. In 1989, a prominent immunologist, Philip Askenase, and his colleagues demonstrated that a 5-HTR2 antagonist could inhibit a delayed-type hypersensitivity (DTH) response in mice (Amiesen et al., 1989, J. Immunol. 142:3171 –3179). Amiesen et al., reasoned that "late-acting DTH effector T cells might express functional 5-HT2R and that these receptors might require in vivo activation in order for the T cells to locally produce the inflammatory lymphokine-dependent aspects of DTH." These data were subsequently orphaned presumably because rodent mast cells contain serotonin but human mast cells do not, such that the results were not applicable to a human immune response. Later, Aune et al. (1994, J. Immunol. 153:489–498), demonstrated that a 5-HTR1a antagonist could inhibit a murine DTH response in vivo and showed that inhibition of the enzyme tryptophan hydroxylase (the first enzyme involved in the conversion of tryptophan to serotonin) could inhibit T cell proliferation. Again, these authors provided important pieces of information, but failed to recognize the larger role of serotonin in the mounting of a T cell-dependent response.

The first evidence that macrophages and lymphocytes expressed receptors capable of responding to serotonin was presented in 1984 (Roszman et al., 1984, Soc. Neurosci. 10:726). Over the intervening years, it has been shown that of the fourteen known pharmacologically distinct serotonin receptors, resting lymphocytes express 5-HT2A, 2B, 2C, 6, and 7 (Ameisen et al., 1989, J. Immunol. 142:3171–3179; Stefulj et al., 2000, Brain, Behavior, and Immunity 14:219–224) and that the 5-HT1A and 5-HT3 receptors are up-regulated upon activation (Aune et al., 1993, J. Immunol. 151:1175–1183; Meyniel et al., 1997, Immunol. Lett. 55:151–160; Stefulj et al., 2000, Brain, Behavior, and Immunity 14:219–224).

Although the functional role of serotonin receptors on lymphocytes and in immune regulation if any has never been defined, it is generally known that serotonin receptors, with the exception of type 3 receptors which are cation channels, are G-coupled receptors comprising seven transmembrane domains (for a review see Barnes and Sharp, 1999, NeuroPharm. 38:1083–1152). More specifically, the type 1 receptors act on adenylate cyclase, resulting in a down-regulation of cAMP (De Vivo & Maayani, 1986, J. Pharmacol. Exp. Ther. 238:248–252).

In contrast to the 5-HT1A receptors, the 5-HT6 and 5-HT7 receptors, present on resting T cells, act by up-regulating cAMP in response to serotonin (Ruat et al., 1993, Biochem. Biophys. Res. Commun. 193:268–276; Ruat et al., 1993, Proc. Natl. Acad. Sci. USA 90:8547–8551). In an apparently counterintuitive arrangement, the 5-HT6 and 5-HT7 receptors present on the resting cells should act to slow the T cell response, whereas the type 1a should counteract the signals sent from the 5-HT6 and 5-HT7 receptors. The 5-HT2A and 5-HT2C receptors couple positively to phospholipase C and lead to increased accumulation of inositol phosphates and intracellular $Ca^{2+}$, thereby turning on the protein kinase C signal transduction cascade (for a review see Boess and Martin, 1994, Neuropharmacology 33:275–317).

It was previously hypothesized that serotonin was required for mounting a T cell-mediated delayed-type hypersensitivity (DTH) response in mice (Gershon et al., 1975, J. Exp. Med. 142:732–738). It was concluded that dependence of the DTH response on serotonin was due to the vasoactive properties of this biogenic amine. There have been mixed reports in the literature about the immunomodulatory effects of serotonin. Under some circumstances, exogenous 5-HT has been shown to stimulate activated T cells (Foon et al., 1976, J. Immunol. 117:1545–1552; Kut et al., 1992, Immunopharmacol. Immunotoxicol. 14:783–796; Young et al., 1993, Immunology 80:395–400), whereas most laboratories report that high concentrations of exogenous 5-HT inhibit proliferation of activated T cells (Slauson et al., 1984, Cell. Immunol. 84:240–252; Khan et al., 1986, Int. Arch. Allergy Appl. Immunol. 81:378–380; Mossner & Lesch, 1998, Brain, Behavior, and Immunity 12:249–271). Thus, it is not clear what effect if any serotonin may have on the immune system, since studies suggest that this neurotransmitter both up- and down-regulates the immune response.

There exists a long-felt need to develop therapies for modulating the immune response, especially therapies that regulate certain aspects of the immune response while not affecting others. Thus, there is a great need to identify potential therapeutic targets for modulating the immune response. The present invention meets these needs.

BRIEF SUMMARY OF THE INVENTION

The invention includes a method of modulating an immune response in a mammal. The method comprises administering an effective amount of an inhibitor of the interaction of serotonin with a serotonin receptor to the mammal, thereby modulating the immune response in the mammal.

In one aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

In another aspect, the inhibitor is selected from the group consisting of a selective serotonin type 1B receptor antagonist, a selective serotonin type 2A receptor antagonist, a selective serotonin type 2B receptor antagonist, a selective serotonin type 2C receptor antagonist, a selective serotonin type 4 receptor antagonist, and a selective serotonin type 6 receptor antagonist.

In yet another aspect, the inhibitor is a serotonin receptor antagonist selected from the group consisting of risperidone, ketanserin, mianserin, LY 53857, SB 206553, SB 242084, MDL 11939, SB 216641, and methiothepin.

In one aspect, the inhibitor is an antibody that specifically binds with a serotonin receptor.

In another aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

In a further aspect, the mammal is a human.

The invention includes a method of inhibiting an immune response in a mammal. The method comprises administering an immune response inhibiting amount of an inhibitor of the interaction of serotonin with a serotonin receptor to a mammal, thereby inhibiting the immune response in the mammal.

In one aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

In another aspect, the inhibitor is selected from the group consisting of a selective serotonin type 1B receptor antagonist, a selective serotonin type 2A receptor antagonist, a selective serotonin type 2B receptor antagonist, a selective serotonin type 2C receptor antagonist, a selective serotonin type 4 receptor antagonist, and a selective serotonin type 6 receptor antagonist.

In yet another aspect, the inhibitor is a serotonin receptor antagonist selected from the group consisting of risperidone, ketanserin, mianserin, LY 53857, SB 206553, SB 242084, MDL 11939, SB 216641, and methiothepin.

In a further aspect, the serotonin receptor is a serotonin type 4 receptor, and further wherein the immune response is CD-8 dependent.

In yet a further aspect, the serotonin receptor is a serotonin type 6 receptor, and further wherein the immune response is CD-4 dependent or CD-8 dependent.

In one aspect, the inhibitor is an antibody that specifically binds with a serotonin receptor.

In another aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

In yet another aspect, the mammal is a human.

The invention includes a method of inhibiting an immune reaction by an immune cell. The method comprises inhibiting a serotonin signal transmitted by a serotonin receptor on the cell wherein inhibiting the signal inhibits activation of the cell and further wherein the inhibiting a serotonin signal comprises contacting the immune cell with an effective amount of an inhibitor of the interaction of serotonin with a serotonin receptor, thereby inhibiting the immune reaction by the cell.

In one aspect, the immune cell is selected from a T cell, and a B cell.

The invention also includes a method of modulating an immune response in a mammal having an autoimmune disease mediated by an immune cell activated by serotonin signaling. The method comprises administering to the mammal an effective amount of an inhibitor of the interaction of serotonin with a serotonin receptor, thereby modulating the immune response in the mammal.

In one aspect, the mammal is a human.

In another aspect, the serotonin receptor is selected from the group consisting of a serotonin type 1B receptor, a serotonin type 2A receptor, a serotonin type 2B receptor, and a serotonin type 2C receptor.

In yet another aspect, the inhibitor is selected from the group consisting of a selective serotonin type 1B receptor antagonist, a selective serotonin type 2A receptor antagonist, a selective serotonin type 2B receptor antagonist, and a selective serotonin type 2C receptor antagonist.

In a further aspect, the inhibitor is a serotonin receptor antagonist selected from the group consisting of risperidone, ketanserin, mianserin, LY 53857, SB 206553, SB 242084, and MDL 11939.

In yet a further aspect, the inhibitor is an antibody that specifically binds with a serotonin receptor. In another aspect, the serotonin receptor is selected from the group consisting of a serotonin type 1B receptor, a serotonin type 2A receptor, a serotonin type 2B receptor, and a serotonin type 2C receptor.

In another aspect, the autoimmune disease is selected from the group consisting of myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Gillian-Barre syndrome, vasculitis, multiple sclerosis, neuromyelitis optica (Devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome, and fibromyalgia.

In a further aspect, the modulation is inhibition.

The invention includes a method of inhibiting an immune response in a mammal wherein the immune response is mediated by activation of a serotonin receptor on a T cell. The method comprises contacting the T cell with an effective amount of an inhibitor of the interaction of serotonin with a serotonin receptor, thereby inhibiting the immune response in the mammal.

In one aspect, the method further comprising administering the inhibitor as a bolus injection.

In another aspect, the serotonin receptor is selected from the group consisting of a serotonin type 1B receptor, a serotonin type 2A receptor, a serotonin type 2B receptor, and a serotonin type 2C receptor.

In yet another aspect, the inhibitor is selected from the group consisting of a selective serotonin type 1B receptor antagonist, a selective serotonin type 2A receptor antagonist, a selective serotonin type 2B receptor antagonist, and a selective serotonin type 2C receptor antagonist.

In a further aspect, the inhibitor is a serotonin receptor antagonist selected from the group consisting of risperidone, ketanserin, mianserin, LY 53857, SB 206553, SB 242084, and MDL 11939.

In another aspect, the inhibitor is an antibody that specifically binds with a serotonin receptor.

In even another aspect, the mammal is a human.

The invention includes a method of inhibiting activation of an immune cell in a mammal wherein the activation is mediated by activation of a serotonin receptor on the immune cell. The method comprises administering an effective amount of an inhibitor of the interaction of serotonin with a serotonin receptor to the mammal, further wherein the immune cell is contacted with the inhibitor, thereby inhibiting activation of the immune cell.

In one aspect, the serotonin receptor is selected from the group consisting of a serotonin type 1B receptor, a serotonin type 2A receptor, a serotonin type 2B receptor, and a serotonin type 2C receptor.

In another aspect, the inhibitor is selected from the group consisting of a selective serotonin type 1B receptor antagonist, a selective serotonin type 2A receptor antagonist, a selective serotonin type 2B receptor antagonist, and a selective serotonin type 2C receptor antagonist.

In yet another aspect, the inhibitor is a serotonin receptor antagonist selected from the group consisting of risperidone, ketanserin, mianserin, LY 53857, SB 206553, SB 242084, and MDL 11939.

In a further aspect, the inhibitor is an antibody that specifically binds with a serotonin receptor.

In yet a further aspect, the mammal is a human.

The invention also includes a method of inhibiting a secondary immune response in a mammal. The method comprises administering to the mammal an effective amount of an inhibitor of the interaction of serotonin with a serotonin receptor, thereby inhibiting the secondary immune response in the mammal.

In one aspect, the serotonin receptor is selected from the group consisting of a serotonin type 1B receptor, a serotonin type 2A receptor, a serotonin type 2B receptor, and a serotonin type 2C receptor.

In another aspect, the inhibitor is selected from the group consisting of a selective serotonin type 1B receptor antagonist, a selective serotonin type 2A receptor antagonist, a selective serotonin type 2B receptor antagonist, and a selective serotonin type 2C receptor antagonist.

In yet another aspect, the inhibitor is a serotonin receptor antagonist selected from the group consisting of risperidone, ketanserin, mianserin, LY 53857, SB 206553, SB 242084, and MDL 11939.

In a further aspect, the inhibitor is an antibody that specifically binds with a serotonin receptor.

In yet a further aspect, the mammal is a human.

The invention includes a method of treating a disease mediated by a cell in a mammal wherein the cell requires transmission of a serotonin signal via a serotonin receptor. The method comprises inhibiting serotonin interaction with a serotonin receptor on the cell wherein the inhibition is deleterious to the cell such that the cell does not mediate the disease.

In one aspect, the inhibition of serotonin interaction is mediated by contacting a cell with an inhibitor of the interaction of serotonin with a serotonin receptor.

In another aspect, the serotonin receptor is a selected from the group consisting of a serotonin type 1 receptor, a serotonin type 2 receptor, a serotonin type 4 receptor, and a serotonin type 6 receptor.

In yet another aspect, the disease is selected from the group consisting of multiple myeloma, myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Gillian-Barre syndrome, vasculitis, multiple sclerosis, neuromyelitis optica (Devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome, and fibromyalgia.

In one aspect, the serotonin receptor is a serotonin type 1B receptor and further wherein the disease is multiple myeloma.

The invention includes a method of inducing apoptosis in a cell. The method comprises inhibiting transmission of a serotonin signal via a serotonin receptor on the cell wherein the inhibition induces apoptosis, and further wherein the inhibiting serotonin interaction with a serotonin receptor on the cell comprises contacting the cell with an effective amount of an inhibitor of the interaction of serotonin with a serotonin receptor, thereby inducing apoptosis in the cell.

The invention also includes a method of inducing cell death. The method comprises inhibiting transmission of a serotonin signal via a serotonin receptor on the cell wherein the inhibition induces death of the cell, further wherein the inhibition comprises contacting the cell with an effective amount of an inhibitor of the interaction of serotonin with the serotonin receptor, thereby inducing death of the cell.

The invention includes a method of identifying a compound useful for treating an autoimmune disease in a mammal. The method comprises contacting a serotonin receptor with a test compound and comparing the level of binding of serotonin with the serotonin receptor contacted with the compound with the level of serotonin binding with an otherwise identical serotonin receptor not contacted with the compound, wherein a lower level of serotonin binding with the serotonin receptor contacted with the compound compared with the level of serotonin binding with the otherwise identical serotonin receptor not contacted with the compound is an indication that the compound is useful for treating the autoimmune disease in the mammal. In one aspect, the mammal is a human.

The invention includes a compound identified by this method.

In one aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

The invention includes a method of identifying a compound useful for treating an allogeneic grafting response in a mammal. The method comprises contacting a serotonin receptor with a test compound and comparing the level of binding of serotonin with the serotonin receptor contacted with the compound with the level of serotonin binding with an otherwise identical serotonin receptor not contacted with the compound, wherein a lower level of serotonin binding with the serotonin receptor contacted with the compound compared with the level of serotonin binding with the otherwise identical serotonin receptor not contacted with the compound is an indication that the compound is useful for treating the allogeneic graft response in the mammal.

The invention includes a compound identified by this method.

In one aspect, the serotonin receptor is selected from the group consisting of a serotonin type 1B receptor, a serotonin type 2A receptor, a serotomin type 2B receptor, a serotonin type 2C receptor, a serotonin type 4 receptor, and a serotonin type 6 receptor.

In one aspect, the mammal is a human.

The invention includes a method of identifying a compound useful for inhibiting activation of a T cell wherein the activation is mediated by binding of serotonin with a serotonin receptor on the T cell. The method comprises contacting a T cell with a test compound and comparing the level of activation of the T cell contacted with the compound with the level of activation of an otherwise identical T cell not contacted with the compound, wherein a lower level of activation of the T cell contacted with the compound compared with the level of activation of the otherwise identical T cell not contacted with the compound is an indication that the compound is useful for inhibiting activation of a T cell wherein the activation is mediated by serotonin binding with a serotonin type 2 receptor on the T cell.

The invention also includes a method of identifying a compound that affects signaling via a serotonin receptor on a cell. The method comprises contacting a cell with a compound and assessing any change in cell morphology in the cell compared with the morphology of the cell prior to being contacted with the compound, wherein a change in the morphology of the cell contacted with the compound compared with the morphology of the cell prior to being contacted with the compound is an indication that the compound affects signaling via a serotonin receptor on the cell, thereby identifying a compound that affects signaling via a serotonin receptor on a cell.

The invention includes a compound identified by this method.

The invention includes a method of affecting a cell cycle process in a cell. The method comprises inhibiting transmission of a signal via a serotonin receptor on the cell, further wherein the inhibiting transmission of a signal via a serotonin receptor on the cell comprises contacting the cell with an effective amount of an inhibitor of the interaction of serotonin with a serotonin receptor, thereby affecting a cell cycle process.

The invention includes a method of affecting apoptosis in a cell expressing a serotonin receptor. The method comprises inhibiting a signal transmitted via the receptor further wherein the inhibiting comprises contacting the cell with an effective amount of an inhibitor of the interaction of serotonin with a serotonin receptor, thereby affecting apoptosis in the cell.

The invention includes a method of inducing apoptosis in a cell expressing a serotonin receptor, the method comprising inhibiting a signal transmitted via the receptor, thereby inducing apoptosis in the cell.

The invention includes a kit for modulating an immune response in a mammal. The kit comprises an effective amount of an inhibitor of the interaction of serotonin with a serotonin receptor. The kit further comprises an applicator and an instructional material for the use thereof.

In one aspect, the serotonin receptor is selected from the group consisting of a serotonin type 1B receptor, a serotonin type 2A receptor, a serotonin type 2B receptor, a serotonin type 2C receptor, a serotonin type 4 receptor, and a serotonin type 6 receptor.

In another aspect, the mammal is a human.

The invention includes a kit for affecting a cell cycle process in a cell expressing a serotonin receptor. The kit comprises an effective amount of an inhibitor of the interaction of serotonin with the serotonin receptor. The kit further comprises an applicator and an instructional material for the use thereof.

The invention includes a kit for inducing apoptosis in a cell expressing a serotonin receptor. The kit comprises an effective amount of an inhibitor of the interaction of serotonin with the serotonin receptor. The kit further comprises an applicator and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 5, comprising FIG. 5A depicts the effects at 0.1 $\mu$g/ml of ConA; FIG. 5B depicts the effects at 1 $\mu$g/ml of ConA, and FIG. 5C depicts the effects of 10 $\mu$g/ml of ConA. The dotted line in each of the panels refers to the baseline stimulation level of ConA without any added reagents.

2C antagonist; SB 242084: selective 5HT 2C antagonist; Methysergide: partial type 1 antagonist/type 2 antagonist; Methiothepin: general type 1, 2, 6 & 7 antagonist.

Figure 8A:
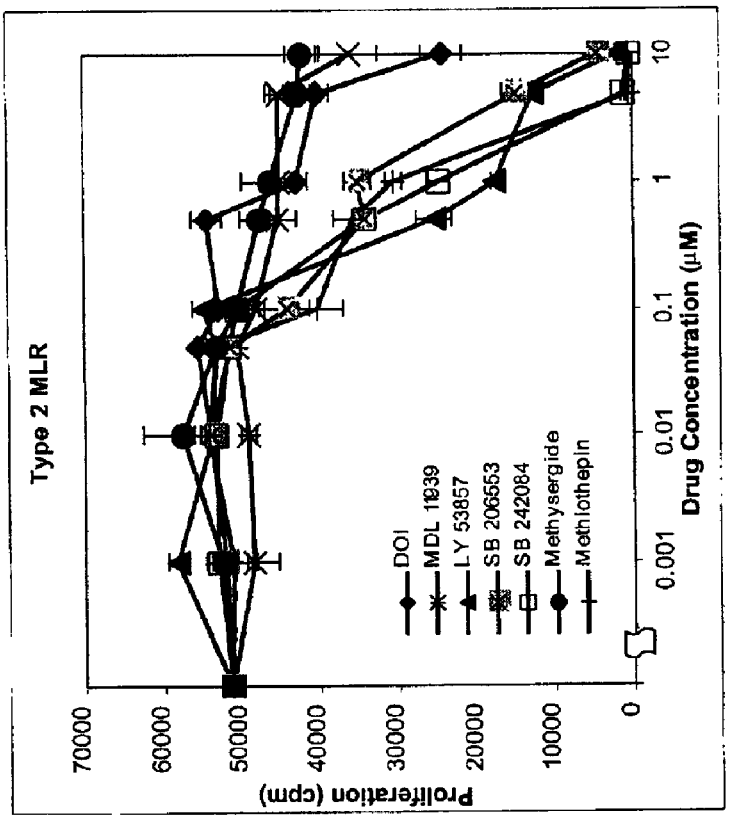
FIG. 8A is a diagram depicting the dose-response effects of titrating a panel of agonists and antagonists known to target the 5-HTR 2 receptors on the activation of ConA (5 $\mu$g/ml) stimulated human lymphocytes. The cells were harvested 72 hours after initiating ConA stimulation. The drugs used for this study have the following well-defined attributes: DOI: 5HT 2 agonist (prolonged exposure of the receptors to this compound results in their down-regulation); LY 53857: selective 5HT2A/2B/2C antagonist; MDL 11939: selective 5HT 2A antagonist; SB 206553: selective 5HT2B/
Figure 8B:
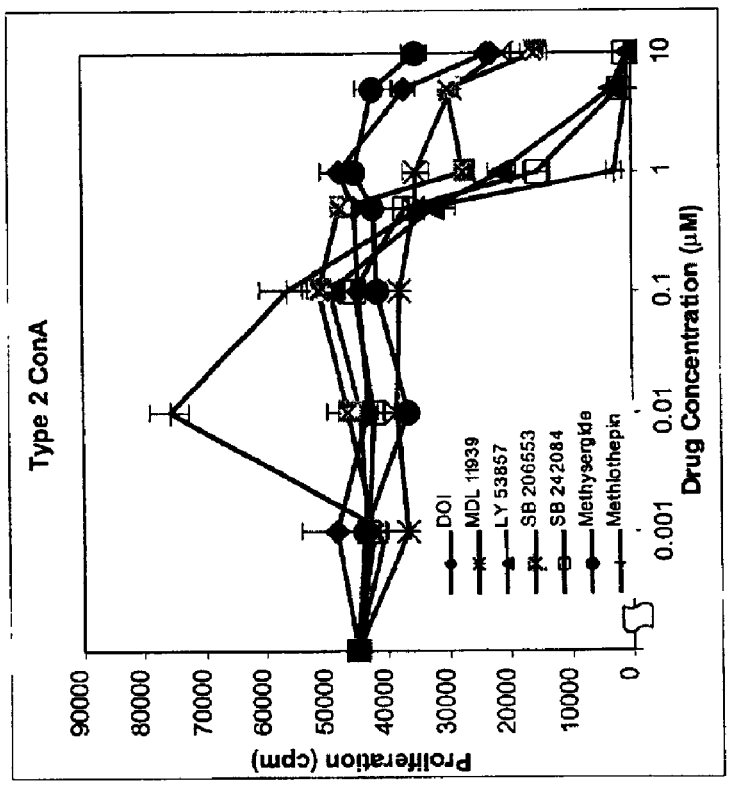

FIG. 8B is a diagram depicting the dose-response effects of titrating a panel of agonists and antagonists known to target the 5-HTR 2 receptors on the allogeneic stimulation of human lymphocytes (otherwise known as a mixed lymphocyte reaction). The cells were harvested 120 hours after the initiating stimulation. The drugs used for this study have the following well-defined attributes: DOI : 5HT 2 agonist (prolonged exposure of the receptors to this compound results in their down-regulation); LY 53857: selective 5HT2A/2B/2C antagonist; MDL 11939: selective 5HT 2A antagonist; SB 206553: selective 5HT2B/2C antagonist; SB 242084: selective 5HT 2C antagonist; Methysergide: partial type 1 antagonist/type 2 antagonist; Methiothepin: general type 1, 2, 6 and 7 antagonist.

Figure 9B:
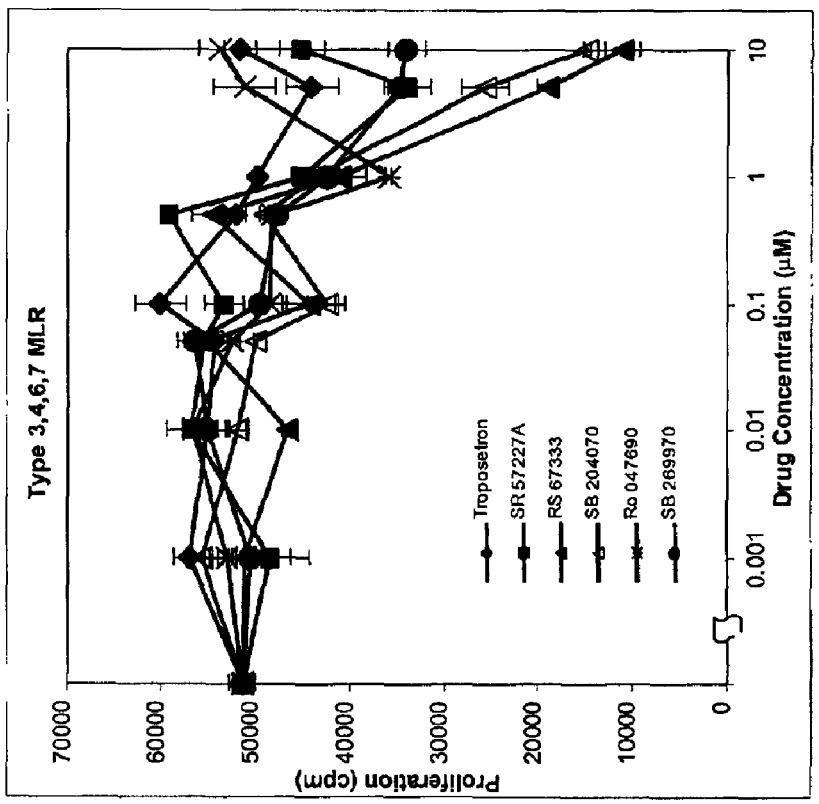
Figure 9A:
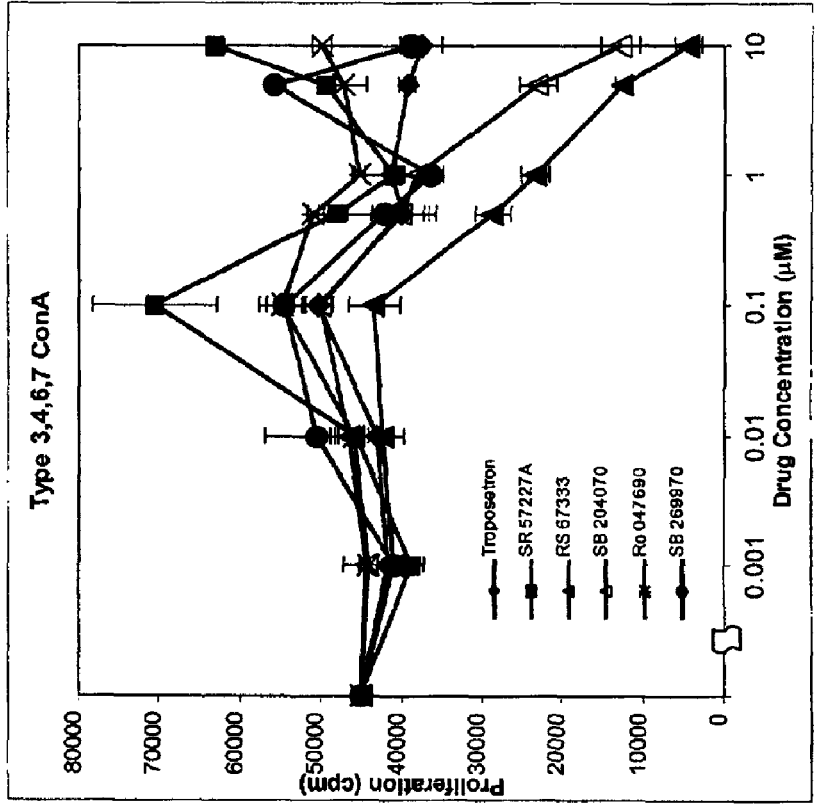

FIG. 9A is a diagram depicting the dose-response effects of titrating a panel of agonists and antagonists known to target either the 5-HTR 3, 4, 6 or 7 receptors on the activation of ConA (5 µg/ml) stimulated human lymphocytes. The cells were harvested 72 hours after initiating ConA stimulation. The drugs used for this study have the following well-defined attributes: SR 57222A: selective 5HT 3 agonist; Troposetron: selective 5HT 3 antagonist (clinically approved as an anti-emetic); RS 67333: selective 5HT4 agonist (down-regulates the receptors upon prolonged contact); SB 204070: selective 5HT 4 receptor antagonist; Ro 047690: selective 5HT 6 antagonist SB 269970: selective 5HT 7 antagonist.

FIG. 9B is a diagram depicting the dose-response effects of titrating a panel of agonists and antagonists known to target either the 5-HTR 3, 4, 6 or 7 receptors on the allogeneic stimulation of human lymphocytes (otherwise known as a mixed lymphocyte reaction). The cells were harvested 120 hours after the initiating stimulation. The drugs used for this study have the following well-defined attributes: SR 57222A: selective 5HT 3 agonist; Troposetron: selective 5HT 3 antagonist (clinically approved as an anti-emetic); RS 67333: selective 5HT4 agonist (down-regulates the receptors upon prolonged contact); SB 204070: selective 5HT 4 receptor antagonist; Ro 047690: selective 5HT 6 antagonist; SB 269970: selective 5HT 7 antagonist.

Figure 10:
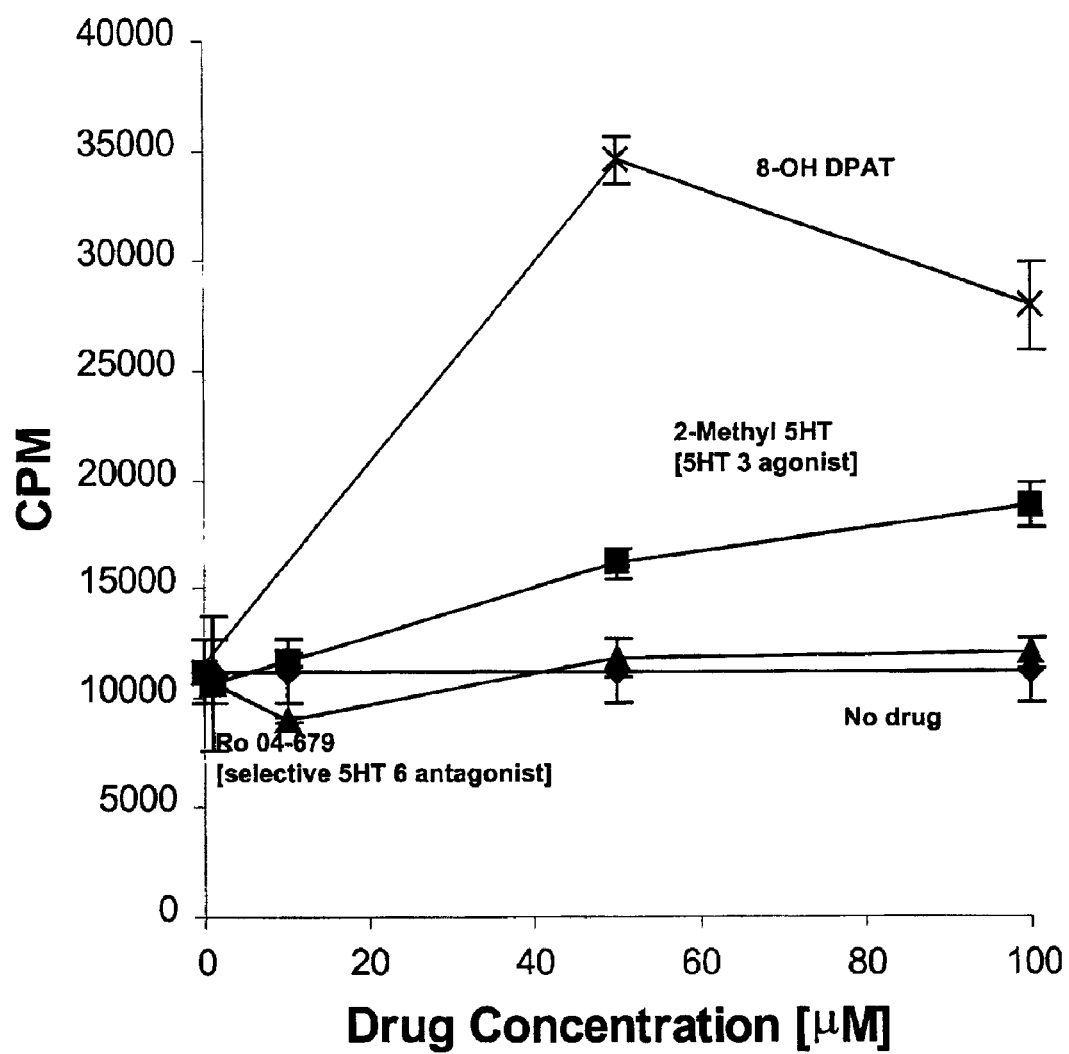

FIG. 10 is a graph depicting a murine mixed lymphocyte reaction assay (BALB/c vs. C57BL6) examining the effects of a 5HT3R agonist and a selective 5HT6R antagonist relative to the action of the 5HT1R agonist.

Figure 11:
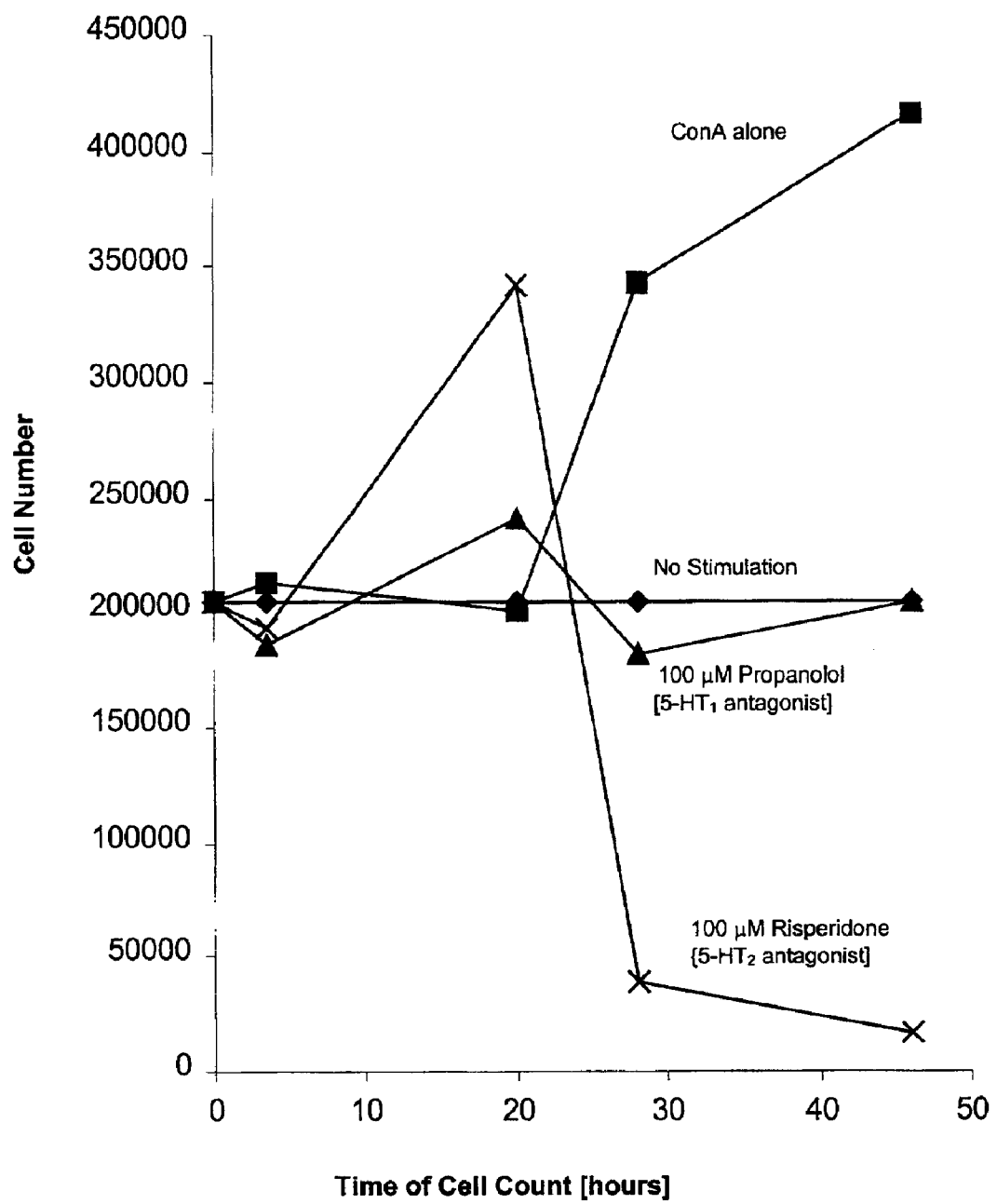

FIG. 11 is a diagram depicting the effect of a 5HT type 1 receptor antagonist and a 5HT type 2 receptor antagonist on the cell numbers occurring during the mitogenic stimulation of human lymphocyte activation. The cells were stimulated with 10 µg/ml ConA. The cells were repurified on a Ficoll gradient prior to addition of the inhibitor. Trypan blue exclusion was used to count the viable cells.

Figure 12A:
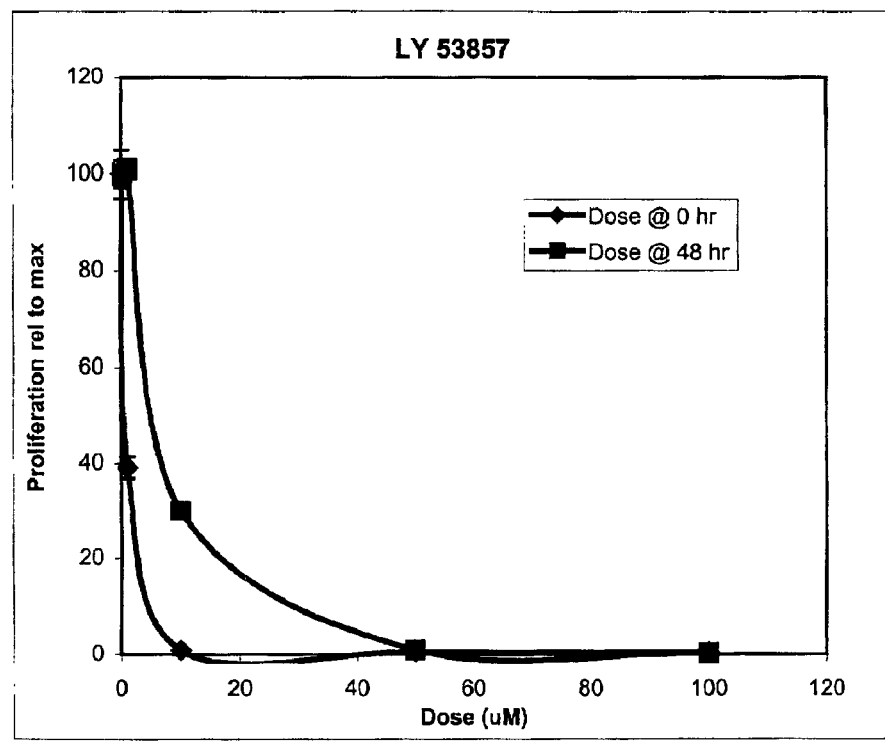

FIG. 12A is a diagram depicting the effects of a highly selective 5HT type 2 receptor antagonist, LY 53857, on the mitogenic stimulation of human lymphocytes (ConA stimulation at 1 µg/ml, and the cells were harvested at 72 hours). The results depict the effect of adding the inhibitor at time=0 or at 48 hours after the initiation of the assay.

Figure 12B:
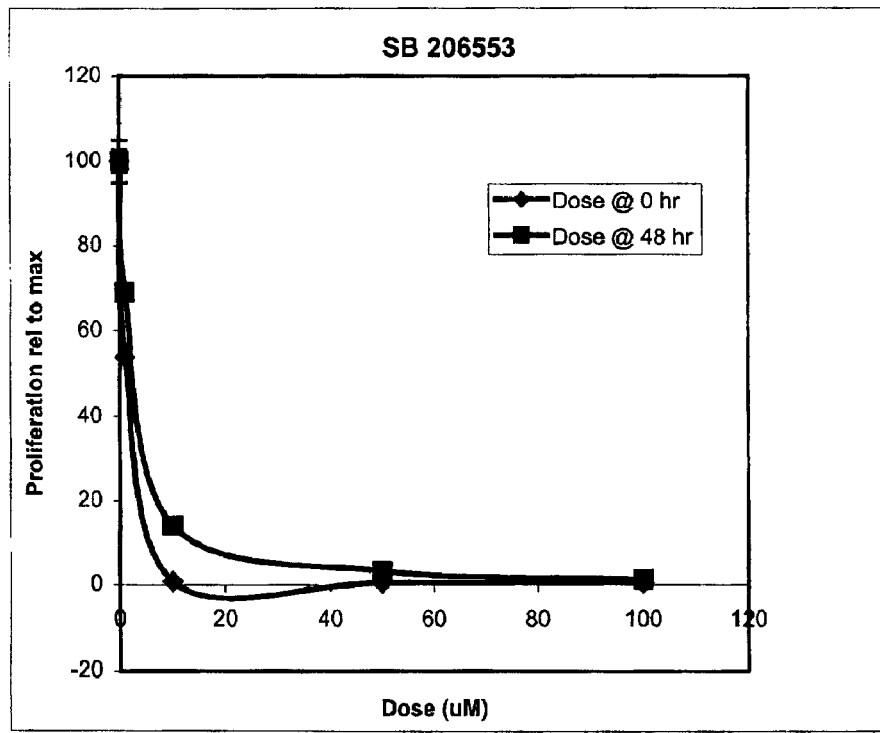

FIG. 12B is a diagram depicting the effects of a highly selective 5HT type 2 receptor antagonist, SB 206553, on the mitogenic stimulation of human lymphocytes (ConA stimulation at 1 µg/ml, and the cells were harvested at 72 hours). The diagram depicts the effect of adding the inhibitor at time=0 or at 48 hours after the initiation of the assay.

Figure 12C:
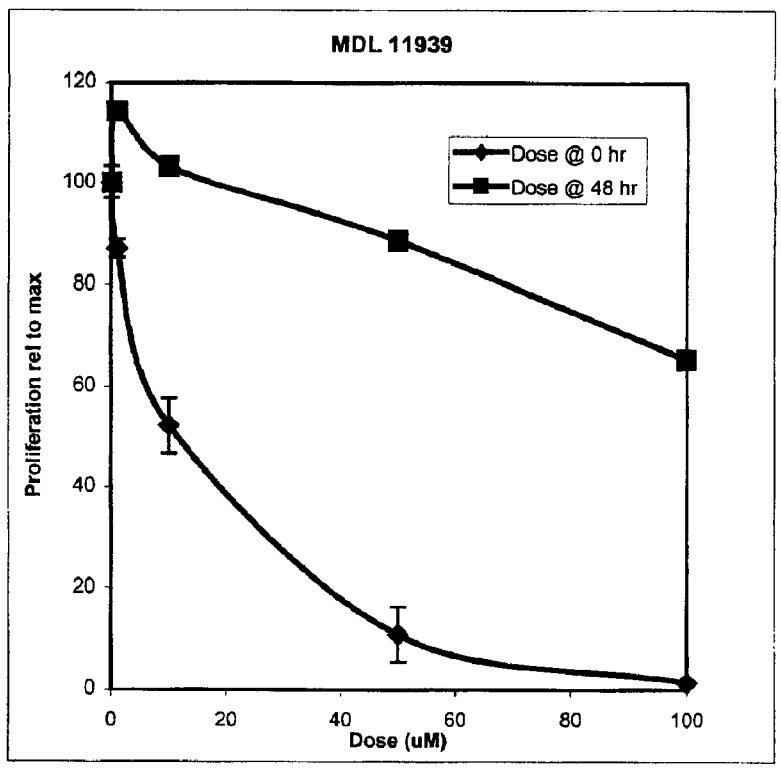

FIG. 12C is a diagram depicting the effects of a highly selective 5HT type 2 receptor antagonist, MDL 11939, on the mitogenic stimulation of human lymphocytes (ConA stimulation at 1 µg/ml, and the cells were harvested at 72 hours). The data depicted the effect of adding the inhibitor at time=0 or at 48 hours after the initiation of the assay.

Figure 12D:
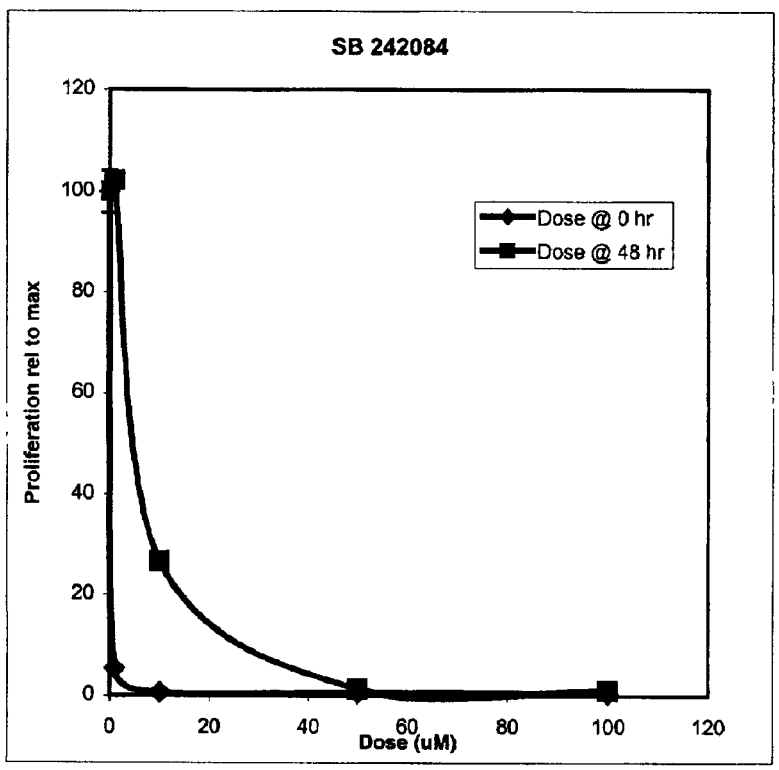

FIG. 12D is a diagram depicting the effects of a highly selective 5HT type 2 receptor antagonist, SB 242084, on the mitogenic stimulation of human lymphocytes (ConA stimulation at 1 µg/ml, and the cells were harvested at 72 hours). The diagram depicts the effect of adding the inhibitor at time=0 or at 48 hours after the initiation of the assay.

Figure 13:
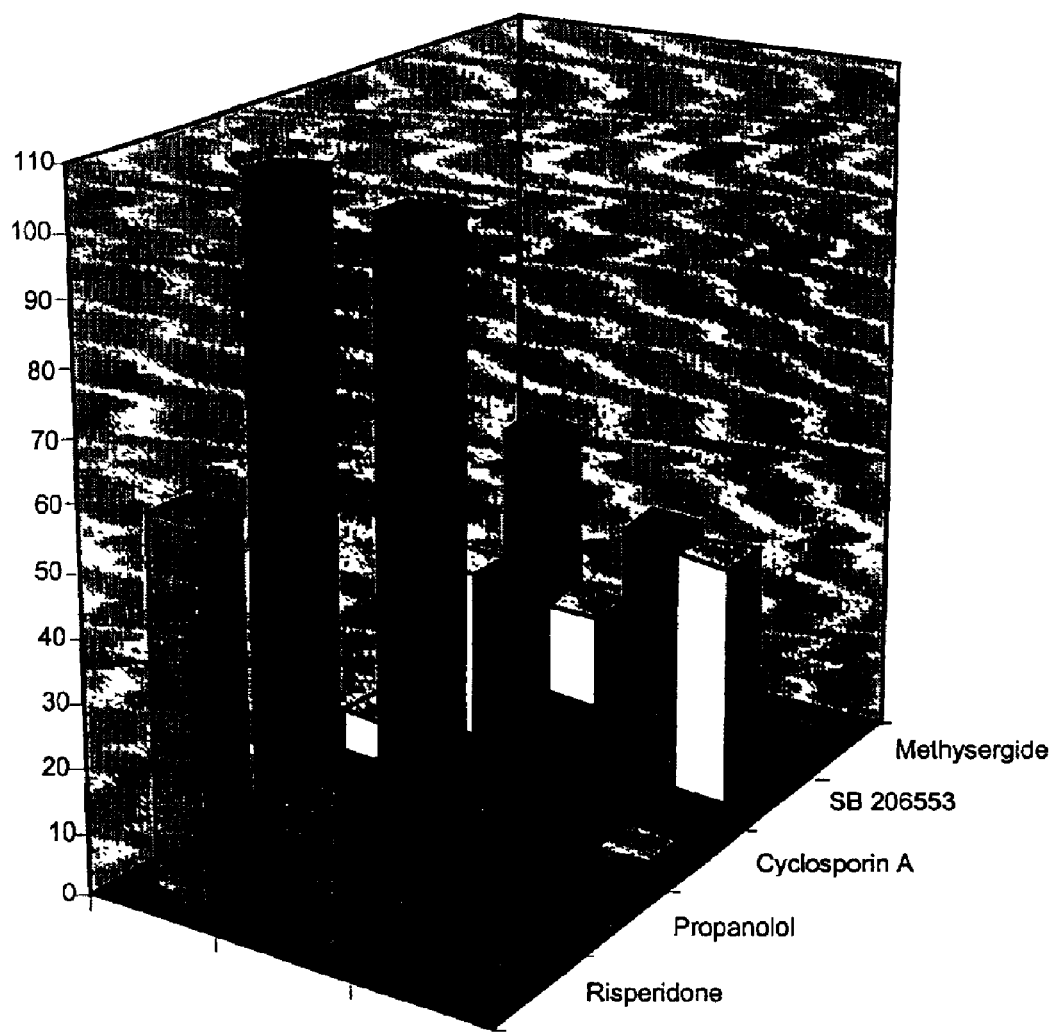

FIG. 13 is a graph depicting the results of a murine allograft model for studying the effects of serotonin receptor antagonists versus Cyclosporin A. The date disclosed herein are derived from a cytotoxic T cell killing assay using the splenocytes from the treated mice versus the p815 target cells.

Figure 14:
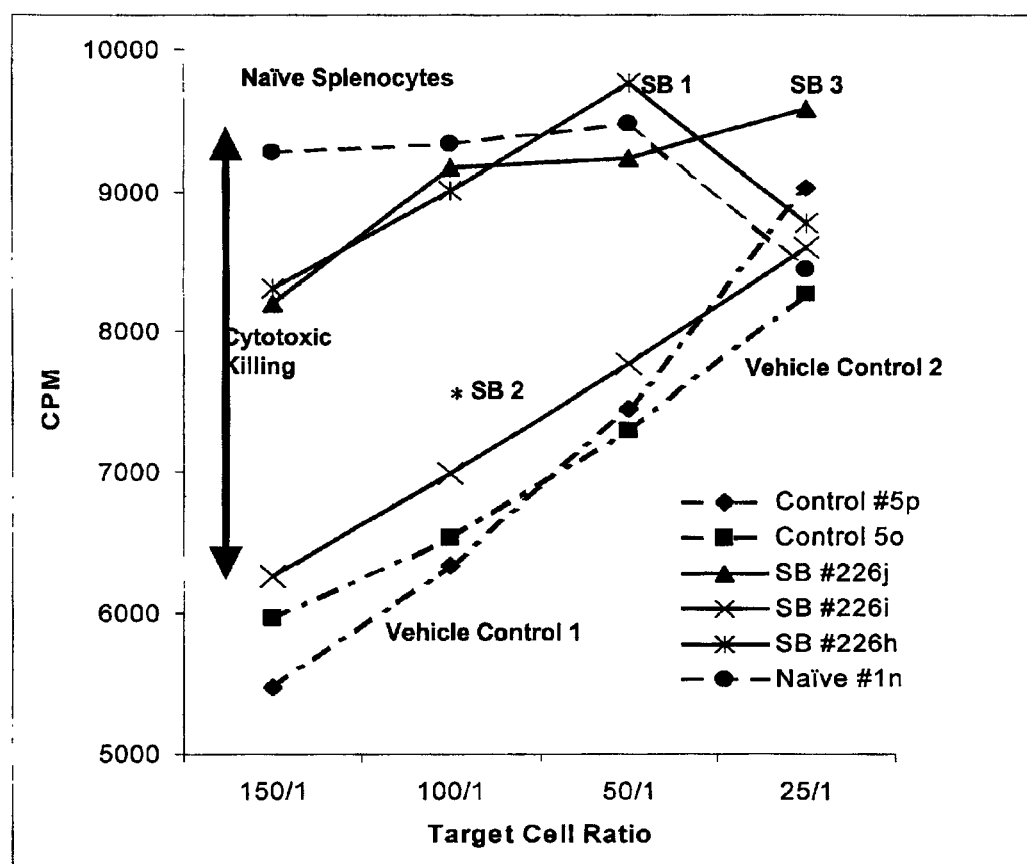

FIG. 14 is a diagram depicting the effects of the 5HT2R selective antagonist, SB 206553, in a murine allograft model. The three SB 206553-treated mice were designated SB#226h, SB#226i, and SB#226j. Two of the treated mice had the allogeneic response completely suppressed. Only one of the mice (SB#226j) demonstrated virtually no immunologic effect as a result of treatment. However, SB#226j required repeated tail vein injections in order to administer the drug. Even when injected with great care, the tail vein injection can be technically difficult, and does not always occur on the first attempt.

Figure 15:
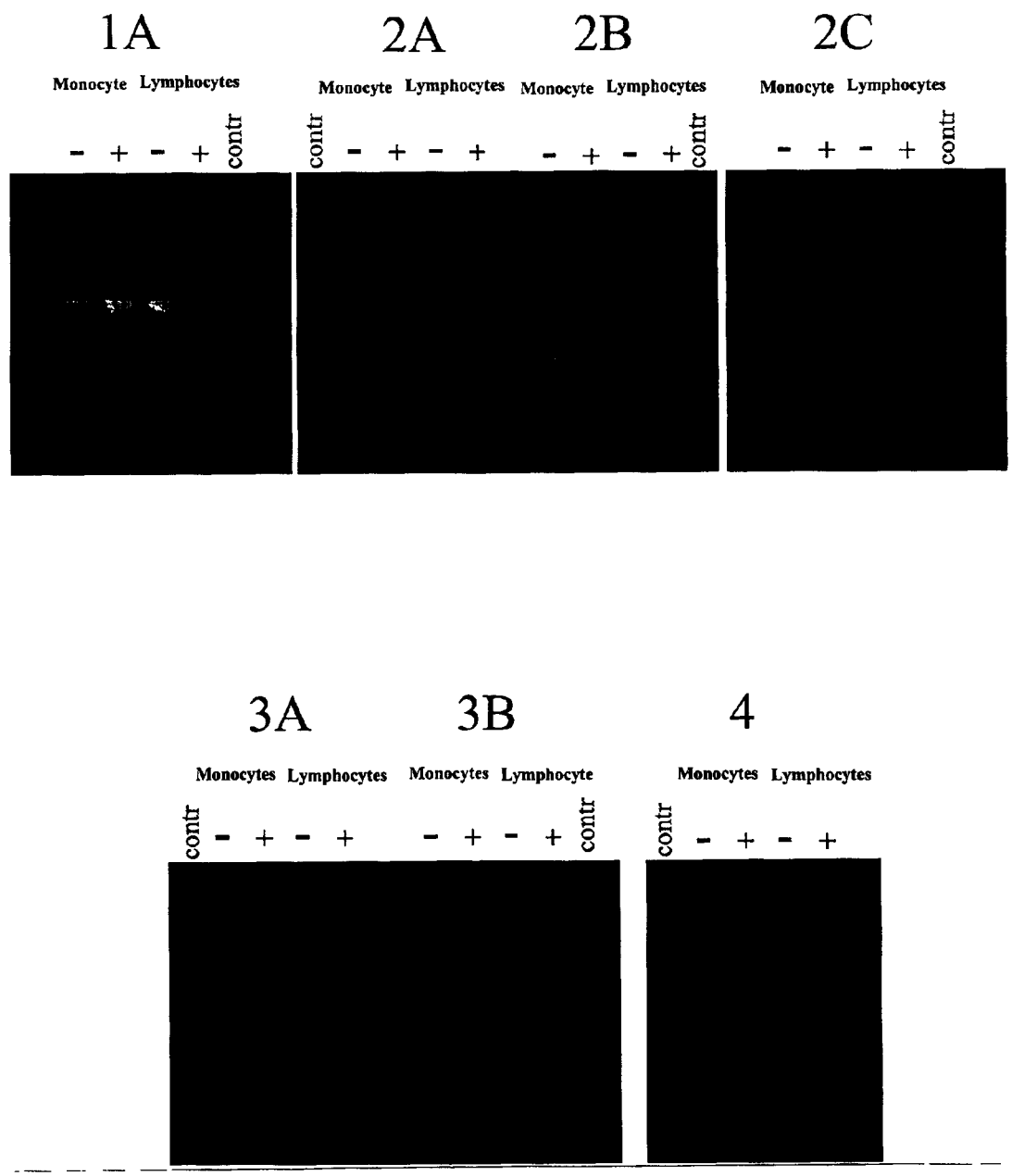

FIG. 15 is an image depicting a gel demonstrating RT PCR priming of resting and activated lymphocytes and monocytes. The (+) lanes indicate cells that were mitogenically stimulated for 48 hours with ConA prior to creating a cDNA library. The (−) lanes indicate resting cell.

Figure 16:
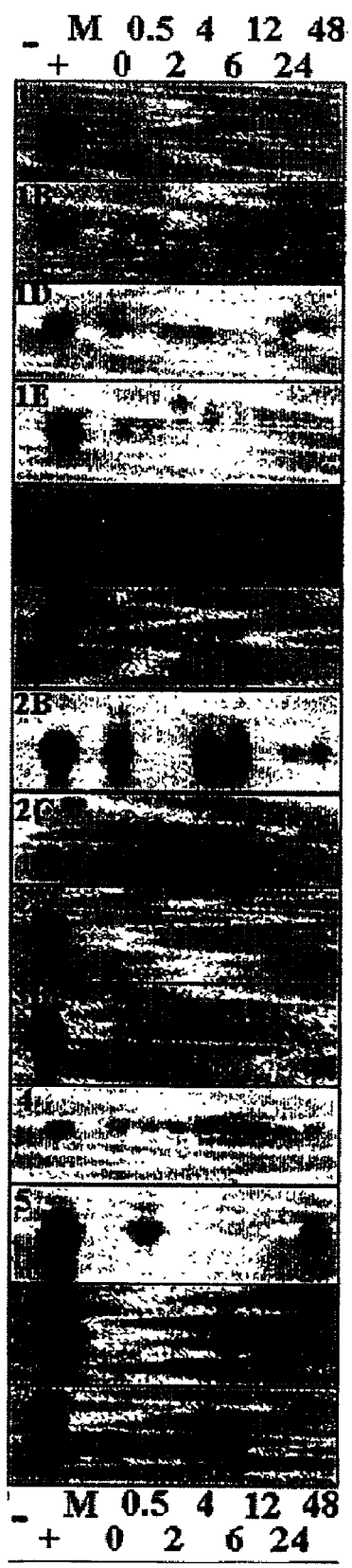

FIG. 16 is an image depicting a Southern blot demonstrating expression of each of the fourteen distinct serotonin receptors, wherein the blots were probed with an appropriate internal oligonucleotide as follows: 1A: ctgcagaacgtggccaat-tatcttattggctcttt (SEQ ID NO: 1); 1B: gtggagtactcagctaaaag-gactcccaagaggg (SEQ ID NO:2); 1D: ctctcttttcaaccacgt-gaaaatcaagcttgct (SEQ ID NO: 3);1E: atctagatcacccaggagaacgtcagcagatctcta (SEQ ID NO: 4);1F: gagcagcaaagacattataccacaagagacaagcaa (SEQ ID NO: 5);2A: tcggctcttttgtgtcattttcattccttaacca (SEQ ID NO: 6);2B: ctcaacgcctaacatggttgactgtgtctacagttt (SEQ ID NO: 7);2C: taactgacattttcaatacctccgatggtggacgct (SEQ ID NO: 8);3A: gggagttcagcatggaaagcagtaactactatgcag (SEQ ID NO: 9);3B: ttcaatctatcagcaactacctccaaactcaggacc (SEQ ID NO: 10);4: caccattcttttgtcaccaatattgtggatcctttc (SEQ ID NO: 11);5: cttttggctggggagagacgtactctgagg (SEQ ID NO:12);6: atcctcaacctctgcctcatcagcctggac (SEQ ID NO:13);7: tgaaag-gaaaaacatctccatctttaagcgagaaca (SEQ ID NO:14).

Figure 17:
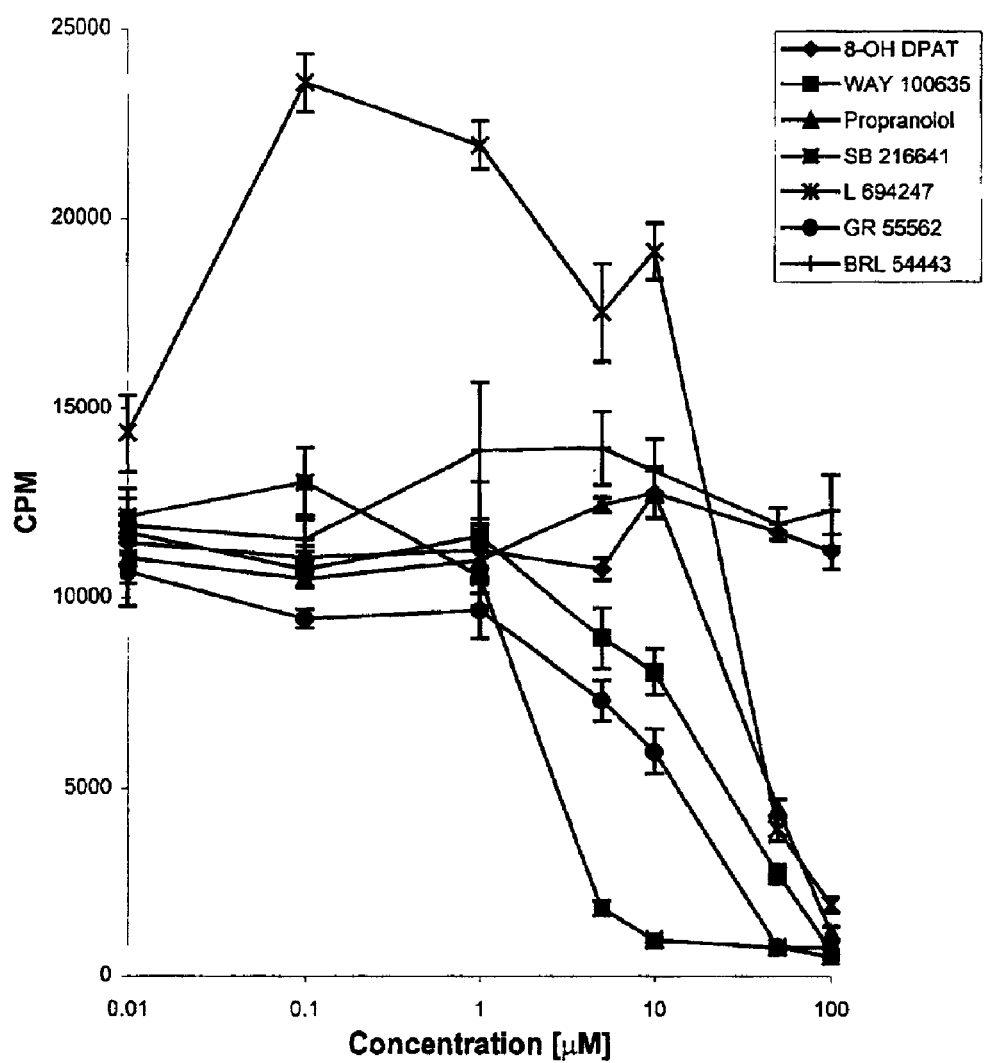

FIG. 17 is a graph depicting the functional behavior of various 5-HT Class 1 selective drugs. 8-OH DPAT is a 1A selective agonist; WAY 100635 is a selective 1A antagonist; propranolol is a general type 1 receptor antagonist (as well as a beta-adrenergic antagonist); SB 216641 is a selective 1B antagonist; L694247 is a selective 1B/1D agonist; GR 55562 is a selective 1B/1D antagonist; BRL 54443 is a selective 1E/1F agonist. The drugs were added at time=0 of a 5mg/ml ConA stimulation of human lymphocytes as described elsewhere herein.

Figure 18B:
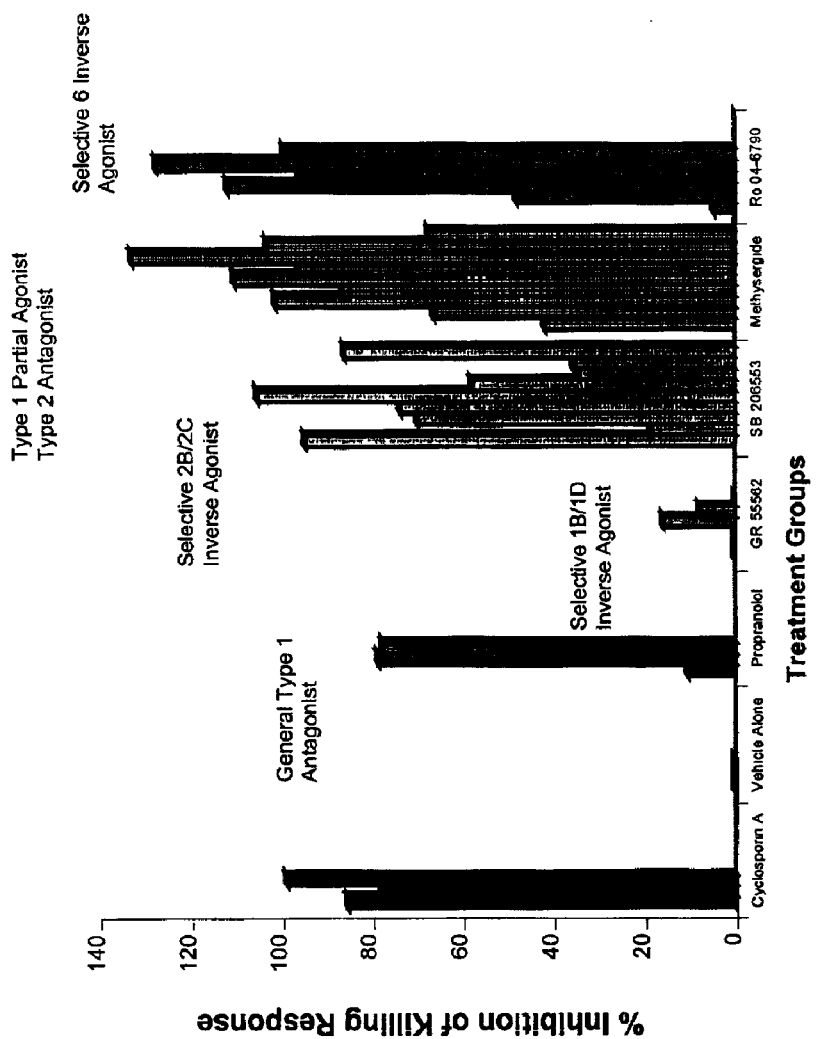
Figure 18A:
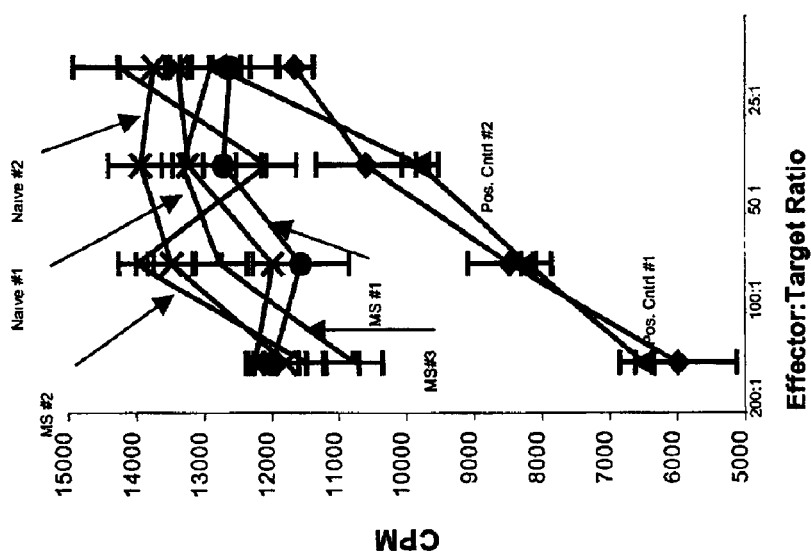

FIG. 18A is a graph depicting the data obtained using a murine allograft model described elsewhere herein. Briefly, the data depicted were obtained using a single representative study. The two positive controls shown indicate the observed the induced cytotoxic killing activity, whereas the naïve controls have never received the P815 cells and, consequently, provide a measure of the background of the assay. The Methysergide-treated (MS) mice demonstrate complete inhibition of the induced killing response.

FIG. 18B is a graph depicting data obtained using a murine allograft model as described elsewhere herein. The data depicted represents the pooled result of multiple assays, where the 100:1 effector:target ratio data was used to calculate the per cent inhibition. Each individual bar represents the data collected from a single mouse.

Figure 19B:
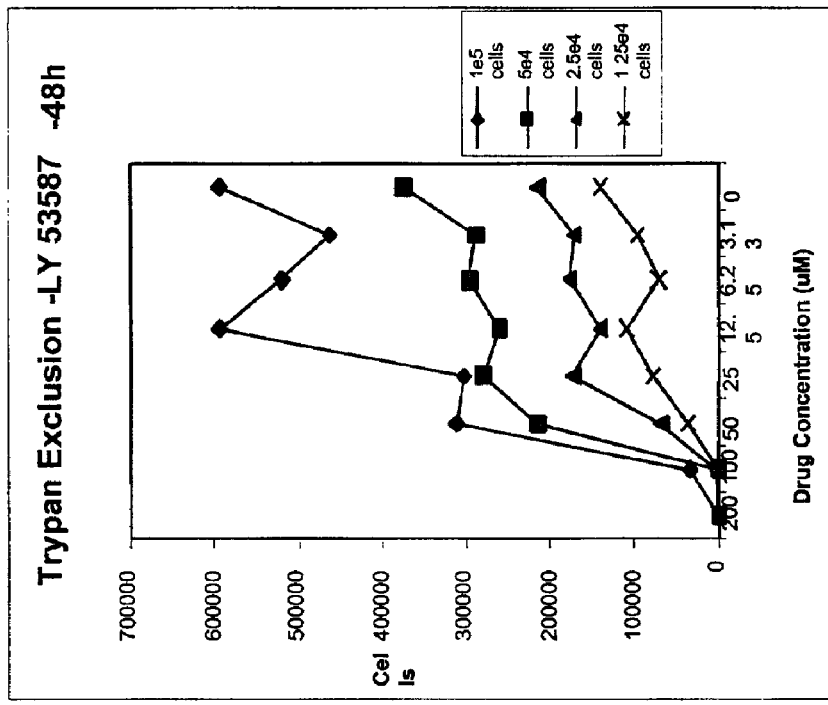
Figure 19A:
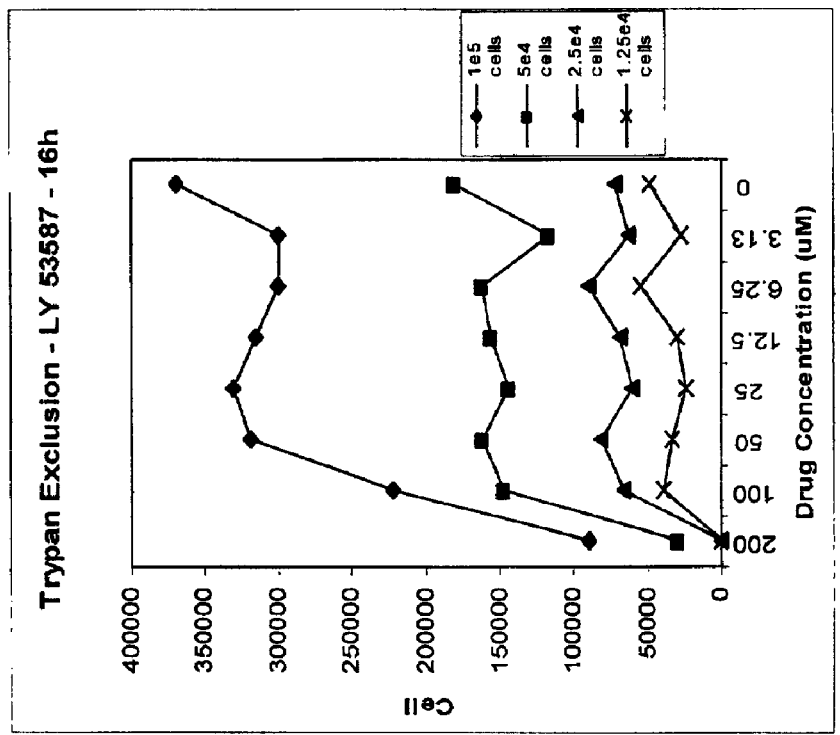

FIG. 19A is a graph depicting the effects on the 5-HT2A/B/C receptor antagonist LY53587 on RPMI 8226 cell viability at 16 hours.

FIG. 19B is a graph depicting the effects on fthe 5-HT2A/B/C receptor antagonist LY53587 on RPMI 8226 cell viability at 48 hours.

Figure 20B:
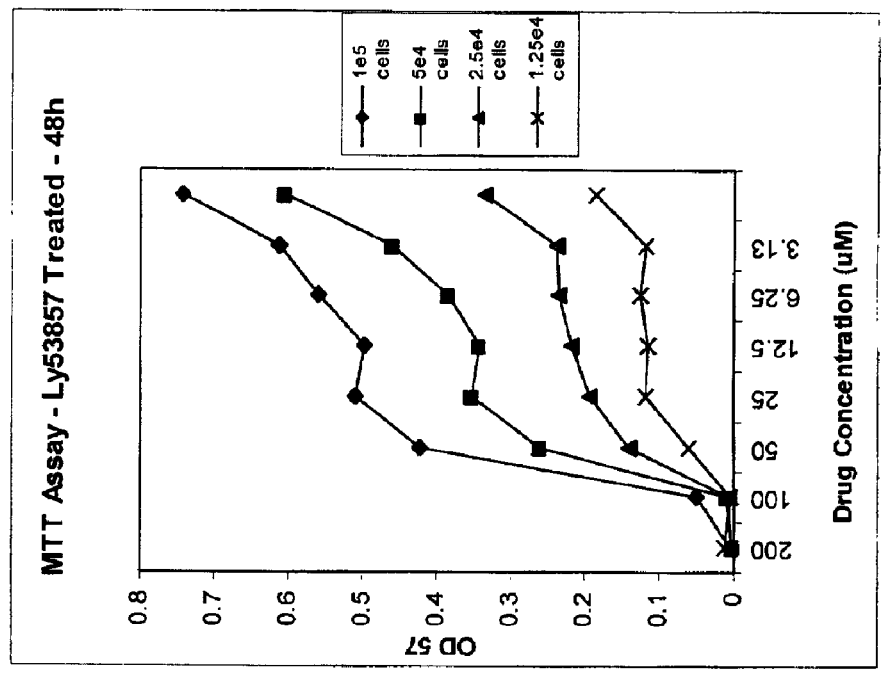
Figure 20A:
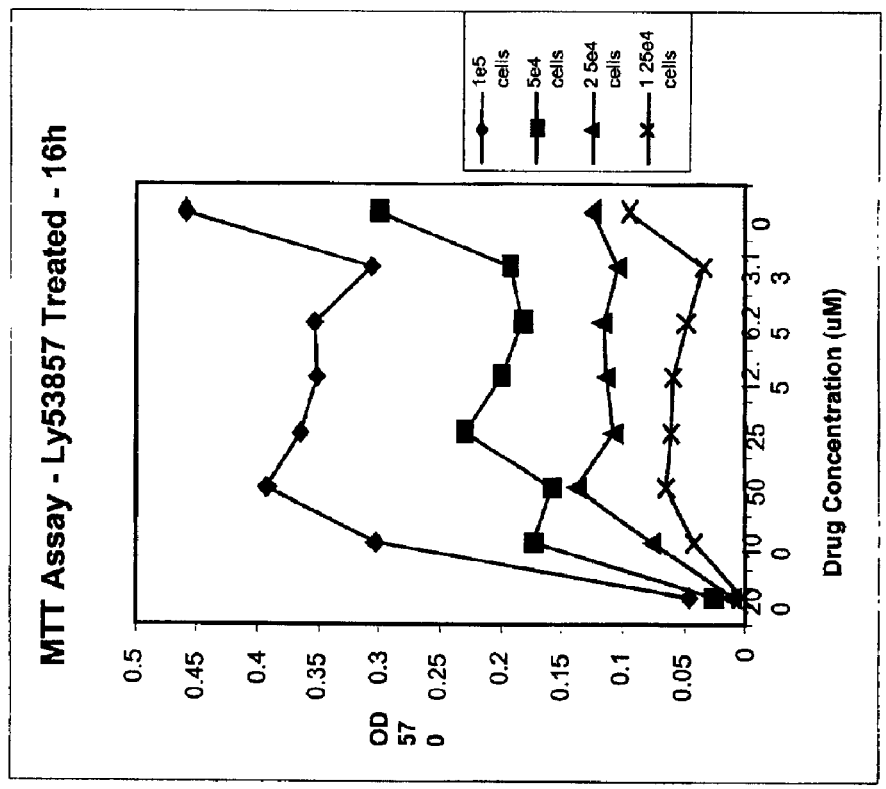

FIG. 20A is a graph depicting the effects of the 5HT-2A/B/C receptor antagonist of mitochondrial activity in RPMI 8226 cells at 16 hours.

FIG. 20B is a graph depicting the effects of the 5HT-2A/B/C receptor antagonist of mitochondrial activity in RPMI 8226 cells at 48 hours.

Figure 20D:
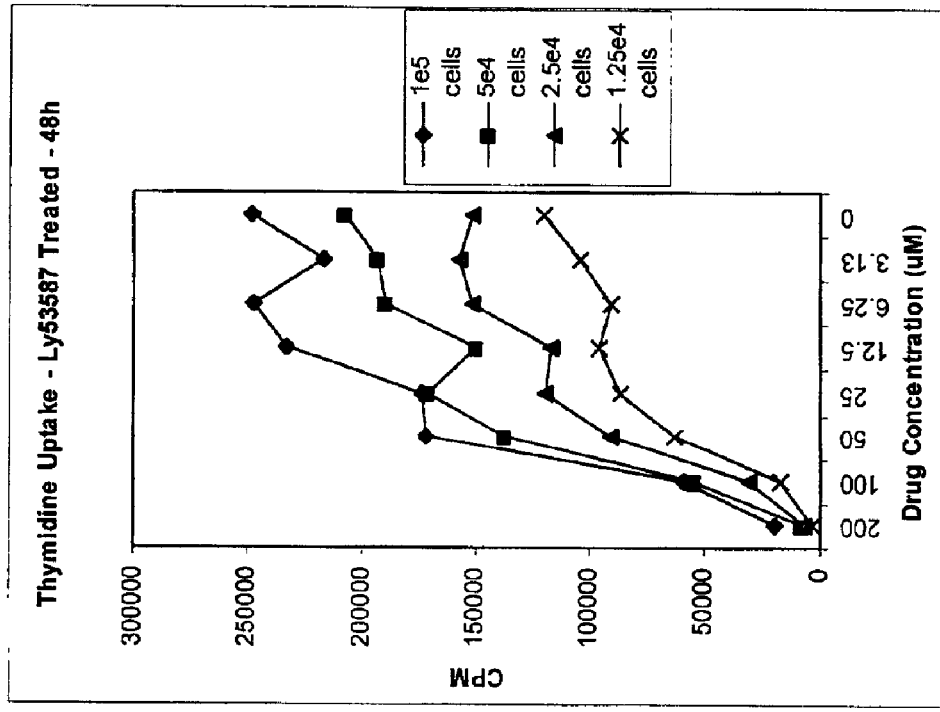
Figure 20C:
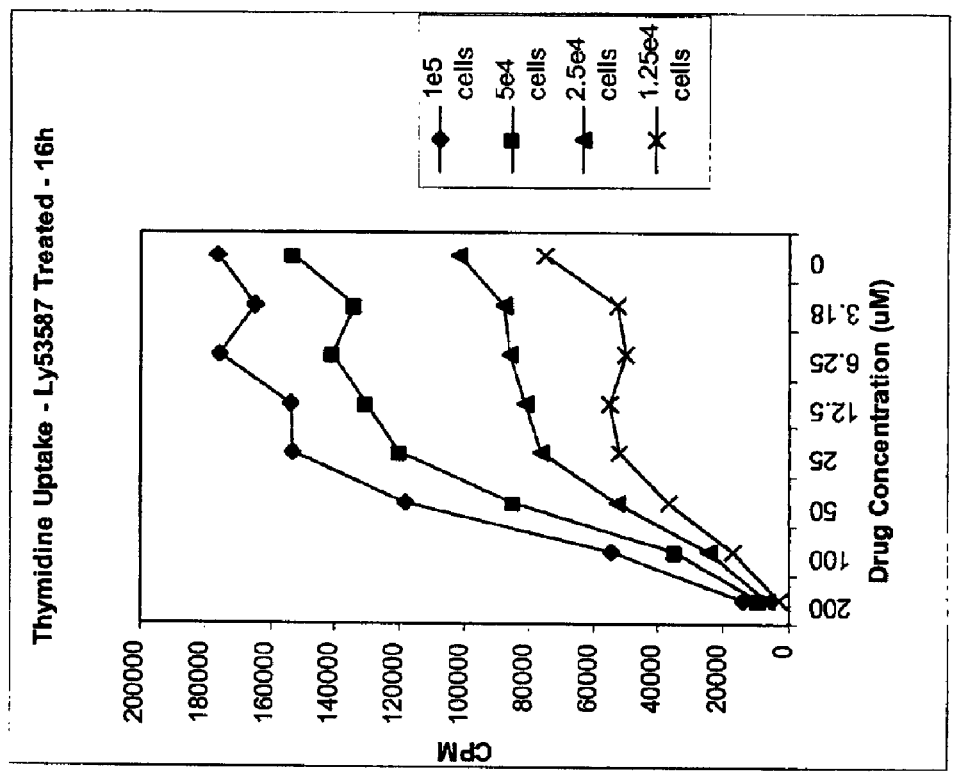

FIG. 20C is a graph depicting the effects of the 5HT-2A/B/C receptor antagonist of DNA synthesis in RPMI 8226 cells at 16 hours.

FIG. 20D is a graph depicting the effects of the 5HT-2A/B/C receptor antagonist of DNA synthesis in RPMI 8226 cells at 48 hours.

Figure 21:
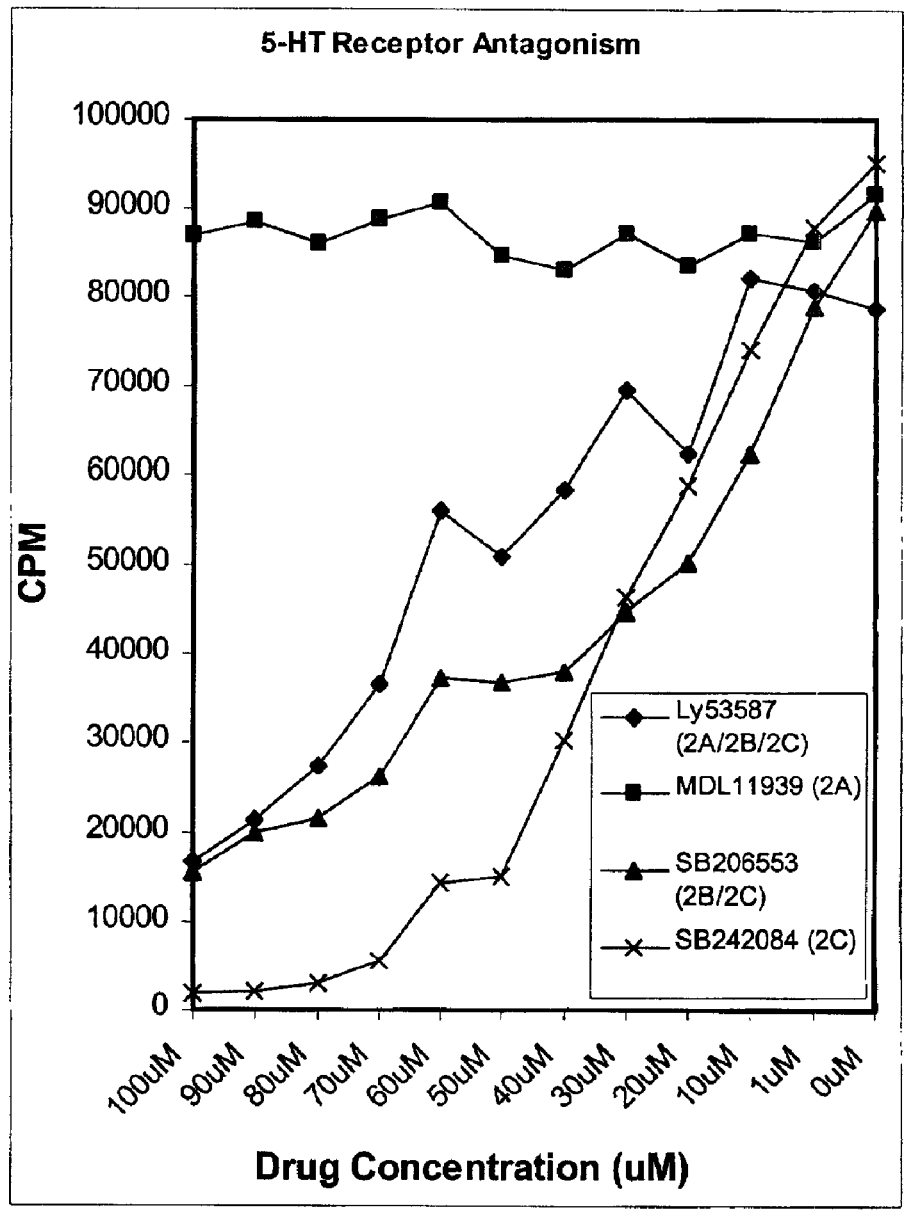

FIG. 21 is a graph depicting the effects of the 5HT-2A/B/C receptor antagonist of DNA synthesis in RPMI 8226 cells.

Figure 22:
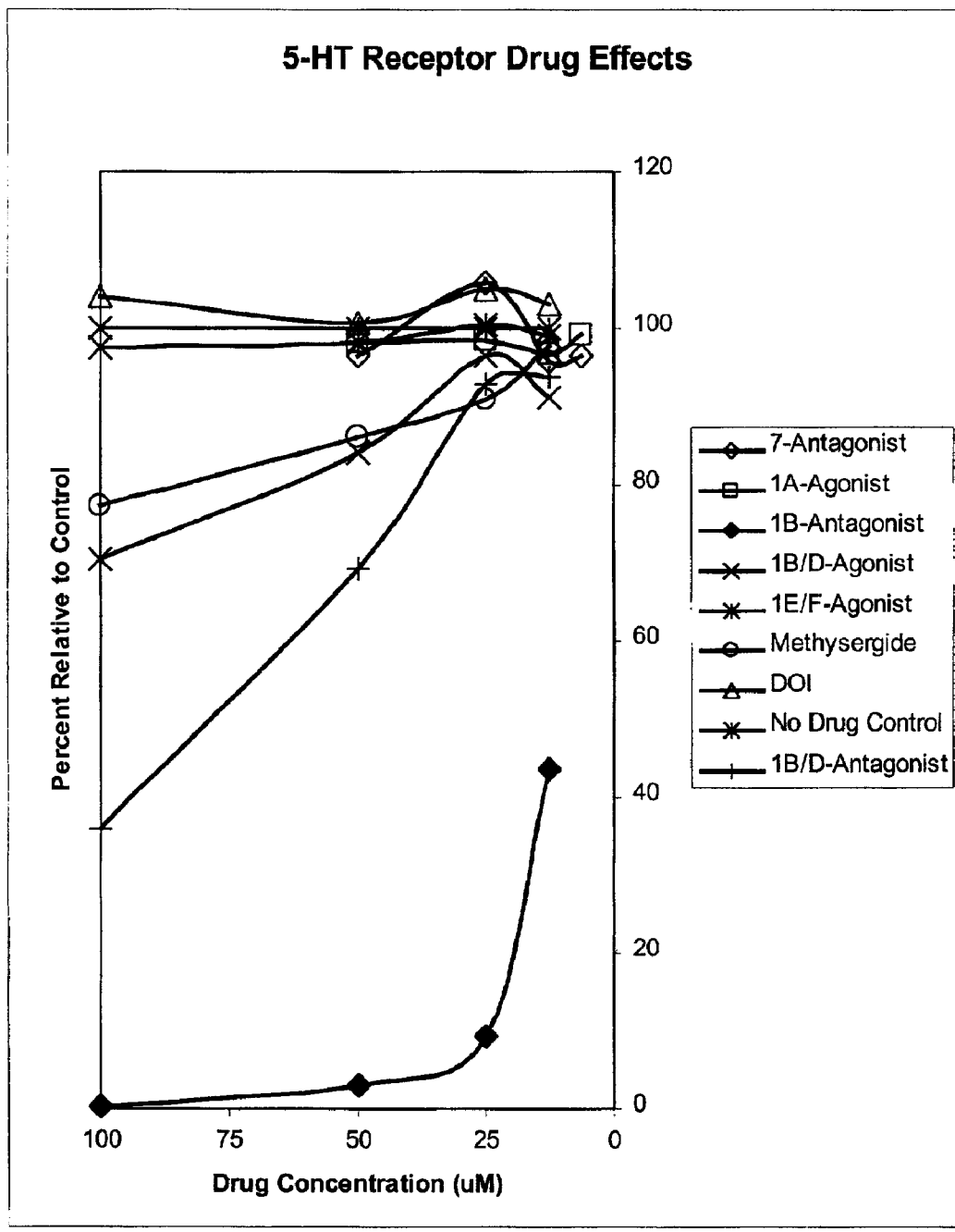

FIG. 22 is a graph depicting the effects of various 5-HT-receptor agonists and antagonists on RPMI 8226 cell proliferation.

Figure 23:
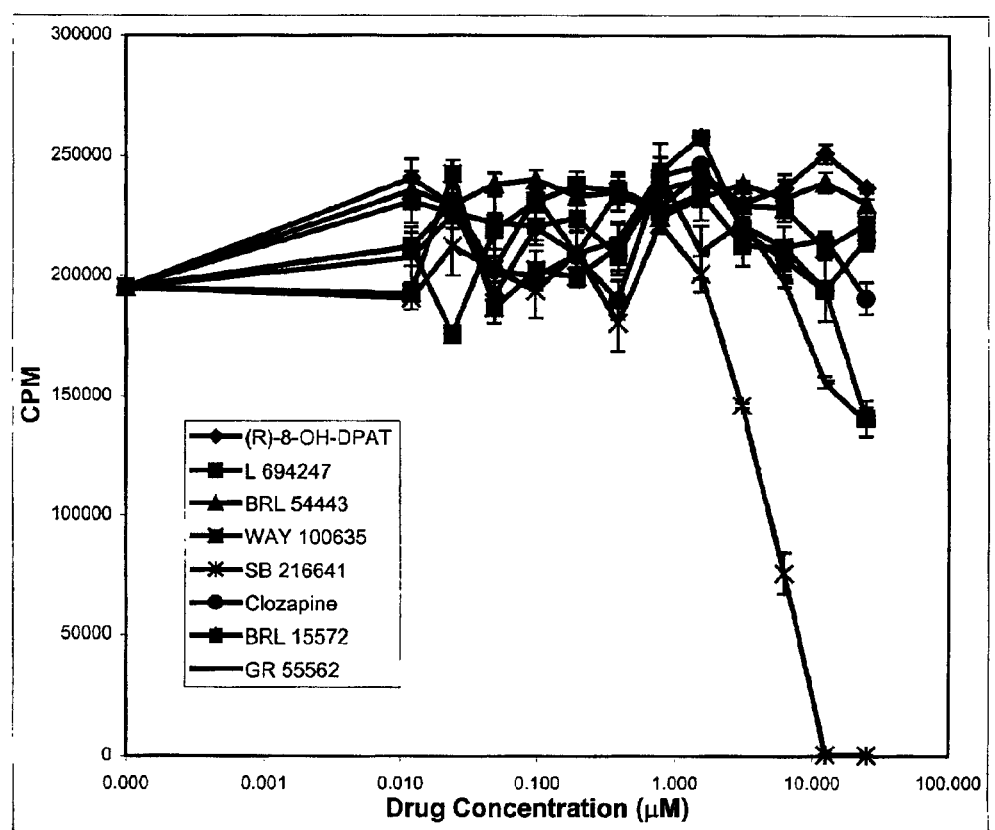

FIG. 23 is a graph depicting the effects of various 5-HT receptor agonists and antagonist targeted to the 5-HTR 1 receptors. The readout of the assay is the cell proliferation of the RPMI 8226 multiple myeloma cells.

Figure 24:
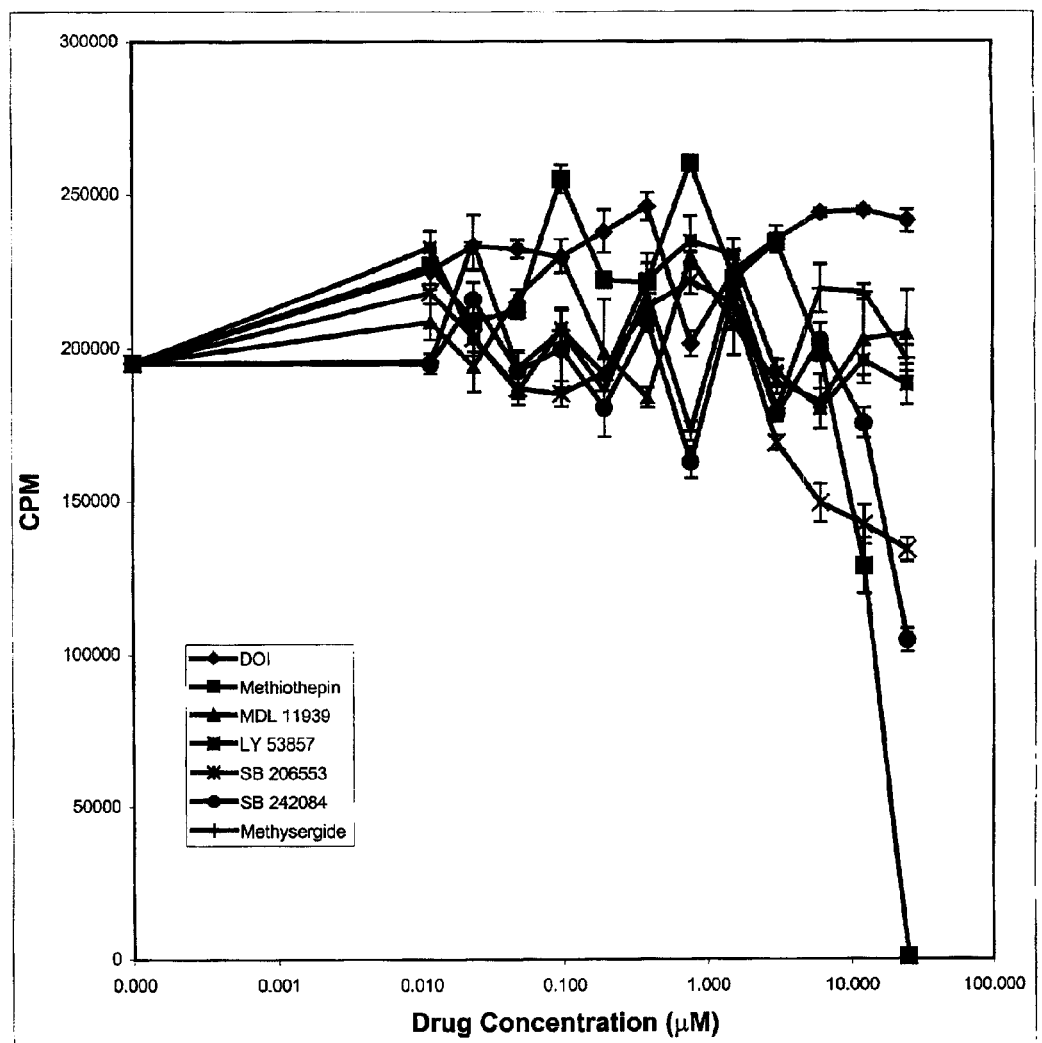

FIG. 24 is a graph depicting the effects of various 5-HT receptor agonists and antagonists targeted to the 5-HTR 2 receptors. The readout of the assay is the cell proliferation of the RPMI 8226 multiple myeloma cells.

Figure 25:
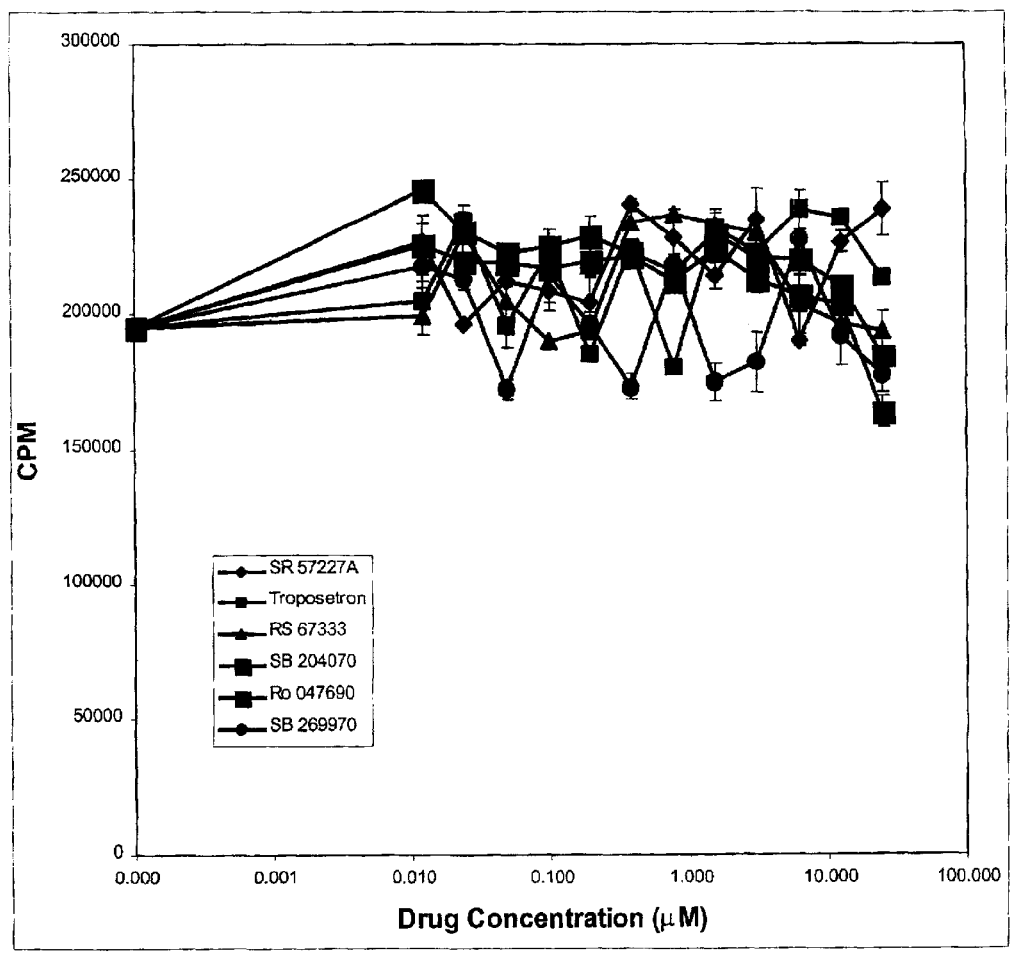

FIG. 25 is a graph depicting the effects of various 5-HT receptor agonists and antagonists targeted to either the 5-HTR 3, 4, 6 or 7 receptors. The readout of the assay is the cell proliferation of the RPMI 8226 multiple myeloma cells.

Figure 26:
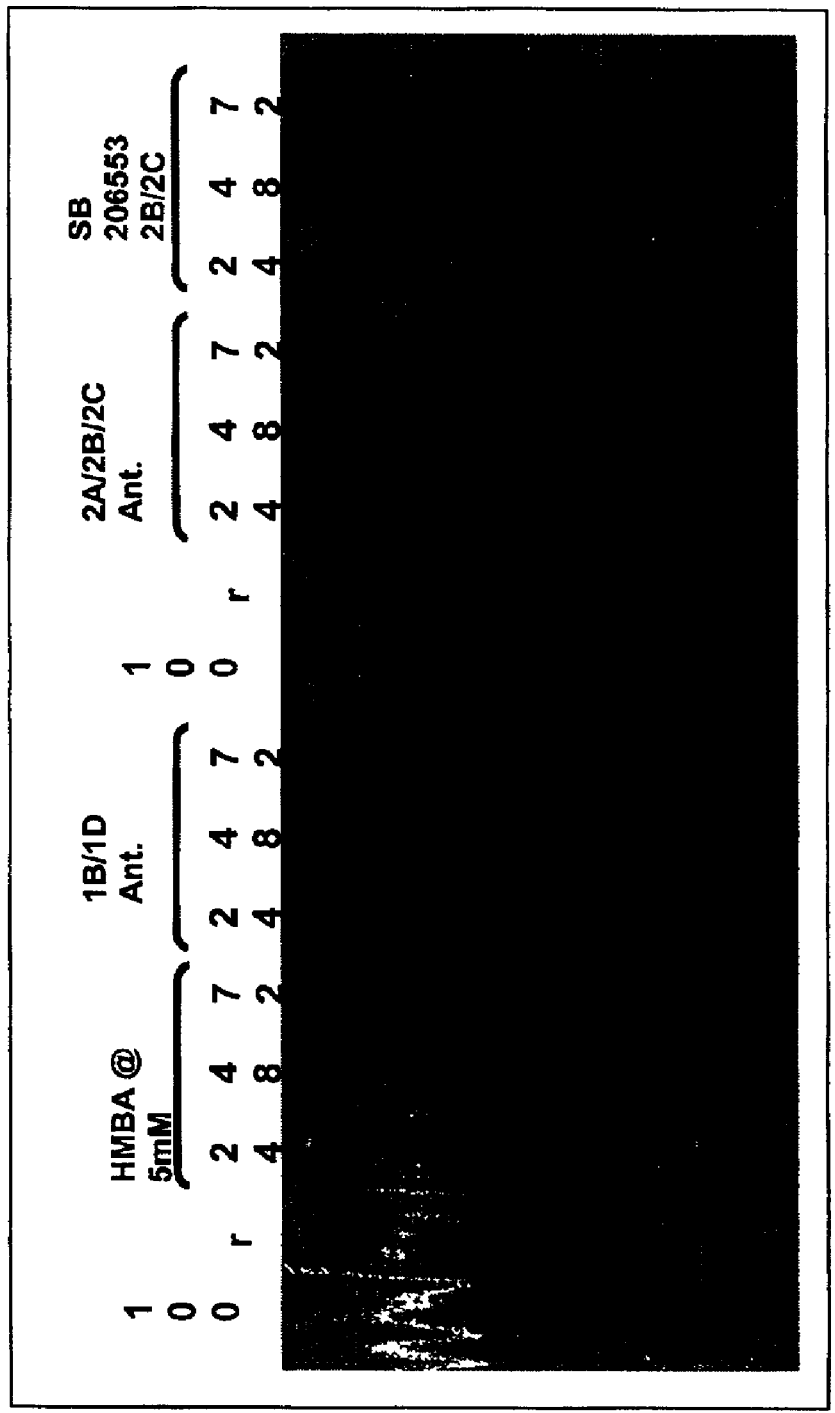

FIG. 26 is an image depicting a gel demonstrating classical DNA fragmentation associated with apoptosis in RPMI 8226 cells treated with various agents, including a 5-HTR 2A/2B/2C.

Figure 27:
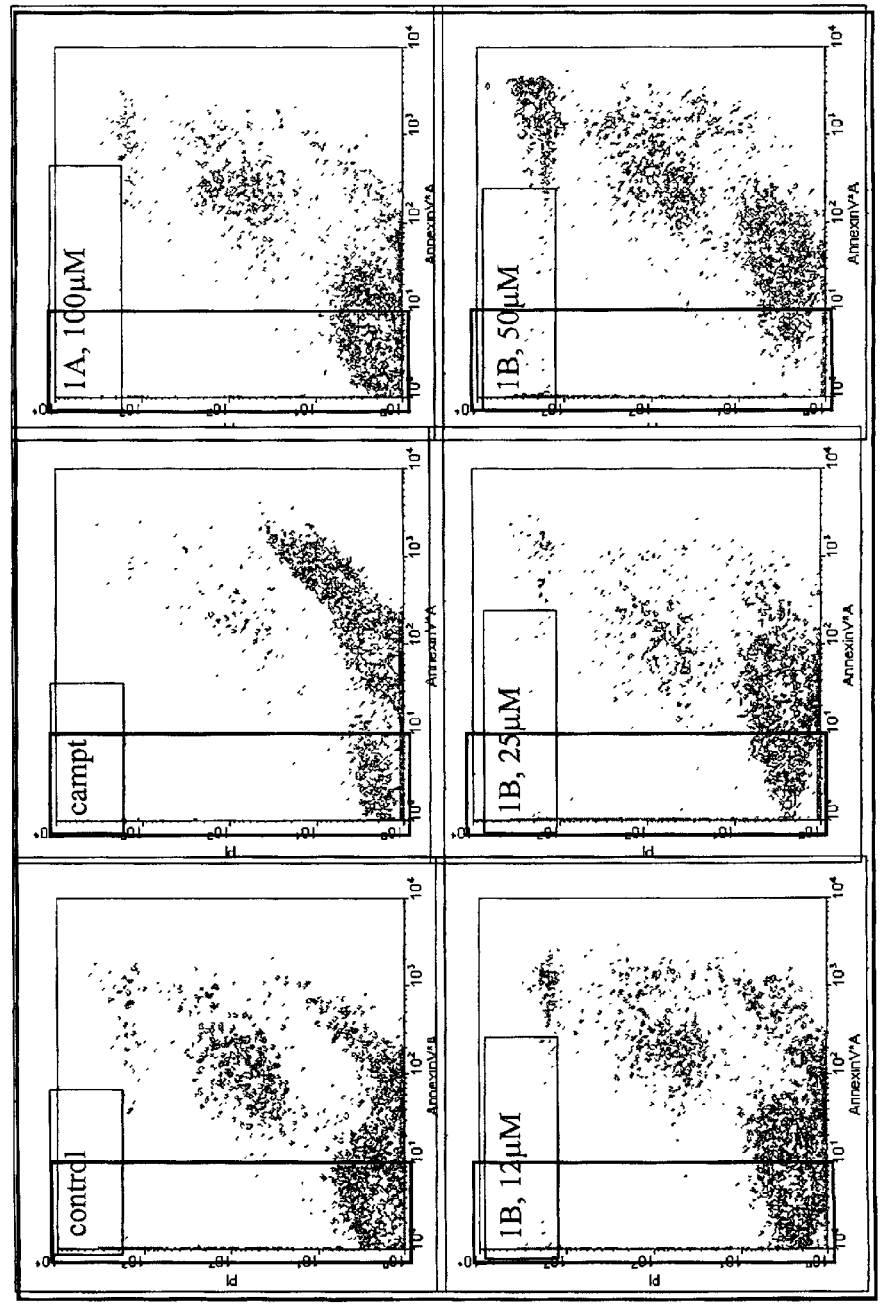
Figure 30A:
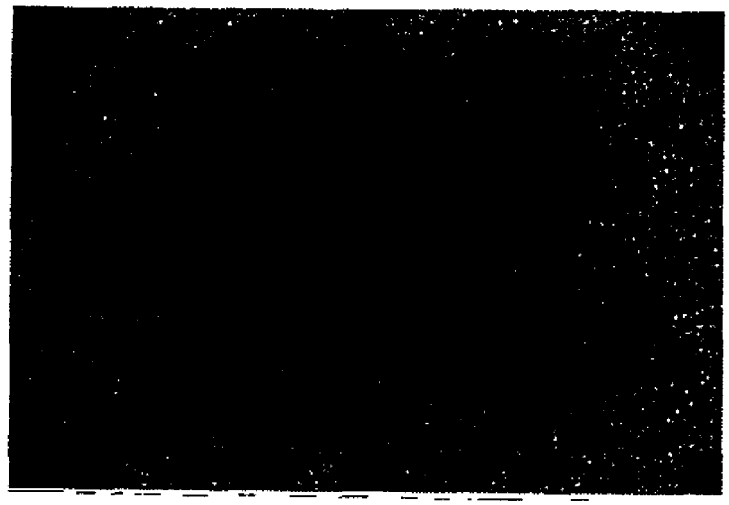
Figure 30B:
Figure 30C:
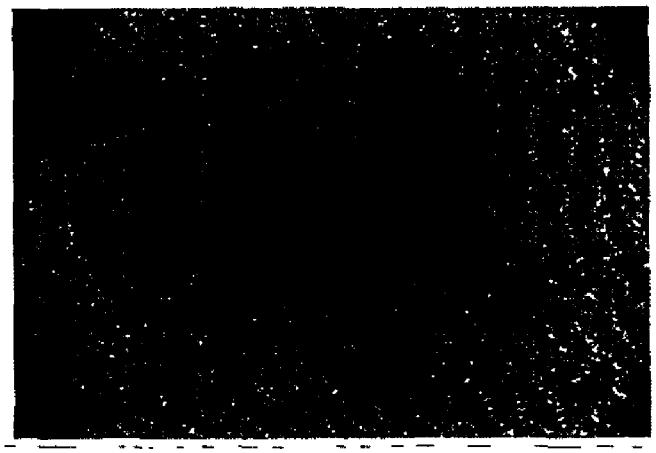
Figure 30D:
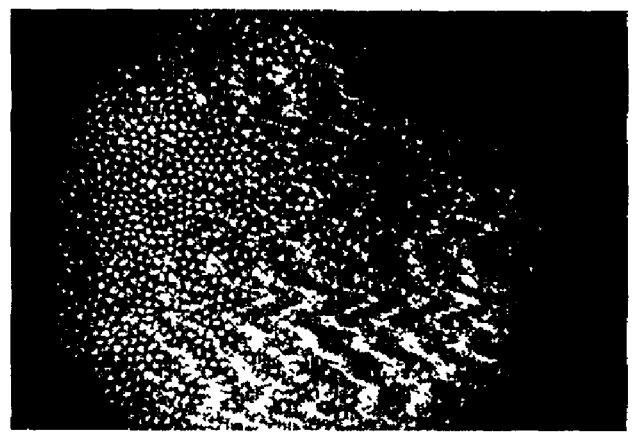

FIG. 27, comprising panels A–F, is an image depicting the FACS profiles of RPMI 8226 cells treated with various concentrations of camptothecin, a selective 5-HTR type 1B/D antagonist, or untreated control cells all stained with annexin (along the ordinate) and propedium iodide (PI) (along the abscissa).

FIG. 28 are 4 images depicting matched Hematoxylin and eosin (top) and bis-benzamide (bottom) stained images of RPMI-8226 cells after 9 hour treatments with 2 $\mu$M camptothecin (left) and 50 $\mu$M SB 216641-treated to inhibit the 5-HT 1B receptor signals (right). Extensive chromatin condensation and nuclear fragmentation is evident in both treatment groups, indicative of widespread apoptosis.

FIG. 29 depicts a matched images of RPMI-8226 cells stained with Hematoxylin and eosin (top) and bis-benzamide (bottom) after 9 hour treatments with 50 $\mu$M SB242084-treated to inhibit the 5-HT 2C receptors signals (right) and vehicle control (left). Homogeneous chromatin-staining is apparent in the control sample, indicative of viable cells, whereas cells treated with SB242084 demonstrated condensed and fragmented chromatin, indicative of apoptotic cells.

FIG. 30, comprising panels A–D, is an image depicting a photomicrograph demonstrating the detectable changes in a cell upon inhibition of serotonergic signalling. The cells were incubated in the presence of a selective type 1B antagonist (SB 216641) and the changes in cell morphology are depicted after 24 hours of treatment.

DETAILED DESCRIPTION OF THE INVENTION

Serotonin family receptors play a significant role in the neurological system and as disclosed in the present invention, in the inmmune system. The data disclosed herein demonstrate that affecting the activation of serotonin type 2 receptors can modulate the immune response. More specifically, inhibition of binding of serotonin with type 2B/2C, and to a lesser extent type 2A, serotonin receptors mediates a decrease or inhibition of T cell activation and, among other things, inhibition of both primary and secondary T cell responses in a mammal. Such inhibition of T cell responses provides a powerful therapeutic method for treatment of, inter alia, autoimmune disease and allogeneic graft rejection, for which there is presently no effective treatment.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By T cell "activation," as the term is used herein, is meant that the T cell, when contacted with a compound, molecule, or cell capable of generating an immune response (e.g., a mitogen such as ConA or PHA), detectably upregulates surface markers, such as CD25, i.e., the IL2 receptor, initiates a phosphorylation cascade involving p56lck, causes the release of cytokines and interleukins, increases DNA synthesis which can be assessed by, among other methods, assessing the level of incorporation of $^3$H-thymidine into nascent DNA strands, and causes the cells to proliferate.

As used herein, a serotonin "agonist" is a composition of matter which, when administered to a mammal, detectably enhances, increases or extends a biological activity attributable to the level or presence of serotonin compared to the biological activity of serotonin in the absence of the composition of matter.

A serotonin "antagonist" is a composition of matter which, when administered to a mammal such as a human, detectably inhibits a biological activity attributable to the level or presence of serotonin.

A serotonin "inverse agonist", is a composition of matter that, when administered to a mammal, detectably inhibits the serotonergic receptor-mediated signal below its basal levels. For instance, an antagonist can prevent the ligand from exerting its positive signaling effect on the receptor, whereas an inverse agonist (also known in the art as a "negative antagonist") will inhibit the receptor-mediated signals below their equilibrium levels. That is, a certain baseline detectable level of signaling via a serotonergic receptor can be present even in the absence of a ligand, and an inverse agonist can reduce that level below the baseline.

By the term "selective agonist" or "selective antagonist," as these terms are used herein, is meant a chemical agent that has at least about a 5-fold greater affinity for the target serotonin receptor type than for any other serotonin receptor family member.

As used herein, to "alleviate" a disease means reducing the severity of one or more symptoms of the disease.

By the term "allogeneic graft," as used herein, is meant grafting of any tissue within a species wherein there is a mismatch of an immunological marker, such as, but not limited to, the major histocompatibility complex (MHC), and/or a minor antigen.

The term "allogeneic graft response", as used herein, means any immune response directed against non-self tissue grafted into a recipient. Grafting procedures include, but are not limited to, administering non-self cells, tissue, or organs during, e.g., bone marrow transplantation, organ transplant, and the like.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Amplification" refers to any means by which a polynucleotide sequence is copied and thus expanded into a larger number of polynucleotide molecules, e.g., by reverse transcription, polymerase chain reaction, and ligase chain reaction.

The term "apoptosis," as used herein, means an active process, involving the activation of a preexisting cellular pathway, induced by an extracellular or intracellular signal, causing the death of the cell. In particular, the cell death involves nuclear fragmentation, chromatin condensation, and the like, in a cell with an intact membrane.

By the term "applicator," as the term is used herein, is meant any device including, but not limited to, a hypodermic syringe, a pipette, and the like, for administering the inhibitor of serotonin interaction with a serotonin type 2 receptor (e.g., a serotonin type 2 receptor antagonist) of the invention to a mammal.

A "cell cycle process," as used herein, means any cellular function or process associated with the cell cycle and the various phases thereof. Thus, a cell cycle process is one associated with, or which mediates or is involved in, the cell progressing through any portion of the cell cycle.

Inhibition of serotonin signaling is "deleterious" to a cell, as the term is used herein, where the inhibition mediates a detectable decrease in the viability of the cell. Cell viability can be assessed using standard methods that are well-known in the art, including, but not limited to, assessing the level of biomolecular synthesis (e.g., protein synthesis, nucleic acid synthesis, and the like), trypan blue exclusion, MTT reduction, uptake of propidium iodide, exposure of phosphatidylserine on the cell surface, DNA fragmentation and/or ladder formation, and the like.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount", as used herein, is meant an amount of an inhibitor that is sufficient to mediate a detectable decrease in transmission of serotonin signaling via a serotonin receptor on a cell. Transmission of a serotonin signal can be assessed using standard methods well-known in the art, such as, but not limited to, those described elsewhere herein, including, for example, assessing the level of binding of serotonin with a receptor and/or assessing the level of activation of a cell.

The skilled artisan would understand that the amount varies and can be readily determined based on a number of factors such as the disease or condition being treated, the age and health and physical condition of the mammal being treated, the severity of the disease, the particular compound being administered, and the like. Generally, the dosage will be set between 1 mg/kg and 25 mg/kg. In one embodiment, the drug is administered through intravenous bolus injection. This type of bolus administration can be used to ensure that all of the immunologically relevant cells encounter sufficient quantity of the drug in order to block their receptor-mediated signals. However, the invention is not limited to this method of administration.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as the term is used herein, means any cell involved in the mounting of an immune response. Such cells include, but are not limited to, T cells, B cells, NK cells, antigen-presenting cells, and the like.

By the term "an inhibitor of the interaction of serotonin with a serotonin type 2 receptor," as used herein, is meant any compound or molecule that detectably inhibits signaling via a serotonin type 2 receptor. Such compounds include a serotonin receptor antagonist, an inverse agonist, and the like.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids that have been substantially purified from other components that naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA that is part of a hybrid gene encoding additional polypeptide sequence.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector cart be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene that is expressed in a recombinant host cell wherein the gene comprises a recombinant polynucleotide, produces a "recombinant polypeptide."

A "recombinant polypeptide" is one that is produced upon expression of a recombinant polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

By the term "serotonin family receptor" is meant any receptor which can be classified as a serotonin, adrenergic, histamine, melatonin, or dopaminergic receptor. That is, the receptor specifically binds with any of these molecules and does not significantly bind with other molecules in a sample.

A "serotonin receptor" includes a polypeptide that specifically binds with serotonin.

"Serotonin signal," as the term is used herein, means a change in the balance of any intracellular biochemical pathway as a result of a receptor-mediated interaction with serotonin, a specific drug interaction with any serotonin-specific receptor, or both, that results in the change.

Similarly, "activation of a serotonin" receptor, as used herein, means that binding of serotonin with a serotonin receptor on a cell induces the typical cascade of intra and extracellular events associated with such binding.

A "receptor" is a compound that specifically binds with a ligand.

By the term "specifically binds," as used herein, is meant a receptor which recognizes and binds serotonin family proteins present in a sample (i.e., dopaminergic proteins, adrenergic protein, histamines, melatonin, and serotonin), but does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

Description

The invention relates to novel methods for modulating the immune response in a mammal. The invention relates to the discovery that inhibiting the interaction of serotonin with serotonin type 2 receptors on the cell using a specific antagonist, and/or inhibiting the signal(s) transduced through the serotonin type 2 receptor using an inverse agonist, can inhibit activation of T cells. The invention discloses methods of inhibiting various immune diseases, disorders or conditions by inhibiting the serotonin/serotonin type 2 receptor interaction using, inter alia, serotonin type 2 receptor antagonists known, or to be developed, that by inhibiting the serotonin/receptor interaction, prevent or inhibit T cell activation thereby inhibiting an immune response otherwise mediated by such interaction.

I. Methods

A. Methods of Modulating an Immune Response

The present invention includes a method of modulating an immune response in a mammal. The method comprises administering an inhibitor of the interaction of serotonin with a serotonin receptor to a mammal in need of such treatment. This is because, as would be appreciated by one skilled in the art armed with the teachings of the present invention, inhibiting the interaction of serotonin and a 5-HT receptor inhibits or prevents activation of T cells comprising the receptor. Inhibition of the T cells prevents, in turn, the generation of an immune response as amply demonstrated by the data disclosed herein.

More specifically, the invention relates to inhibiting interaction of serotonin with serotonin type 1B, type 2, type 4 and type 6 receptors using various inhibitors of such interaction. That is, one skilled in the art would understand, based upon the disclosure provided herein, that compounds that inhibit binding of serotonin with a serotonin type 1B, 2 (A, B, and/or C), 4 and 6 receptors encompass, but are not limited to, an antibody, an antisense nucleic acid, a ribozyme, a small molecule, a peptidomimetic and a pharmaceutical compound, either known or to be developed, which inhibits serotonin interaction with a serotonin receptor.

One skilled in the art would appreciate, based on the disclosure provided herein. The skilled artisan would appreciate that an inhibitor of the invention includes molecules and compounds that prevent or inhibit the serotonin receptor from being accessible to serotonin on the cell surface. That is, the invention contemplates that an antisense and/or antisense molecule that prevents the expression of the receptor such that the receptor is not present on the surface of the cell can be an inhibitor of the invention.

More preferably, the inhibitor of serotonin interaction with a serotonin type 1B, 2, 4 or 6 receptor is a type 1, 2, 4 and 6 receptor antagonist such as, among others, risperidone, ketanserin, mianserin, LY 53857, SB 206553, SB 242084, MDL 11939, SB 216641, methiothepin, and the like. Further, the skilled artisan would appreciate, based upon the disclosure provided herein, that type 1B, 2, 4 and 6 receptor antagonists include such antagonists as are discovered in the future since any type 1B, 2, 4 or 6 receptor antagonist, which would be determined to be one according to well-established pharmacological criteria known in the art, would be understood by the routineer as being capable of inhibiting interaction of serotonin with the receptor such that T cell activation is inhibited thereby inhibiting an immune response as disclosed throughout the specification and as amply demonstrated and exemplified therein. Thus, the present invention is not limited in any way to the particular type 1B, 2 (A/B/C), 4 and 6 receptor antagonists set forth herein; rather, the invention includes those antagonists known in the art or to be developed in the future.

The serotonin type 2 receptor antagonist can be specific for any one of each of type 2A, type 2B, and 2C, or any combination thereof. Alternately, the invention encompasses type 2 receptor antagonists that are not specific and which affect binding of serotonin with any of the type 2 receptors. Serotonin type 2 receptor antagonists, both specific and non-specific, include, but are not limited to risperidone, mianserin, ritanserin, ketanserin, methysergide, methoxygramine, cyproheptadine, clozapine, SB 206553, LY 53857, MDL 11939, SB 242084, metergoline, N-desmethylclozapine, pirenperone, clozapine N-oxide, octoclothepin, loxapine, mesulergine, and the like, and any combination thereof.

Additionally, one skilled in the art would appreciate that the invention encompasses inhibiting transmission of a serotonin-mediated signal transmitted via any serotonin receptor either known or to be identified in the future, where inhibiting the serotonin signal affects cellular growth, division, viability, apoptosis, and the like, and where the cell is involved in, or mediates, an immune response. Thus, the invention is not limited to inhibition of signal transmission via type 1B, 2, 4 and 6 serotonin receptors; rather, the invention includes, but is not limited, inhibiting signaling via a serotonin receptor where the inhibition inhibits an immune response.

Once skilled in the art, based upon the disclosure provided herein, would appreciate that such inhibition can be mediated by using, among other things, an antibody, an antisense nucleic acid, a ribozyme, a small molecule, a peptidomimetic and pharmaceutical compounds, either known or to be developed, which inhibits serotonin interaction with a serotonin type 1 receptor. That is, the invention encompasses using a type 1 receptor inhibiting compound such as, but not limited to, SB-216641 which preferentially inhibits a type 1B, and BRL-15572, which selectively inhibits a type 1D receptor (see, e.g., Price et al., 1997, Naunyn-Schmiedeberg's Arch. Pharmacol. 356:312–320). This is because, as is demonstrated by the data disclosed elsewhere herein, inhibition of serotonin signaling mediated via a type 1B receptor mediates inhibition of cell growth, and, more preferably, apoptosis as indicated by DNA-ladder which can be associated with a detectable increase in cell size.

However, the present invention is not limited to these, or any other, serotonin receptor inhibitors. More specifically, as discussed previously elsewhere herein, these compounds encompass known compounds and compounds developed in the future that inhibited interaction of serotonin with a serotonin receptor. A list of known setotonin receptor agonists and antagonists is publicly available at URL http:\\www.tocris.com, which site comprises an extensive review by G.A. Kennet of the known properties of the various serotonin receptors discussing the various compounds that affect their biological activity (Kennet, published May 1997, URL http:\\www.tocris.com/serotonin.htm One skilled in the art would understand, once armed with the teachings disclosed herein, that the present invention encompasses inhibiting serotonin binding with a serotonin receptor using an antibody that specifically binds with the receptor. Antibodies that specifically bind with a serotonin receptor, including antibodies that bind with each receptor type, are well-known in the art and/or can be produced using standard methods known to the skilled artisan.

The skilled artisan would further appreciate that the antibody can be administered as a protein, as a nucleic acid encoding the protein, or both. That is, there are numerous vectors well-known in the art for providing a protein, including an antibody, to a cell or tissue. Thus, the invention includes administering an antibody that specifically binds with a serotonin receptor thereby inhibiting binding of serotonin with the receptor and the antibody can be administered to a cell or the antibody can be administered by administering a nucleic acid encoding the antibody to the cell, and such administration of an antibody is included in the invention.

Moreover, the skilled artisan would appreciate, based upon the disclosure provided herein, that the present invention encompasses inhibition of transmission of a serotonin signal otherwise transmitted via a serotonin receptor by preventing expression of a serotonin receptor on a cell that would otherwise express the receptor. For instance, the skilled artisan would understand that the present invention includes administering a ribozyme or an antisense nucleic acid molecule to a cell thereby inhibiting expression of a serotonin receptor in the cell, where the design and use of such molecules to inhibit expression of a protein of interest in a cell are well-known in the art as follows briefly.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules can be produced synthetically and then provided to the cell. Antisense oligomers of between about 10 to about 100, and more preferably about 15 to about 50 nucleotides, are preferred, since they are easily synthesized and introduced into a target cell. Synthetic antisense molecules contemplated by the invention include oligonucleotide derivatives known in the art which, have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which, are four bases in length, while hammerhead-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In addition to administering an antibody to a cell to inhibit binding of serotonin with a serotonin receptor on the cell surface, the invention encompasses administering an antibody that specifically binds with the serotonin receptor of interest, or a nucleic acid encoding the antibody, wherein the molecule further comprises an intracellular retention sequence such that antibody binds with the serotonin receptor and prevents its expression at the cell surface. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11–17). Thus, the invention encompasses methods comprising inhibiting binding of serotonin with a receptor of interest where the receptor is present on the cell surface (e.g., antibodies, chemical compounds, small molecules, peptidomimetics, drugs, and the like), as well as methods of inhibiting the binding comprising inhibiting the receptor being present on the cell surface (e.g., ribozymes, antisense molecules, intrabodies, and the like), and such methods as become known in the future for inhibiting ligand:receptor interaction on the cell surface between serotonin and a serotonin receptor.

The skilled artisan would appreciate, based upon the disclosure provided herein, that an inhibitor of serotonin interaction with a serotonin (type 1B, 2, 4 or 6) receptor can be administered in combination with any other such inhibitor. Moreover, the invention encompasses administration of at least one inhibitor of serotonin inhibitor (e.g., an antibody, an antisense nucleic acid, a ribozyme, a peptidomimetic, a serotonin receptor antagonist, and the like) can be administered in combination with (before, simultaneously, and/or after) another immunomodulating agent such as, but not limited to, regulators of gene expression (e.g., glucocorticoids that inhibit expression of Interleukin 2, and the like), alkylating agents that are known mutagens (e.g., cyclophosphamide), inhibitors of kinases and phosphatases which act on the calcineurin and JNK/p38 kinase pathways and the cyclin kinase cascade (e.g., CyclosporinA, Tacrolimus [FK506], and Rapamycin), inhibitors of de novo purine synthesis which act as inhibitors of guanosine nucleotide synthesis and are used to prevent allograft rejection and to treat ongoing rejection (e.g., Mycophenolate motefil), and inhibitors of de novo pyrimidine synthesis which are used to treat patients afflicted with rheumatoid arthritis (e.g., Leflunomide). Therefore, the invention encompasses administering at least one inhibitor of serotonin interaction with serotonin (type 1B, 2, 4 and 6) receptor in concert with traditional immunomodulating substances and compounds.

One skilled in the art would understand, once armed with the teachings of the invention, that since binding of serotonin with a serotonin type 2 receptor on an immune cell (e.g., a lymphocyte, more specifically, a T cell, or an antigen presenting cell such as, e.g., a B cell or macrophage) is required for receptor activation which, in turn, mediates T cell activation, inhibiting serotonin/receptor interaction modulates an immune response mediated by such immune cell. Further, the data disclosed herein demonstrate that inhibition of transmission of a serotonin signal via a serotonin type 1B, type 4, or type 6 receptor also inhibits activation of an immune cell expressing that receptor, that inhibition of serotonin binding with those serotonin receptors also inhibits cell activation and, therefore, also inhibits an immune reaction by the cell and, in turn, inhibits an immune response mediated by that cell. That is, inhibiting the serotonin receptor-mediated interaction(s) on an immune cell affects the immune response (i.e., the immune reaction) generated by the affected immune cell (e.g., the mitogenic response mediated by receptor/ligand binding is inhibited such that T cell proliferation does not occur, and/or apoptosis can occur, and the like) such that the response, immune or otherwise, by that cell is detectably increased or decreased relative to the immune response produced by an otherwise identical cell in the absence of the antagonist. The data disclosed herein clearly demonstrates that inhibiting the signal mediated by the 5HT 1B, 2, 4 and 6 receptors, at any point during the activation response, whether by allogeneic stimulation or mitogenic stimulation, results in the immediate cessation of the response.

Therefore, the data disclosed herein amply support a method of inhibiting an immune response in a mammal, preferably a human, since inhibition of serotonin binding with a serotonin (type 1B, 2A, 2B, 2C, 4, and/or 6) receptor inhibits activation of an immune cell, thereby inhibiting an immune reaction by the cell, which in turn inhibits an immune response mediated by that cell.

Similarly, the invention encompasses a method of inhibiting an immune reaction by an immune cell. This is because, as more fully set forth elsewhere herein, inhibition of serotonin binding with a serotonin receptor on the immune cell inhibits activation of the cell, which in turn inhibits an immune reaction by that cell when compared to the immune reaction by that cell in the absence of inhibition of serotonin binding and/or when compared with the immune reaction of an otherwise identical cell wherein serotonin binding with its receptor is not inhibited.

By the same token, the skilled artisan would appreciate, based upon the disclosure provided herein, that the invention includes a method of modulating an immune response in a mammal, where that immune response is mediated by an immune cell activated by serotonin signaling. This is because, as pointed out previously elsewhere herein, immune cell activation requires binding of serotonin with its cognate type 1B, 2A, 2B, 2C, 4 and/or 6 receptor such that inhibiting such binding inhibits activation which, in turn, prevents the cell from mediating an immune response. Thus, one of ordinary skill in the art would understand that inhibiting serotonin signaling, which can be accomplished by a variety of methods as more fully set forth elsewhere herein, inhibits generation of an immune response requiring such signaling.

Additionally, the skilled artisan would appreciate, based upon the disclosure provided herein, that the invention encompasses a method of inhibiting an immune response mediated by activation of a serotonin receptor on a T cell. That is, as discussed previously elsewhere herein, inhibition of serotonin binding with a serotonin receptor, e.g., type 1B, 2A, 2B, 2C, 4, and 6, on an immune cell, preferably, a T cell, inhibits activation of the cell and inhibits, in turn, an immune reaction by that cell, and an immune response mediated by that cell. Thus, the skilled artisan would understand, based upon the disclosure provided herein, that such a method is included in the invention.

The invention also includes a method of inhibiting activation of an immune cell in a mammal, preferably, a human, wherein the activation is mediated by activation of a serotonin receptor on the cell. Again, this is because, as more fully set forth elsewhere herein, the data disclosed herein demonstrate, for the first time, that inhibition of serotonin signaling via a serotonin type 1B, 2 (A/B/C/), 4 or 6 receptor on an immune cell, inhibits activation of the cell, and therefore, also inhibits the immune response that would otherwise be produced by that cell. As more fully set forth elsewhere herein, methods of inhibiting serotonin signaling are described herein, or are well known in the art, and are included in the invention.

The skilled artisan would appreciate, based upon the disclosure provided herein, that the methods disclosed herein are useful for inhibiting any immune response which is not beneficial to a mammal. Such unwanted immune responses include, but are not limited to, an immune response associated with a disease, disorder or condition, including a secondary immune response, an autoimmune response, an allogeneic graft rejection response, and the like.

Thus, the invention includes a method of inhibiting a secondary immune response in a mammal. That is, where the secondary immune response is mediated by a cell requiring activation via a serotonin signal, the serotonin signal can be inhibited as disclosed more fully elsewhere herein, by inhibiting binding of serotonin with a serotonin type 1B, 2, 4, and 6 receptor on the cell. This inhibition, in turn, inhibits activation of the cell, which then inhibits an immune response mediated by the cell, such as, but not limited to, a secondary immune response, a response mediated by a CD8+ cell, and/or an immune response mediated by a CD4+ cell.

The compound or molecule that inhibits the serotonin receptor-mediated signals (e.g., a pharmaceutical compound such as a serotonin receptor antagonist or an inverse agonist) can be administered to a cell, a tissue, or an animal or to inhibit interaction of serotonin with a serotonin type 1B, 2, 4 and/or 6 receptor on a cell, a tissue, or in an animal. Whether the inhibitor is an antibody or a serotonin type 1B, 2, 4 and/or 6 receptor antagonist, methods for the safe and effective administration of the inhibitors described herein are know to those skilled in the art. For instance, the administration of serotonin antagonists is described in the standard literature. That is, the administration of many serotonin-affecting agents is set forth in the Physician's Desk Reference (1996 edition, Medical Economics Co., Montvale, N.J.), the disclosure of which is incorporated by reference as if set forth in its entirety herein.

Further, the parameters for administering a serotonin receptor inhibitor are well-known in the pharmaceutical arts and need not be repeated herein.

The compositions are also useful to treat a disease, disorder or condition mediated by altered expression of the receptor such that decreasing or increasing receptor expression or the level of the protein in a cell, tissue, or animal, is beneficial to the animal. That is, where a disease, disorder or condition in an animal is mediated by or associated with altered level of expression of the serotonin receptor or protein level, the composition can be used to modulate such expression or protein level of the receptor.

For administration to the mammal, a compound, an inhibitor of the interaction of serotonin with a serotonin type 1B, 2, 4 and/or 6 receptor, a polypeptide, or a nucleic acid encoding it, and/or an antisense nucleic acid complementary to all or a portion thereof, can be suspended in any pharmaceutically acceptable carrier, for example, HEPES buffered saline at a pH of about 7.8.

Other pharmaceutically acceptable carriers that are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the receptor protein and/or a nucleic acid encoding the same according to the methods of the invention.

Compounds which are identified using any of the methods described herein may be formulated and administered to a mammal for treatment of immune system conditions (i.e., autoimmune diseases and allograft rejection), are now described.

The invention encompasses the preparation and use of pharmaceutical compositions comprising a compound useful for treatment of a wide variety of disorders such as T cell lymphomas, autoimmune disorders (see infra), complications arising from solid organ transplants, skin graft rejection, graft versus host disease in bone marrow transplants, and the like.

Such a pharmaceutical composition can consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, calts, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations that are useful include those that comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, and the like. Preferably, the compound is, but need not be, administered as a bolus injection that provides lasting effects for at least one day following injection. The bolus injection can be provided intraperitoneally.

The skilled artisan would understand that by preventing the establishment of a T cell response, the methods of the invention also provide a method of inhibiting a secondary response since, by abrogating or decreasing the initial response, the production of a secondary response is also inhibited.

Likewise, the skilled artisan would appreciate that the invention encompasses a method of treating a disease mediated by a cell where the cell requires transmission of a serotonin signal via a serotonin receptor on the cell. This is because, as more fully set forth elsewhere herein, certain cells require a serotonin signal such that inhibition of the signal inhibits certain processes that would otherwise be mediated by that cell. Where the cell is involved in, associated with, or mediates a disease, disorder or condition that requires that the cell receive a serotonin signal, inhibition of the signal inhibits the participation of the cell in such disease, disorder or condition. Such conditions, disorders, and diseases are set forth elsewhere herein.

In essence, once it is determined, using methods well known in the art, and/or such methods as are disclosed and/or exemplified elsewhere herein, that the disease, disorder, or condition is mediated by a cell requiring serotonin signaling via a serotonin type 1B, 2, 4 or 6 receptor, such signaling can be inhibited by a variety of methods and the disease, disorder or condition can thereby be treated and/or alleviated. Once the requisite serotonin signaling is inhibited, the cell no longer mediates the disease, disorder or condition, thereby treating and/or alleviating that disease, disorder or condition. Diseases that can be treated according to the methods of the invention include, but are not limited to myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Guillian-Barre Syndrome, vasculitis, multiple sclerosis, neuromyelitis optica (devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome, and fibromyalgia.

Thus, the invention encompasses a method of treatment or prevention of autoimmune disease and allogeneic graft rejection, which are mediated by abnormal or increased immune response either to a self antigen and/or to a non-self antigen present on the transplanted cells or tissues. Further, by preventing the initial immune response, e.g., by inhibiting serotonin signaling in a cell that mediates the response, the present invention also abrogates any secondary response that might ensue.

Additionally, the present invention encompasses treatment of diseases wherein a secondary immune response has already become established. This is because most, if not all, autoimmune diseases are chronic conditions. Although the etiology of most autoimmune diseases is poorly understood, it is clear that CD4+ memory helper T cells and/or CD8+ memory cytotoxic T cells are involved. These secondary T cells have different cellular markers and behave in a qualitatively different manner than do primary T cells (for review see, Dutton et al., 1998, Ann. Rev. Immunol. 16:201–223). Thus, the invention includes a method of inhibiting activation of an immune cell in a mammal where the activation is mediated by activation of a serotonin type 2 receptor on the cell. The method comprises administering an effective amount of an inhibitor of the interaction of serotonin with a serotonin type 2 receptor. This is because, as demonstrated throughout the specification, inhibition of the interaction of serotonin with a serotonin type 2 receptor on an immune cell (e.g., a T cell) prevents activation of the immune cell, thereby inhibiting an immune response by the cell.

Autoimmune diseases that can be treated according to the methods of the invention include, but are not limited to myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Guilliari-Barre Syndrome, vasculitis, multiple sclerosis, neuromyelitis optica (devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome, and fibromyalgia.

The invention further includes a method of inhibiting a secondary immune response in a mammal. The method comprises administering an effective amount of an inhibitor of the interaction of serotonin with a serotonin type 2 receptor. This is because, as disclosed elsewhere herein, where the interaction of serotonin with a serotonin type 2 receptor is inhibited by, among other things, a serotonin type 2 receptor antagonist, both a primary and a secondary immune response is inhibited. That is, the present invention demonstrates, for the first time, that inhibiting interaction of serotonin with a serotonin type 2 receptor on an immune cell prevents or inhibits an immune response. Thus, the present invention provides novel specific immunomodulation therapies for treatment of a wide plethora of autoimmune diseases and allogeneic graft rejection mediated by T cell activation via interaction of serotonin with a serotonin type 2 receptor.

The skilled artisan would appreciate, based upon the disclosure provided herein, that the invention includes treating a patient with fulminant AIDS. This is because during this final phase of the disease, a patient's CD4 cell counts are very low and the person is generally dying of opportunistic infections. If one looks at the remaining CD4 cells, one finds something highly unusual, i.e., about 50% of the remaining CD4 cells are activated. This is because the human immunodeficiency virus (HIV) requires active proliferation of the T cell in order to undergo its own replication. Based on the data disclosed herein, and without wishing to be bound by any particular theory, the proliferation, even at the end stage of AIDS, likely requires the serotonin signal mediated by a serotonin type 2 receptor. Because, as demonstrated by the cell counts and other data disclosed herein, blocking the 5HT 2C signal apparently induces cell death, then a bolus dose of, e.g., Sansert can be administered to an end stage patient. Thus, by induced apoptosis of activated CD4 cells, the virus reservoir can be effectively eliminated the patient, thereby potentially enabling the regrowth of nor-infected CD4 cell and, thus, achieving recovery.

B. Methods of Identifying Useful Compounds

The invention encompasses methods to identify a compound that inhibits interaction of serotonin with a serotonin family receptor. One skilled in the art would appreciate, based upon the disclosure provided herein, that assessing the level of interaction of serotonin and a serotonin family receptor can be performed by assessing, among other things, activation of a T cell, and the like, when compared to the same parameter (s) in an otherwise identical cell not contacted with the compound. One skilled in the art would understand that such compounds can be useful for inhibiting a disease, disorder, or condition mediated by and/or associated with interaction of serotonin with a serotonin receptor. The skilled artisan would further appreciate, based on the disclosure provided herein, that it may useful to decrease the interaction between serotonin and a serotonin receptor of a specific subtype or subtypes, while leaving the interactions of serotonin with other serotonin receptor types unaffected.

One of skill in the art would understand, based upon the disclosure provided herein, that the invention includes a method of identifying a compound useful for treating an autoimmune disease or allogeneic grafting response in a mammal. The method comprises identifying a substance or compound that inhibits the interaction of serotonin with a serotonin type 1B, 2A, 2B, 2C, 4, and 6 receptor. This is because, as disclosed elsewhere herein, it has been discovered that inhibiting the interaction of serotonin with a serotonin type 1B, 2A, 2B, 2C, 4, and 6 receptor inhibits immune cell activation thereby inhibiting an immune response. Thus, the skilled artisan, armed with the teachings of the invention, would appreciate that a compound that inhibits such interaction is a useful potential therapeutic for treating an autoimmune disease or allogeneic graft response otherwise mediated by the serotonin/receptor interaction.

The method comprises contacting a serotonin type 1B, 2A, 2B, 2C, 4, and 6 receptor with a test compound and comparing the level of binding of serotonin with that serotonin type 1B, 2A, 2B, 2C, 4, and 6 receptor with the level of serotonin binding with an otherwise identical serotonin type 1B, 2A, 2B, 2C, 4, and 6 receptor not contacted with the test compound. The routineer would understand that a lower level of serotonin binding with the receptor contacted with the compound compared with the level of serotonin binding with the otherwise identical serotonin type 1B, 2A, 2B, 2C, 4, and 6 receptor not contacted with the compound is an indication that the compound inhibits the serotonin/receptor interaction and is, therefore, useful for treating an autoimmune disease or an allogeneic graft response in a mammal. The skilled artisan would also appreciate, in view of the disclosure provided herein, that standard binding assays known in the art, or those to be developed in the future, can be used to assess the binding of serotonin with a serotonin type 1B, 2A, 2B, 2C, 4, and 6 receptor in the presence or absence of the test compound to identify a useful compound. Thus, the invention includes any compound identified using this method.

The invention also includes a method for identifying a compound useful for inhibiting activation of a T cell wherein the activation is mediated by serotonin binding with a serotonin type 1B, 2A, 2B, 2C, 4, and 6 receptor on the T cell. More specifically, the method comprises assessing the activation state of a T cell contacted with a test compound and comparing the level of activation of the T cell with the level of activation of an otherwise identical T cell not contacted with the compound. A lower level of activation of the T cell contacted with the compound compared with the level of activation of the otherwise identical T cell not contacted with the compound is an indication that the compound is useful for inhibiting activation of a T cell. This is because the present invention discloses, for the first time, that T cell activation requires serotonin interaction with serotonin type 1B, 2A, 2B, 2C, 4, and 6 receptors on the surface of the T cell such that, when the serotonin/receptor interaction is inhibited, activation is inhibited thereby inhibiting an immune response by the cell. Clearly, as demonstrated elsewhere herein, a compound that inhibits interaction of serotonin with a serotonin type 1B, 2A, 2B, 2C, 4, and 6 receptor on a T cell is an important potential therapeutic compound useful for treatment of autoimmune disease and allograft rejection.

An example of a compound that antagonizes the serotonin family receptor (i.e., a compound that blocks receptor binding) is SB 206553, the structure of which is set forth in Forbes et al., 1993, J. Med. Chem. 36:1104–1107). As presented in the data provided herein, the immune response is effectively inhibited with administration of this antagonist to lymphocytes expressing the receptor. One skilled in the art would appreciate that an antagonist such as SB 206553 would be helpful in mediating the immune response by blocking serotonin family receptor binding in order to treat autoimmune diseases or other diseases in which an enhanced immune response is detrimental to the patient:

It is also understood that the properties of this compound can be altered and improved by modifications to the positions indicated by the variable positions (R) as described by Forbes et al., 1996, J. Med. Chem. 39:4966–4977, and indicated below:

In yet another embodiment of this structure an ether containing derivative has been described by Forbes et al. (1996, J. Med. Chem. 39:4966–4977), that has better potency, but lacks efficacious oral activity. The structure of this derivative is depicted below:

Further, one skilled in the art would appreciate based on the disclosure provided herein that, as disclosed in the examples below, a cell which lacks endogenous serotonin receptor expression can be transfected with a vector comprising an isolated nucleic acid encoding the receptor whereby expression of the receptor is effected in the cell. The transfected cell is then contacted with the test compound thereby allowing the determination of whether the compound affects the interaction with a serotonin receptor. Therefore, one skilled in the art armed with the present invention would be able to, by selectively transfecting a cell lacking detectable levels of the receptor using receptor-expressing vectors, identify a compound which selectively affects serotonin/receptor binding.

In addition, the invention encompasses assays for a compound that inhibits signal transmission via a serotonin receptor where such assays are based on detection of changes in the physical and/or morphological characteristic (s) of a cell. That is, based upon the disclosure provided herein, the skilled artisan would appreciate that inhibition of serotonin signaling mediates or is associated with detectable change in a cell. More particularly, as demonstrated by the data disclosed elsewhere herein, inhibiting a serotonergic signal in a cell mediates an increase in cell size, and/or morphology, and mediates detection of cell characteristics associated with apoptosis, cell death, and/or necrosis. Such changes can be readily detected and quantified using a wide plethora of techniques, including, but not limited to, microscopy (electron, light, and the like), any techniques that assess density, morphology, and the like. And all of these assay methods are included in the present invention, as are methods to be developed in the future.

The method disclosed herein allows rapid screening of substances for their ability to inhibit serotonergic signaling in a cell, which compounds are important potential therapeutics for use in methods where inhibiting serotonergic signaling provides a therapeutic benefit, including, but not limited to, development of compounds useful for treating depression, emesis, and the like, and diseases, disorders or conditions that are not associated with the central nervous system, such as, but not limited to, autoimmune disease, multiple myeloma, obstructive airway disease (e.g., asthma), allogeneic graft rejection, and the like, as more fully set forth elsewhere herein.

C. Methods of Treating or Alleviating a Disease, Disorder or Condition in a Mammal Mediated by Aberrant Serotonin Type 2 Receptor on a T Cell The invention includes a method of alleviating a disease, disorder or condition mediated by aberrant, i.e., malexpression, of a serotonin family receptor. Where the disease, disorder or condition is associated with over- or under-expression of a serotonin receptor, the method comprises administering an antisense nucleic acid complementary to a nucleic acid encoding the appropriate receptor to a patient afflicted with a disease, disorder or condition mediated by increased receptor expression compared to the level of receptor expression in otherwise identical but normal tissue, i.e., tissue which does not exhibit any detectable clinical parameters associated with the disease, disorder or condition being treated or alleviated. This, in turn, mediates a decrease in receptor expression thereby alleviating a disease, disorder or condition mediated by malexpression of receptor. Such diseases, disorders or conditions include, but are not limited to, myasthenia gravis, idiopathic inflammatory myopathy, chronic neutropenia, rheumatoid arthritis, idiopathic thromcytopenia purpura, autoimmune hemolytic syndromes, antiphospholipid antibody syndromes, inflammatory bowel disease, Crohn's disease, ulcerative colitis, myocarditis, Guillian-Barre Syndrome, vasculitis, multiple sclerosis, neuromyelitis optica (devic's syndrome), lymphocytic hypophysitis, Graves disease, Addison's disease, hypoparathroidism, type 1 diabetes, systemic lupus erythematosus, pemphigus vulgaris, bullous pemphigoid, psoriasis, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome, and fibromyalgia.

The skilled artisan would appreciate, based upon the disclosure provided herein, that the present invention includes treating conditions associated with, or mediated by, over expression or under expression, of a 5HT receptor. One skilled in the art would appreciate such treatments include, but are not limited to, treating a patient under expressing, among others, a 5HT type 1A receptor. This is because receptor stimulation causes a decreased cAMP signal that competes with the 5HT type 6 receptor's upregulation signal. Thus, the condition can be treated by decreasing expression of the 5HT type 6 receptor in a cell using, among other things, an antisense to the 5HT 6 receptor to mediate balance between the two receptors' signals, thereby treating the condition of the patient.

Additionally, one skilled in the art would understand, based upon the disclosure provided herein, that the invention encompasses a method of treating a disease mediated by increased or decreased expression of the serotonin family receptor. This is because the data disclosed herein demonstrate that there are certain diseases, disorders, or conditions that are associated with/mediated by increased or decreased levels of serotonin receptor expression. The data disclosed herein demonstrate that, antagonizing expression of a serotonin family receptor with a 5-HT2B/2C-specific antagonist, inhibits the immune response such that lymphocytes do not further proliferate. This inhibition is useful in treatment of autoimmune diseases as well as treatment of other diseases that involve heightened immune response. Thus, decreasing receptor expression or blocking receptor binding can treat conditions associated with or mediated by increased levels of receptor. Therefore, methods of identifying a compound that decreases the level of serotonin family receptor are helpful for treating and/or alleviating diseases, disorders or conditions associated with increased expression of receptor.

Antisense nucleic acids that inhibit expression of a serotonin family receptor can therefore also be used for the manufacture of a medicament for treatment of a disease, disorder or condition mediated by increased expression of receptor when compared with expression of receptor in a cell and/or a patient not afflicted with the disease, disorder or condition.

Techniques for inhibiting expression of a nucleic acid in a cell are well known in the art and encompass such methods as disclosed herein (e.g., inhibition using an antibody, an antisense nucleic acid, a ribozyme, and the like). Other techniques useful for inhibiting expression of a nucleic acid encoding a serotonin family receptor include, but are not limited to, using nucleotide reagents that target specific sequences of the receptor promoter, and the like.

The skilled artisan would understand, based on the disclosure provided herein, that nucleic acid expression of a serotonin type 2 receptor present on activated T cells, can be inhibited or abrogated using a nucleic acid that prevents expression of the nucleic acid encoding the receptor in the cell. As more fully set forth elsewhere herein, once the nucleic and amino acid sequences of a serotonin receptor are known, various methods well-known in the art can be used to inhibit expression of the receptor on the cell surface. Such methods include, but are not limited to, antibodies, ribozymes, and antisense molecules. The design and use of such compounds is well established once the still artisan is armed with the sequence of nucleic acid encoding the receptor therapeutic target and such methods are therefore not recited herein as they are well known in the art. For instance, designing antisense molecules and ribozymes can effectively inhibit T cell activation by inhibiting expression of the serotonin type 2 receptor without affecting expression of other serotonin family receptors which may be required thereby avoiding any deleterious effects of non-specifically inhibiting serotonin interaction with other serotonin receptors that may be required.

Whether expression of the receptor protein, levels of the polypeptide, or its activity, is increased or decreased, one skilled in the art would appreciate, based on this disclosure, that methods of reducing or inducing receptor expression encompass administering a recombinant cell that either expresses or lacks expression of the receptor.

In another embodiment of the invention, an individual suffering from an immunologically-based disease, disorder or a condition that is associated with or mediated by receptor expression can be treated by supplementing, augmenting and/or replacing defective cells with cells that lack receptor expression. The cells can be derived from cells obtained from a normal syngeneic matched donor or cells obtained from the individual to be treated. The cells may be genetically modified to inhibit receptor expression.

In addition to replacing defective cells with repaired cells or normal cells from matched donors, the method of the invention may also be used to facilitate expression of a desired protein that when secreted in the an animal, has a beneficial effect. That is, cells may be isolated, furnished with a gene encoding a serotonin family receptor and introduced into the donor or into a syngeneic matched recipient. Expression of the receptor exerts a therapeutic effect.

This aspect of the invention relates to gene therapy in which therapeutic amounts of a serotonin family receptor are administered to an individual.

According to some aspects of the present invention, recombinant cells transfected with either nucleic acid encoding a serotonin family receptor, antisense nucleic acids or a knock-out targeting vector of the invention, can be used as cell therapeutics to treat a disease, disorder or a condition characterized by expression of a serotonin family receptor or the lack thereof.

According to the present invention, gene constructs comprising nucleotide sequences of the invention are introduced into cells. That is, the cells, referred to herein as "recombinant cells," are genetically altered to introduce a nucleic acid encoding a serotonin family receptor or a nucleic acid that inhibits such receptor expression by the recombinant cell thereby mediating a beneficial effect on an recipient to which the recombinant cell is administered. According to some aspects of the invention, cells obtained from the same individual to be treated or from another individual, or from a non-human animal, can be genetically altered to replace a defective gene and/or to introduce a gene whose expression has a beneficial effect on the individual or to inhibit receptor expression which can have a beneficial effect on the individual.

In some aspects of the invention, an individual suffering from a disease, disorder or a condition can be treated by supplementing, augmenting and/or replacing defective or deficient nucleic acid encoding a serotonin family receptor by providing an isolated recombinant cell containing gene constructs that include normal, functioning copies of a nucleic acid encoding a serotonin receptor. This aspect of the invention relates to gene therapy in which the individual is provided with a nucleic encoding a serotonin family receptor for which they are deficient in presence and/or function. The isolated nucleic acid encoding a serotonin family receptor provided by the cell compensates for the defective receptor expression of the individual, because, when the nucleic acid is expressed in the individual, a protein is produced which serves to alleviate or otherwise treat the disease, disorder or condition in the individual.

In all cases in which a gene construct encoding a serotonin family receptor is transfected into a cell, the nucleic acid is operably linked to an appropriate promoter/regulatory sequence which is required to achieve expression of the nucleic acid in the recombinant cell. Such promoter/regulatory sequences include but are not limited to, constitutive and inducible and/or tissue specific and differentiation specific promoters, and are discussed elsewhere herein. Constitutive promoters include, but are not limited to, the cytomegalovirus immediate early promoter and the Rous sarcoma virus promoter. In addition, housekeeping promoters such as those which regulate expression of housekeeping genes may also be used. Other promoters include those which are preferentially expressed in cells of the central nervous system, such as, but not limited the promoter for the gene encoding glial fibrillary acidic protein. In addition, promoter/regulatory elements may be selected such that gene expression is inducible. For example, a tetracycline inducible promoter may be used (Freundlich et al., 1997, Meth. Enzymol. 283:159–173).

The gene construct is preferably provided as an expression vector which includes the coding sequence of a serotonin family receptor of the invention operably linked to essential promoter/regulatory sequences such that when the vector is transfected into the cell, the coding sequence is expressed by the cell. The coding sequence is operably linked to the promoter/regulatory elements necessary for expression of the sequence in the cells. The nucleotide sequence that encodes the protein may be cDNA, genomic DNA, synthesized DNA or a hybrid thereof or an RNA molecule such as mRNA.

The gene construct, which includes the nucleotide sequence encoding a receptor operably linked to the promoter/regulatory elements, may remain present in the cell as a functioning episomal molecule or it may integrate into the chromosomal DNA of the cell. Genetic material may be introduced into cells where it remains as separate genetic material in the form of a plasmid. Alternatively, linear DNA which can integrate into a host cell chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

In order for genetic material in an expression vector to be expressed, the promoter/regulatory elements must be operably linked to the nucleotide sequence that encodes the protein. In order to maximize protein production, promoter/regulatory sequences may be selected which are well suited for gene expression in the desired cells. Moreover, codons may be selected which are most efficiently transcribed in the cell. One having ordinary skill in the art can produce recombinant genetic material as expression vectors which are functional in the desired cells.

In addition to providing cells with recombinant genetic material that either corrects a genetic defect in the cells, that encodes a protein which is otherwise not present in sufficient quantities and/or functional condition so that the genetic material corrects a genetic defect in the individual, and/or that encodes a protein which is useful as beneficial in the treatment or prevention of a particular disease, disorder or condition associated therewith, and that inhibits expression of a serotonin receptor on the cell (e.g., a knock-out targeting vector, an antisense nucleic acid, and the like), genetic material can also be introduced into the recombinant cells used in the present invention to provide a means for selectively terminating such cells should such termination become desirable. Such means for targeting recombinant cells for destruction may be introduced into recombinant cells.

According to the invention, recombinant cells can be furnished with genetic material which renders them specifically susceptible to destruction. For example, recombinant cells may be provided with a gene that encodes a receptor that can be specifically targeted with a cytotoxic agent. An expressible form of a gene that can be used to induce selective cell death can be introduced into the recombinant cells. In such a system, cells expressing the protein encoded by the gene are susceptible to targeted killing under specific conditions or in, the presence or absence of specific agents. For example, an expressible form of a herpesvirus thymidine kinase (herpes tk) gene can be introduced into the recombinant cells and used to induce selective cell death. When the introduced genetic material that includes the herpes tk gene is introduced into the individual, herpes tk will be produced. If it is desirable or necessary to kill the implanted recombinant cells, the drug gangcyclovir can be administered to the individual which will cause the selective killing of any cell producing herpes tk. Thus, a system can be provided which allows for the selective destruction of implanted recombinant cells.

One skilled in the art would understand, based upon the disclosure provided herein, that the present invention encompasses production of recombinant cells to either provide a serotonin family receptor to or inhibit receptor expression in a mammal. That is, the cells can be used to administer a receptor protein to an animal or to deliver a molecule (e.g., a knock-out targeting vector, an antisense nucleic acid, a ribozyme, and antibody that specifically binds with the receptor, and the like).

The invention further includes using recombinant cells expressing a receptor of interest, as a target for screening for new serotonin receptor agonists, inverse agonists and antagonists that can be used to treat immunologically related disorders. Thus, the cell can be contacted with a test compound and the activation of the cell can be compared to the activation of an otherwise identical cell not contacted with the compound. A higher or lower level of activation of the cell contacted with the compound compared with the activation of the cell not contacted with the compound, is an indication that the compound affects a serotonin-receptor mediated activation and is therefore a potential serotonin receptor agonist, inverse agonist and/or antagonist that can be used to treat immunologically related disorders.

Administration of a serotonin family receptor to an animal can be used as a model system to study the mechanism of action of serotonin or other ligands of the receptor or to develop model systems useful for the development of diagnostics and/or therapeutics for diseases, disorders or conditions associated with receptor expression.

Further, the delivery of a serotonin receptor to an animal mediated by administration of recombinant cells expressing a serotonin family receptor can also be used to treat or alleviate a disease, disorder or condition where increasing the level of a serotonin receptor mediates a therapeutic effect.

Alternatively, administration of recombinant cells comprising a nucleic acid the expression of which inhibits or reduces serotonin receptor expression, activity, and/or secretion from a cell, can be used as a model for the development of diagnostics and/or therapeutics useful for diseases, disorders or conditions associated with or mediated by receptor expression, activity, and/or secretion. The present invention encompasses that the recombinant cells can produce the molecule that inhibits receptor expression thereby providing such molecule to the animal. Alternatively, without wishing to be bound by any particular theory, the recombinant cells themselves, which are otherwise functional cells, except for the inability to express the receptor, can perform the functions of otherwise identical but non-recombinant cells, without being subject to the serotonin signaling pathway.

Cells, both obtained from an animal, from established cell lines that are commercially available or to be developed, or primary cells cultured in vitro, can be transfected using well known techniques readily available to those having ordinary skill in the art. Thus, the present invention is not limited to obtaining cells from a donor animal or from the patient animal itself. Rather, the invention includes using any cell that can be engineered using a nucleic acid of the invention such that the recombinant cell either expresses a serotonin receptor or the recombinant cell does not express such a receptor or expresses it at a lower level.

Nucleic acids can be introduced into the cells using standard methods which are employed for introducing a gene construct into cells which express the protein encoded by the gene or which express a molecule that inhibits serotonin receptor expression. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

Where an isolated receptor polypeptide, an antibody that specifically binds with the receptor, an antisense nucleic acid to the receptor, and/or recombinant cells of the invention are administered to an animal either to increase or reduce the level of receptor present in the animal, one skilled in the art would understand, based upon the disclosure provided herein, that the amount of the polypeptide, nucleic acid, antibody, or cell to be administered to the animal can be titrated by assessing the expression level of receptor or the level of receptor polypeptide or nucleic acid encoding the receptor present in the tissues of the animal.

Methods for assessing the level of receptor expression (e.g., using anti-receptor antibodies in Western blot or other immune-based analyses such as ELISA) and/or methods for assessing the level of receptor expression in a cell and/or tissues (e.g., using Northern blot analysis, and the like) are disclosed herein or are well known to those skilled in the art. Such assays can be used to determine the "effective amount" of receptor polypeptide, nucleic acid, antibody, antisense nucleic acid, ribozyme, recombinant cell, and the like, to be administered to the animal in order to reduce or increase the level of receptor expression.

D. Methods of Relating to Inhibiting Signal Transmission via a Serotonin Receptor The invention includes a method of affecting a cell cycle process by inhibiting transmission of a serotonin signal via a serotonin receptor. That is, the skilled artisan would appreciate, based upon the disclosure provided herein, that removal, or inhibition, of a serotonin signal transmitted via a 5-HT receptor affects a cell cycle process. This is because the data disclosed herein amply demonstrate that inhibition of a serotonergic signal has profound effects on a cell that is cycling through the cell cycle, e.g., removal of the signal mediates rapid cell death via apoptosis (i.e., the cells become stained by annexin demonstrating exposure of PI on the cell surface, DNA fragmentation is detected, and the cells increase in size and exhibit an altered morphology, and the like). These are surprising results since previous studies have focused on inhibiting a serotonergic signal in a non-dividing cell that was not going through the cell cycle, i.e., neural or muscle cells, for treatment of various neurological disorders. Without wishing to be bound by any particular theory, the fact that prior art studies relating to use of various inhibitors of serotonin signaling comprised contacting non-dividing cells that were not passing through the cell cycle, such as, but not limited to, neurons, the effect of withdrawal and/or inhibition of serotonin signaling upon the cell cycle was not, and indeed, could not have been, observed, appreciated, or understood. Thus, the data disclosed herein demonstrate, for the first time, a novel method for affecting the cell cycle via inhibition of a serotonin receptor.

The skilled artisan would understand, based upon the disclosure provided herein, that certain cells comprise a serotonin receptor and that signaling via such receptor is crucial in the cell progressing through the cell cycle. Thus, the invention includes a method of affecting the cell cycle process by inhibiting transmission of a serotonergic signal via that receptor. The skilled artisan would further understand that a wide plethora of compounds are available that can be used to inhibit transmission of a serotonergic signal, such as, but not limited to, the antagonists discussed elsewhere herein. Further, the invention includes such compounds as are developed in the future, which inhibit transmission of a serotonergic signal mediated via a serotonin receptor.

The method further comprises identifying the presence of a serotonin receptor on a cell of interest if the cell is not known to express one, and further characterizing such receptor to assess which compound(s) inhibit signaling via that receptor. Methods of assessing the presence or absence of a serotonin receptor on a cell, as well as methods for identifying a compound that inhibits signaling via that receptor, using pharmacological, recombinant, or other methodologies, are well know in the art and are exemplified elsewhere herein. The invention also encompasses such methods as are developed in the future for identifying the presence of a serotonin receptor on a cell and which compound(s) affect signaling via the receptor of interest.

The invention also includes a method of affecting apoptosis in a cell. The method comprises inhibiting transmission of a signal otherwise transmitted via a serotonin receptor on the cell. This is because the data disclosed elsewhere herein demonstrate that inhibition of a serotonergic signal in a cell that is progressing through the cell cycle, e.g., proliferating and dividing, mediates apoptosis in that cell. Thus, the skilled artisan would appreciate, based upon the disclosure provided herein, that inhibiting transmission of a signal via a 5-HT receptor provides a novel method for inducing apoptosis.

The methods of the invention are useful in that they allow, for the first time, selective apoptosis of growing cells without affecting nearby cells that are either not dividing or which have no, or a different serotonin receptor, on the surface. That is, the method of the invention does not affect a cell that either is not progressing through the cell cycle process or which does not express the same type of serotonin receptor on its surface as the target cell. This is especially true in that there are 14 distinct serotonin receptors, comprising 7 different subtypes based on their pharmacological specificity for various compounds that agonize or antagonize signaling via the receptor. Therefore, once the serotonin receptor present on the cell of interest has been identified and characterized, the skilled artisan would understand, based upon the surprising data disclosed elsewhere herein, that apoptosis of the cell can be induced by selectively inhibiting the serotonergic signaling in that target cell, without affecting any serotonergic signaling in other cells which either do not possess a serotonergic receptor or which express a receptor of a different pharmacological subtype as the target cell such that signaling via that receptor is not affected by the compound used to induce apoptosis in the cell of interest.

The skilled artisan would also appreciate, based upon the disclosure provided herein, that the present invention encompasses a method of inducing apoptosis in a cell. This is because, as discussed previously elsewhere herein, serotonin signaling has been demonstrated, for the first time, to be required for progress of a cell through the cell cycle such that inhibition of the signal can mediate apoptosis in a cell. More specifically, inhibition of serotonin binding with a serotonin type 1B, 2, 4, and/or 6 receptor on a cell requiring serotonin signaling, has been demonstrated to mediate cell death via traditional apoptosis pathways.

Further, the skilled artisan would appreciate, based upon the disclosure provided herein, that the invention encompasses a method of inducing cell death. That is, the data disclosed herein demonstrate that inhibition of serotonin signaling in a cell that expresses a serotonin type 1B, 2, 4 or 6 receptor mediates death of the cell. Thus, based upon the disclosure provided herein, the skilled artisan would understand that a method of inducing cell death comprising inhibiting serotonin binding with a serotonin (type 1B, 2A, 2B, 2C, 4, or 6) receptor is encompassed by the invention.

II. Kits

The invention encompasses various kits relating to inhibiting the interaction of serotonin with a serotonin type 2 receptor because, as disclosed elsewhere herein, inhibiting this interaction in turn inhibits activation of an immune cell thereby inhibiting an immune response. Thus, in one aspect, the invention includes a kit for modulating an immune response in a mammal. The kit comprises an effective amount of an inhibitor of the interaction of serotonin with a serotonin type 2 receptor. Such an inhibitor includes, preferably, a serotonin type 2 receptor antagonist. And the kit further comprises an applicator and an instructional material for the use thereof.

The skilled artisan would appreciate, based upon the disclosure provided herein, that the invention encompasses a kit useful for inhibiting a type 2 receptor-mediated signal associated with administration of an adenoviral vector for use of adenoviral vector-based approaches to gene therapy in mammals. That is because although the most efficient vector for delivering a gene is the adenoviral vector, the body makes an immune response to the vector, which limits its usefulness in gene delivery vector, and leads to loss of expression. Consequently, within several weeks, every cell that has received the new vector (and the comprised therein) is eliminated, rendering the technique ineffective. The data disclosed herein suggest that administration of a type 2 inverse agonist/antagonist to coincide with the adeno-associated immune response can effectively eliminate the responsive cells, abrogate the immune response directed against the vector, and thereby enable the gene therapy.

The invention includes various kits which comprise a compound, such as a nucleic acid encoding a serotonin family receptor, an antibody that specifically binds such a receptor as well as a nucleic acid encoding such antibody, a nucleic acid complementary to a nucleic acid encoding such a receptor but in an antisense orientation with respect to transcription, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for alleviating a disease mediated by malexpression of a serotonin family receptor. The kit is used pursuant to the methods disclosed in the invention. Briefly, the kit may be used to contact a cell with a nucleic acid complementary to a nucleic acid encoding a serotonin receptor where the nucleic acid is in an antisense orientation with respect to transcription to reduce expression of the receptor, or with an antibody that specifically binds with such receptor or a nucleic acid encoding the antibody, wherein the decreased expression, amount, or activity of the receptor mediates a beneficial effect. Moreover, the kit comprises an applicator and an instructional material for the use of the kit. These instructions simply embody the examples provided herein.

The kit includes a pharmaceutically-acceptable carrier. The composition is provided in an appropriate amount as set forth elsewhere herein. Further, the route of administration and the frequency of administration are as previously set forth elsewhere herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

Serotonin Receptors and Immunomodulation

Tryptophan is one of the ten essential amino acids required for building new proteins in the cell. It is possible, though not likely, that the catabolism of Tryptophan results in starvation and, therefore, accounts for the observed T cell inhibition. However, none of the other nine essential amino acids have been implicated in the control of T cell responses.

Figure 1:
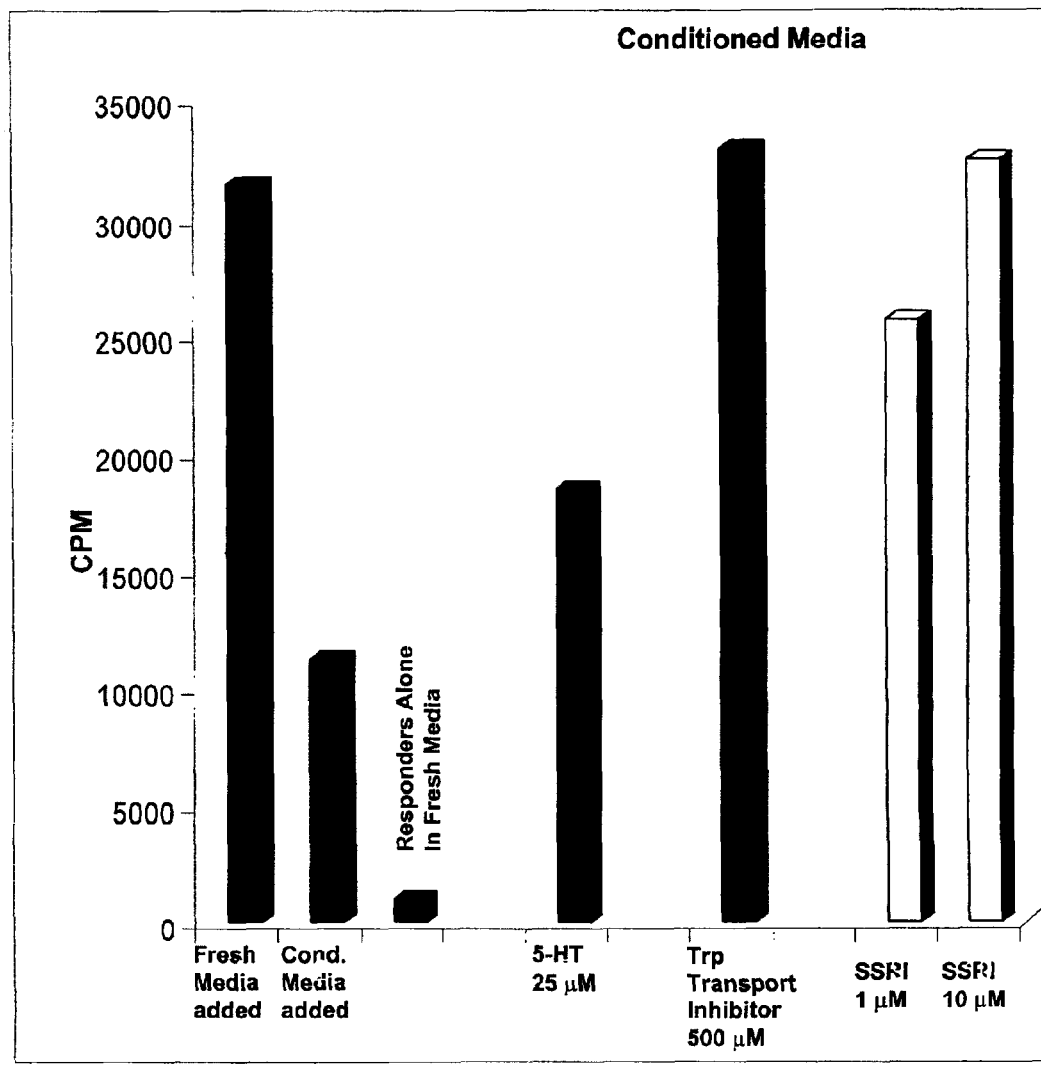
FIG. 1 is a diagram depicting the effects of macrophage-conditioned media on the proliferation response of lymphocytes to a mitogenic activation signal.

It is generally known that tryptophan has two metabolic fates. In one pathway, tryptophan is converted to niacin. At best, tryptophan only accounts for 50% of the niacin used in a cell (the bulk coming from dietary supplements, thus it is not rate-limiting). The other metabolic fate of tryptophan is its conversion to 5-hydroxytryptamine (5-HT), also known as serotonin (see FIG. 1). This, on the other hand, is the only known source for serotonin. Serotonin is, arguably, the most widely studied biologically active compound of all time. To date, the role of serotonin in the mounting of an immune response is poorly understood, if at all. In fact, the five (5) major university-level textbooks that serve as standard treatises for teaching undergraduate and graduate immunology courses only mention serotonin in the context of platelets and its ability to induce vasoconstriction at the site of a wound or mention the fact that it is contained in rodent mast cells (Sharon, 1998, In: Basic Immunology, Williams and Wilkins, Baltimore, Md.; Kugy, 1997, In: Immunology, W. H. Freeman & Go; Abbas et al., 1997, In: Cellular and Molecular Immunology, W. B. Saunders; Janeway & Travers, In: Immnobiology—the immune system in health and disease, Garland Publishing, Inc.; Roitt et al., 1998, In: Immunology, Mosby, London).

In terms of embryonic development, all lymphocytes are derived from the neural crest. Without wishing to be bound by any particular theory, the earliest, primordial immunologic defenses may have been based on the "nerve impulse" paradigm and, consequently, controlled by serotonin. With time, nature has imposed many elegant and intricate layers of regulation upon this basic pathway. Without wishing to be bound by any particular theory, the data disclosed herein demonstrate that the effects of tryptophan related to IDO catabolism are, in fact, due to its effect on the serotonin pathway. A review of the medically related literature produced over the last 40 years reveals that although there are scattered reports that serotonin may affect some T cell activities, no study to date has, until the present invention, ever identified serotonin receptor activation as a basal, rate-limiting requirement for mounting T cell responses.

The data disclosed demonstrate the fundamental role of 5-HT in the coordination and absolute control of a T cell-mediated immune response. In the studies disclosed herein, either human primary peripheral blood lymphocytes that have been purified away from the adherent cell populations or murine splenocytes, also separated from the adherent cells, were used. Thus, a semi-purified population of (CD3-positive) T cells was obtained and the cells were subsequently activated by the addition of a mitogen, e.g., either phytohaemagglutinin (PHA) or Conconavalin A (ConA). These plant lectins were used as mitogens because they act by cross-linking the T cell surface receptors involved in both the primary and secondary activation signals, thereby eliciting a very powerful stimulating signal. Therefore, one skilled in the art would appreciate, based on the disclosure provided herein, that if a T cell response to these lectins can be modulated, the principles are readily applicable to other immunogens.

As pointed out previously elsewhere herein, under some circumstances, 5-HT has been shown to stimulate the activated T cells (Kut et al., 1992, Immunopharmacol. Immunotoxicol. 14:783–796; Young et al., 1993, Immunology 80:395–400), whereas most laboratories report that high concentrations of added 5-HT inhibit the proliferation (Mossner & Lesch, 1998, Brain, Behavior and Immunity 12:249–271). To explore this apparent dichotomy, the influence of both tryptophan and 5-HT on the basic activation pathway of T cells was assessed.

Supplies and Reagents

The following compounds were obtained from Sigma-Aldrich (St. Louis, Mo.): tryptophan, 5-hydroxy-tryptophan, serotonin-hydrochloride, phenelzine, 2-amino-2-norbornanecarboxylic acid (BCH), L-p-chlorophenylalanine, fluoxetine, m-hydroxybenzylhydrazine dihydrochloride (NSD-1015), (S)-Propranolol, (S)- and (R )-8-OH DPAT-hydrobromide, WAY 100635, LY 53857, SB 206553, SB 242084, methysergide-maleate, 2-methyl-5-HT, Ro046790, risperidone, 3-tropanyl-indole-3-carboxylate, clozapine, ketanserin, mianserin, SDZ 205557, alpha-methyl-DL-tryrosine-methyl ester hydrochloride.

The following compounds were obtained from Tocris Cookson (St. Louis, Mo.): MDL 11,939. Stock solutions were typically made at 1 mM concentration, in Hanks Balanced Salt Solution (HBSS). Exceptions were Risperidone and MDL 11,939, which first were solubilized in hydrochloric acid (approximately 1/10 of the final volume), then diluted with HBSS and titrated with sodium hydroxide to a nearly neutral pH. L-p-Chlorophenylalanine was prepared at 5 mM concentration, in RPMI with 10% FBS in order to reach maximal concentrations allowed by its solubility.

RPMI medium was from Gibco BRL, HBSS, fetal bovine serum (FBS), human A/B serum, Histopaque-1077, M-CSF, Concavalin A (ConA), fluoxetine, and BCH [2-Amino-2norbornan carboxylic acid] were from Sigma Chemical Co. (St. Louis, Mo.). All disposable plastic ware was from Coming Costar (Coming Inc. Life Sciences, Acton, Mass.). Tritiated thymidine was obtained from DuPont-NEN (Lincoln Park, N.J.). Vacutainer collection sets and heparinized collection vials were from Becton-Dickinson (Franklin Lakes, N.J.). All cells were grown at 37° C., in 5% $CO_2$, unless indicated otherwise.

Animals

BALB/c/BYJ (H-2$^d$) and C57/B6J mice (H-2$^b$) 6–8 weeks old were obtained from Jackson Laboratories (Bar Harbor, Me.).

PCR Primers

Sequencing primers were: T7 TAATACGACTCACTATAGGG (SEQ ID NO:15), Bgh TAGAAGGCACAGTCGAGG (SEQ ID NO:16). Primers used for specific 5-HT receptor amplifications were are follows: 1A receptor: 1af CGGTCAAAAAGGTGGAGAAG (SEQ ID NO:17), 1ar GAGGCAAGTGCTCTTTGGAG (SEQ ID NO:18), expected product size is 234 bp. 2A receptor: 2ar AGTCCTCCTGCCTGTGTAGG (SEQ ID NO:19), 2af CGCCGATGATAACTTTGTCC (SEQ ID NO:20), expected product size is 247 bp. 2B receptor: 2bf ACTGGCTGCCTTCTTCACAC (SEQ ID NO:21), 2br TGTCCTTTCGAGAACCATCC (SEQ ID NO:22), expected product size is 206 bp. 2C receptor: 2cf ATGGTGAACCTGAGGAATGC (SEQ ID NO:23), 2cr TTCCATGCTTACTGCCATGA (SEQ ID NO:24), expected product size is 256 bp. 3A receptor: 3af CAATGAGTTCGTGGATGTGG (SEQ ID NO:25), 3ar TGACCACATAGAAGAGGGGC (SEQ ID NO:26), expected product size is 216 bp. 3B receptor: 3bf ACACCGTCTTCAGGGTCAAC (SEQ ID NO:27), 3br GCTCTCCATACAGCGAGGAC (SEQ ID NO:28), expected product size is 270 bp. Receptor 4: 4f GAGACCAAAGCAGCCAAGAC (SEQ ID NO:29), 4r TTGTGGTTGAACAAGGGACA (SEQ ID NO:30), expected product size is 289 bp. All primers were made by Sigma-Genosys (The Woodland, Tex.).

Reverse Transcription and PCR

Whole blood from the healthy donor was fractionated using Ficoll gradient as described in Current Protocols in Immunology. The peripheral blood lymphocytes were collected and plated onto six-well-plates at 2×10$^7$ cells per well. Cells were allowed to adhere to the plastic for 1.5 hours, when the suspension cells were removed and re-plated onto fresh six-well-plates plates at 10$^7$ cells per well. Both adherent and suspension cells were either stimulated with ConA (at 5 μg/ml) or left untreated. 48 hours after ConA stimulation, the cells were harvested and total RNA was extracted using Qiagen RNAeasy miniprep system according to the manufacturer's instructions (Quiagen, Chatsworth, Calif.). (Quiagen, Chatsworth, Calif.) RNA samples were quantitated by ethidium bromide (EtBr) staining of the gel and approximately one μg of each RNA sample was used for the cDNA synthesis. cDNA synthesis was performed with Qiagen Reverse Transcription kit according to the manufacturer's instructions, using either oligoT$_{12-18}$ primer or receptor-specific reverse primers. The resulting cDNA was used as a template in 35 cycles PCR reaction (using Taq DNA polymerase from Sigma) using 5-HT receptor specific primers. For 50 microliters PCR reaction, 25 picomoles of each specific primer was used. PCR conditions were: 95° C. for 45 seconds, 61.5° C. for 45 seconds, 72° C. for 45 seconds. 35 PCR cycles were followed by a 10 minute extension step at 72° C. Final PCR products were analyzed using agarose gel electrophoresis (TAE buffer) (NuSieve 3:1 precast agarose gels from BMA, Rockland, Me.).

For sequence verification, the PCR products were directly cloned into TA expression vector (pCR3.1) (Invitrogene, Carlstad, Calif.) as recommended in the manufacturer's instructions. After the TOP10F' cells were transformed with the PCR product containing litigation mixtures, bacterial cells were plated on agar plates with 25 microgram/ml ampicillin. The next day, bacterial clones were screened for the insert presence by a quick-PCR-based screening approach. This approach allows the screening of several hundred clones per day.

Briefly, the bacterial clones were touched with a 200 microliter pipe tips, the tips were then dipped into 50 microliters of sterile water and boiled for 5 minutes at 95° C. The 25 microliters of the boiled samples were used as a template for the 35 cycles of PCR reaction using the T7 and Bgh plasmid primers (see sequencing primers). The PCR products were then resolved on a 2% agarose gel in TAE buffer. Positive clones were identified and plasmid mini-preps were performed only on selected clones (using Qiagen plasmid mini-prep system, according to the manufacturer's instructions). The plasmids, obtained from the mini preps, were sequenced in the sequencing facility of the University of Pennsylvania using forward (T7) and backward (Bgh) plasmid primers.

Macrophage Media-Conditioning Study

Monocytes obtained from C57/B6J mice were isolated using a protocol modified from Current Protocols in Immunology (1999, Section 14.1.3–14.1.6; Coligan et al., eds., 1994–1997, In: Current Protocols in Immunology, vol. 1–3, John Wiley & Sons Inc.). Femur and tibia bones were harvested from the hind limbs of 6–8 week old C57/B6J mice (Jackson Laboratories, Bar Harbor, Me.). The distal ends of the bones were removed, exposing the marrow plugs. Using a 22 gauge needle (Becton-Dickinson, Lincoln Park, N.J.), the marrow cavities were flushed with RPMI medium supplemented 2% FBS. The cell suspension was then passed through a nylon mesh to remove stromal cells. Red blood cells were lysed using ACK (ammonium chloride potassium lysis buffer; 0.15 M NH$_4$Cl, 10 mM KHCO$_3$, 0.1 mM EDTA) buffer as described in Current Protocols in Immunology (Section 3.1.5).

Cells were resuspended at 10$^7$ cells/ml in RPMI medium, containing 10% FBS, 500 units/ml of murine M-CSF, and 3 ml/well of cell suspension were plated onto a 6 well flat-bottom plate. After 24 hours, the non-adherent cells (monocytes) were harvested and plated at 0.4 million cells per well onto 24 well flat-bottom plate, in 0.65 ml RPMI supplemented with 200 units/ml M-CSF and 15% FBS. Cells were grown for 4 days. Spleens of 6–8 week old BALB/c/BYJ were harvested, and single cell suspension was made. Red blood cells were removed as described above. Adherent cells were removed by 1.5 hour incubation on a nylon wool column, and suspension cells were collected. The BALB/c cells were then plated over the C57/B6 cells (see supra), at 1.2×10$^6$ cells/well, in 0.65 ml (bringing brought the final volume of each well to 1.3 ml). The cells were grown for 2.5 days. When appropriate, fluoxetine or BCH were added at the beginning of this incubation. The medium from the mixed cell cultures was harvested, centrifuged at 1200 RPM to remove cells, and filtered using a 0.22 microns syringe filter (Corning). This filtered medium was used to support another round of cell proliferation.

Purification of Murine T Cells

Spleens were harvested from BALB/c or C57/Black6 mice (Jackson Laboratories). The spleens were mashed in the spin medium (RPMI 1640 Medium (GibcoBRL) supplemented with 2% fetal bovine serum (Sigma), 1% penicillin and streptomycin (Pen-Strep; Sigma Chemical Co., St. Louis, Mo.) and 1% L-Glu (glutamic acid; BioWhittaker)) to obtain a single-cell suspension. The cells were centrifuged for 10 minutes at 1200 RPM, and the supernatants were removed. Red blood cells (RBC's) were lysed with ACK buffer (as described by Colligan et al., 1999, In: Current Protocols in Immunology, Section 3.1.3–3.1.5).

The remaining cells were resuspended in the spin medium, and loaded onto a nylon wool column to remove the adherent cells. The cells were incubated on the column (5% $CO_2$, 37° C.) for approximately 2 hours. The non-adherent cells were washed from the column using spin medium. The cells were centrifuged, and were resuspended in Sensitization medium (RPMI 1640 Medium supplemented with 10% bovine serum, 1% Pen-Strep and 1% L-Glu, beta-MKE.

Murine Mitogenic Stimulation

Primary spleen T-cells from 6–8 week old BALB/c/BYJ mice were obtained as described in Current Protocols in Immunology (1999, Section 3.1.5, and 3.12.2–3.12.4). All drugs were pre-plated on 96 well U-bottom plates at various concentrations, before the addition of the cell suspension. All experimental conditions were assayed in at least triplicate. Purified primary cells were plated in wells comprising drugs at 100,000 cells per well. ConA was added to the cell suspension, to a final concentration of 1 µg/ml, unless otherwise indicated. The total volume was 200 µl per well. Control samples received no ConA stimulation. The cells were allowed to grow for 60 hours. 1 µCi of tritiated thymidine was added to each well, and the plates were harvested 12 hours later using a semiautomatic PHD (Brandel, Gaithersburg, Md.) harvester, 72 hours after the addition of ConA.

Murine Mixed Lymphocyte Reaction (MLR)

MLRs were performed essentially as described in Current Protocols in Immunology (1999, Section 3.12.6–3.12.7). That is, the primary spleen cells obtained from C57/B6J mice were used as stimulators. They were purified as described in Current Protocols in Immunology (1999, Section 3.1.5), and were irradiated (35 Gy) at the Hahnemann Hospital (Philadelphia, Pa.) blood bank facility. Primary spleen cells obtained from BALB/c/BYJ were depleted from the adherent cells using a nylon wool column, and were used as responders.

The various inhibitors were pre-plated onto 96 well, U-bottom plates and all experimental conditions were assayed at least in triplicate. 100,000 C57/B6 cells in RPMI medium, supplemented with 10% FBS, were plated into each well. 200,000 of BALB/c/BYJ cells were plated over the stimulator cells, to a final volume of 200 µl/well. Background controls received either no BALB/c cells, or no C57/B6 cells. One micro Ci of tritiated thymidine was added to each well after 4 days, and the plates were harvested 12 hours later.

Purification of Human T Cells

Blood was obtained from various healthy donors after filling all necessary informed concern from peripheral blood mononuclear cells (PBMS) were isolated using a Ficoll-Hypaque (Sigma) gradient according to standard methods. The cells were collected from the ficoll-serum interface and washed extensively to remove the residual ficoll. The cells were washed and then were resuspended in spin medium (RPMI 1640 Medium supplemented with 2% fetal bovine serum, 1% pen-strep, and 1% L-Glu). The cells were incubated at 37° C., 5% $CO_2$ in a flask for approximately 4 hours to remove adherent cells. The suspension cells were collected and resuspended in sensitization medium (RPMI 1640 Medium supplemented with 10% human serum (Sigma), 1% pen-strep, and 1% L-Glu and -MKE).

Procedures for the Microscopic Staining of the Multiple Myeloma Cells
Drug Treatments $2.0 \times 10^5$ RPMI-8226 cells were cultured, in 6-well culture plates, in the presence of the indicated drug concentrations, in a total of 5 mL RPMI-1640 supplemented with 10% FBS. Each well was harvested in its entirety and divided into two identical samples for cytospins.

Cytospins $1.0 \times 10^5$ RPMI-8226 cells from each treatment group were loaded into Cyto-funnels and centrifuged at 500 rpm for 4 minutes with medium acceleration. Slides were then fixed through graded methanol in PBS (100%, 5 minutes; 80%, 5 minutes; 50%, 5 minutes), washed for 5 minutes in PBS and stored in PBS at 4° C. until stained.

Histochemistry

Cytospun slides were stained with Hematoxylin and Eosin, followed by the nuclear stain, bis-benzamide, rinsed and mounted according to standard staining protocols. Slides were visualized under both brightfield and fluorescent light to generate matched images of the same slide field (see, e.g., FIGS. 28 and 29).

Human Mitogenic Stimulation

Blood from healthy volunteers was drawn using venipuncture, using Vacutainer collection sets and heparinized collection vials. The blood was diluted 1:1 using HBSS to a total volume of 30 ml in 50 ml conical tubes (Fisher Scientific, Co., Pittsburgh, Pa.). To isolate mononuclear cells, 10.5 ml of Histopaque-1077 was layered beneath the 30/ml blood solution, and the tubes were spun at 1200 RPM for 45 minutes at room temperature. Cells from the buffy coats were collected and the residual Histopaque was washed away using repeated centrifugations in HBSS. After washes, cells were resuspended at 5 million cells per ml in RPMI, supplemented with 2% FBS. To remove adherent cells, the suspension was plated onto a 6 well flat-bottom plate (Corning Costar), 3 ml/well, and incubated for 2 hours at 37° C., 5% $CO_2$. Non-adherent cells were harvested after this incubation, were counted and resuspended in RPMI supplemented with 10% human serum (Sigma).

Mitogenic stimulation was performed essentially as described in Current Protocols in Immunology (Section 3.12.2–3.12.4). All drugs were pre-plated before the cell suspension was added onto each well of a 96-well round-bottom plate. All experimental conditions were assayed in at least triplicate. Cells suspended in RPMI supplemented with 10% human serum were plated at 100,000 cells per well to a final volume of 200 µl. ConA was added to a final concentration of 1 g/ml. Control samples received no ConA stimulation. The plates were incubated at 37° C. and 5% $CO_2$. One microCurie of tritiated thymidine was added to each well after 60 hours, and the plates were harvested 12 hours later.

Protocol For Human Mixed Lymphocyte Reaction

Blood from two healthy, non-related, donors was taken as described above. Peripheral blood mononuclear cells were isolated as described previously elsewhere. The adherent cells were separated from the suspension cells as described previously for both donors. Suspension cells from both donors (donors A and B) were used as responders. The remaining adherent cells from each of the donors were used as stimulators against a different donor (suspension A against adherent B and adherent A against suspension B). The stimulator cells were irradiated at 35 Gy. Drugs were pre-plated onto 96 well, U-bottom plates in triplicate. 200,000 "stimulator" cells in RPMI supplemented with 10% human serum were then plated in each well. 200,000

"responder" cells in the same medium were then plated over stimulators to a final volume of 200 μl/well. Background controls received either no stimulator cells, or no responder cells. The plates were incubated at 37° C. and 5% $CO_2$. 1 μCi of tritiated thymidine was added to each well after 4.5 days, and the plates were harvested 12 hours later.

Murine Allograft Model

The in vivo validation screen used was an art-recognized murine allogeneic rejection model as described in Zhan et al., 2000. For this assay, a complete MHC miss-match system was employed wherein $5 \times 10^6$ P815 cells ([H-$2^d$] DBA/2 mastocytoma) were injected into the peritoneal cavity of C57BL/6J (H-$2^b$) mice on day 0 of the experiment. These mice typically generate a strong cytotoxic T lymphocyte (CTL) reaction in response to P815 cells. Following the initial P815 cell inoculation, the mice were allowed to develop a CTL response (this usually takes about 10–14 days). On days 6 and 8 of the study, a bolus intravenous (iv) injection of a test drug was administered. Mice were then sacrificed on day 14 of the experiment as indicated in the figures; and the allogeneic CTL response was assayed as described previously (Tretiakova et al., 2000, Nature Biotechnology 18:984–988). The primary spleen cells from the treated and untreated animals were used in the direct CTL readout. Freshly obtained primary spleen cells were incubated with the [$^3$H] labeled target cells (P815 cells) at 100:1, 50:1, 25:1, and 12.5:1 ratios for 3.5 hours at 37° C. and harvested using a PHD harvester. The percentage of specific killing was determined using the formula % kill=(S−E)/S, where S is the amount of the DNA retained by the target cells in the absence of the effector cells and E is the amount of retained DNA in the presence of the effector cells (expressed in counts per minute; cpm).

The data disclosed herein demonstrate, for the first time, that the tryptophan-mediated effects on the immune system are due to the role of tryptophan as a metabolic precursor of serotonin. More specifically, a series of studies were performed as disclosed herein to determine the effects of a tryptophan transport inhibitor or a selective serotonin reuptake inhibitor (SSRI).

Blocking the IDO-mediated catabolism of either tryptophan or serotonin had equivalent effects on the conditioned media's ability to allow for T cell proliferation. That is, the depicted experiment in FIG. 1 was designed to block tryptophan uptake into the activated macrophages during the "conditioning" phase of the study (using 2-amino 2-norbornane carboxylic acid, a tryptophan transport inhibitor) or to block the uptake of serotonin during the "conditioning" phase of the study (using fluoxetine [Prozac™], a selective serotonin reuptake inhibitor). This assay yielded variable results: Sometimes the macrophages deplete the media and sometimes they do not (i.e., sometimes, but not always, tryptophan can restore the ability of fresh T cells to proliferate in the conditioned media). In spite of the variability, the overall pattern observed is that the "conditioning" effect of the media can be prevented if either tryptophan or serotonin uptake by the macrophages is blocked. In the assay shown in FIG. 1, the addition of tryptophan had no effect and addition of serotonin only marginally restored the assay. Nonetheless, similar assays have demonstrated that both tryptophan and serotonin can restore the ability of the T cells to proliferate in the conditioned media.

Figure 2:
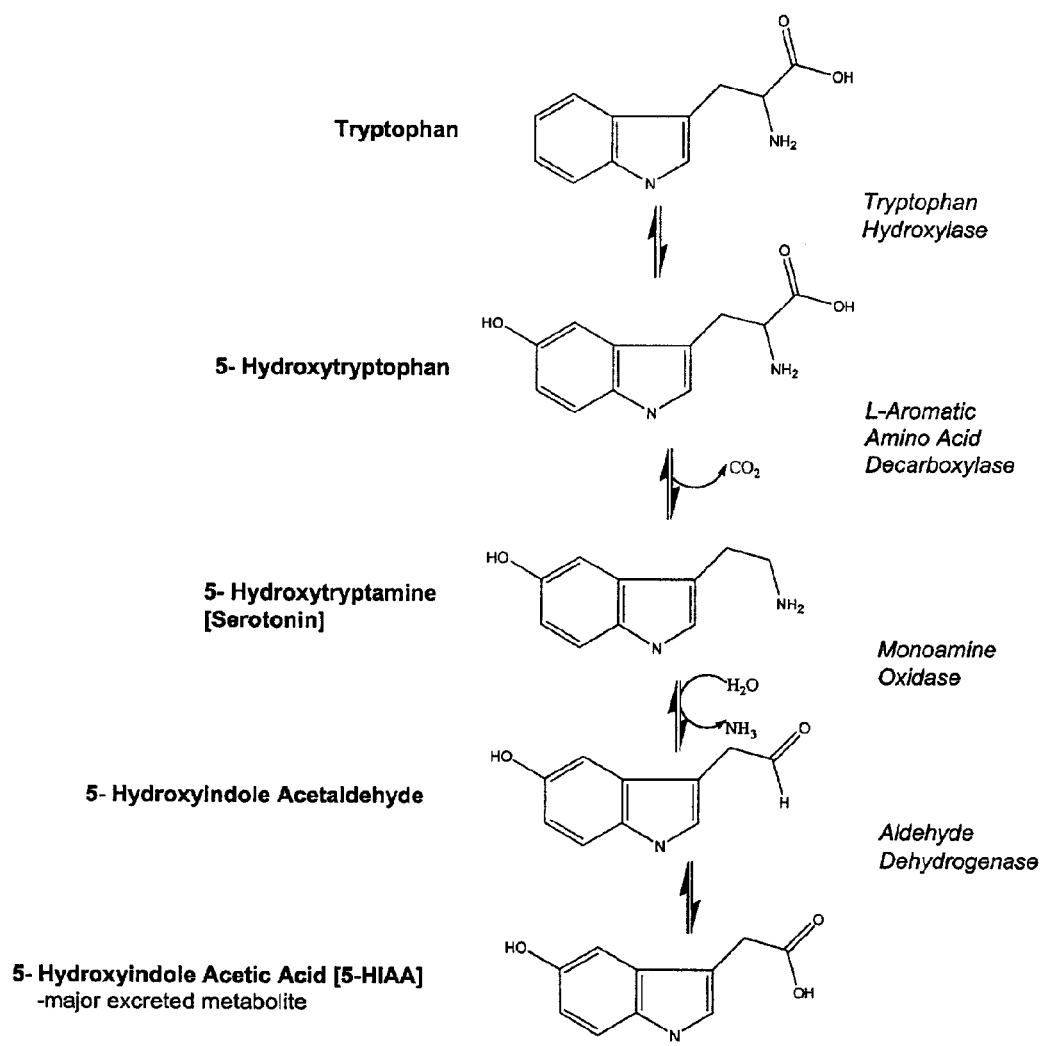
FIG. 2 is a diagram depicting the major metabolic pathway of serotonin synthesis and degradation. The compound names are shown to the left of the structures, while the enzymes catalyzing the individual reactions are shown to the right.

The next series of studies were designed to address the overall role of serotonin in generating an activation response in T cells. Initially, on the role of de novo synthesis of serotonin in the activation response was assessed, as well as the effect of exogenously adding serotonin to the T cells. The metabolic pathway for the conversion of tryptophan to serotonin is shown in FIG. 2. The first enzyme involved in this metabolic conversion is tryptophan hydroxylase. Theoretically, if de novo synthesis of serotonin is required to mount an activation response, then inhibiting the first enzyme in the metabolic conversion pathway should inhibit the response. Furthermore, restoring the activation response by the addition of the missing enzymatic end product can be used to show the specificity of the inhibition.

Figure 3:
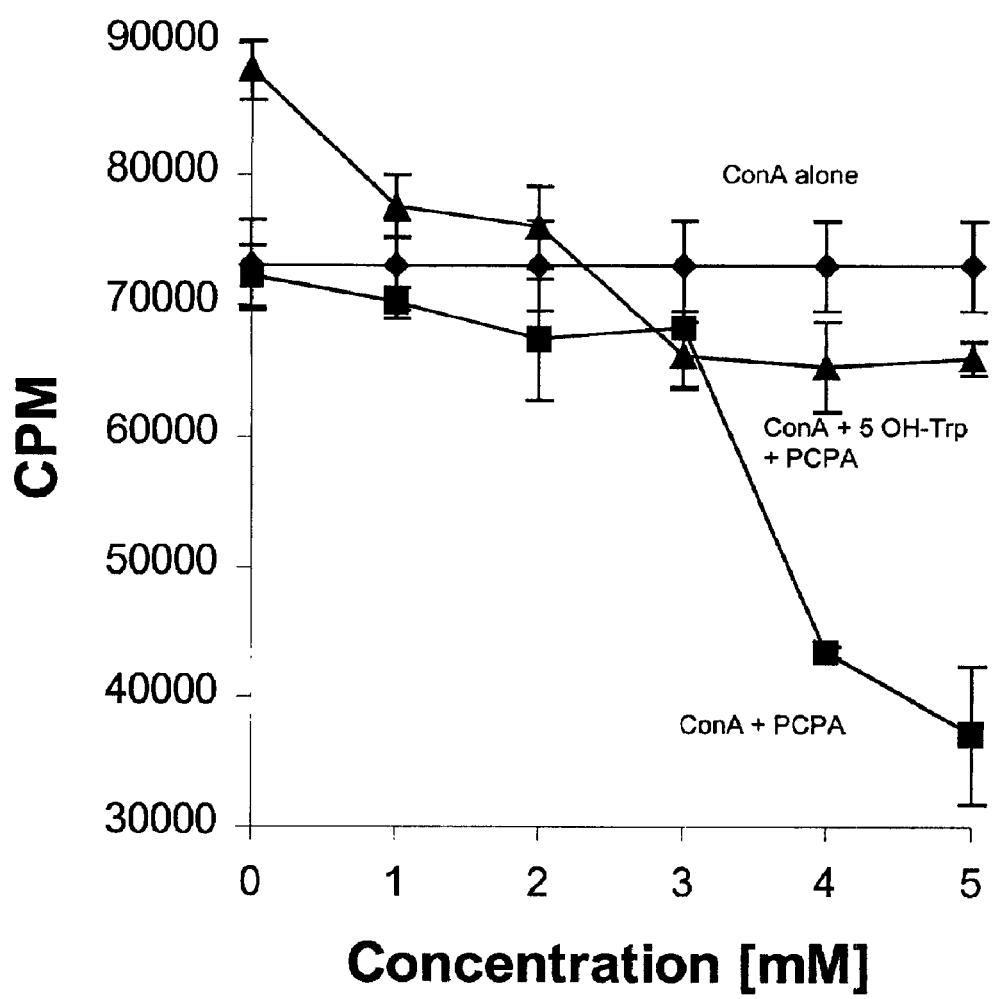
FIG. 3 is a diagram depicting the effects of a tryptophan hydrolase inhibitor (para-chlorophenylalanine, PCPA) on mitogenic stimulation of human lymphocytes. That is, human peripheral blood lymphocytes (PBLs) were stimulated by the addition of 1 $\mu$g/ml ConA.

The experiment shown in FIG. 3 was designed to assess whether or not the inhibition of tryptophan hydroxylase impairs the ability of the T cells to respond to a mitogenic signal. Classically, para-chlorophenylalanine (PCPA) is used to inhibit this enzyme. The study shown in FIG. 3 indicates that the addition of PCPA inhibits the mitogenic response in a dose-dependent manner and that this inhibition can be reversed by the addition of 5-hydroxy-tryptophan, the metabolic endproduct of the enzyme. In the absence of PCPA, the addition of 25 μM 5-hydroxytryptophan significantly enhanced the proliferation response.

Although these data suggest that de novo synthesis of serotonin can move the T cell activation process forward, the mechanism of PCPA's inhibition clouds the interpretation. PCPA added to growing cells incorporates, via protein biosynthesis as an amino acid analog, into newly produced proteins. Although the incorporation of PCPA into tryptophan hydroxylase clearly kills its enzymatic activity, it is difficult to predict the collateral effects of its incorporation into other proteins within the cell.

Figure 4:
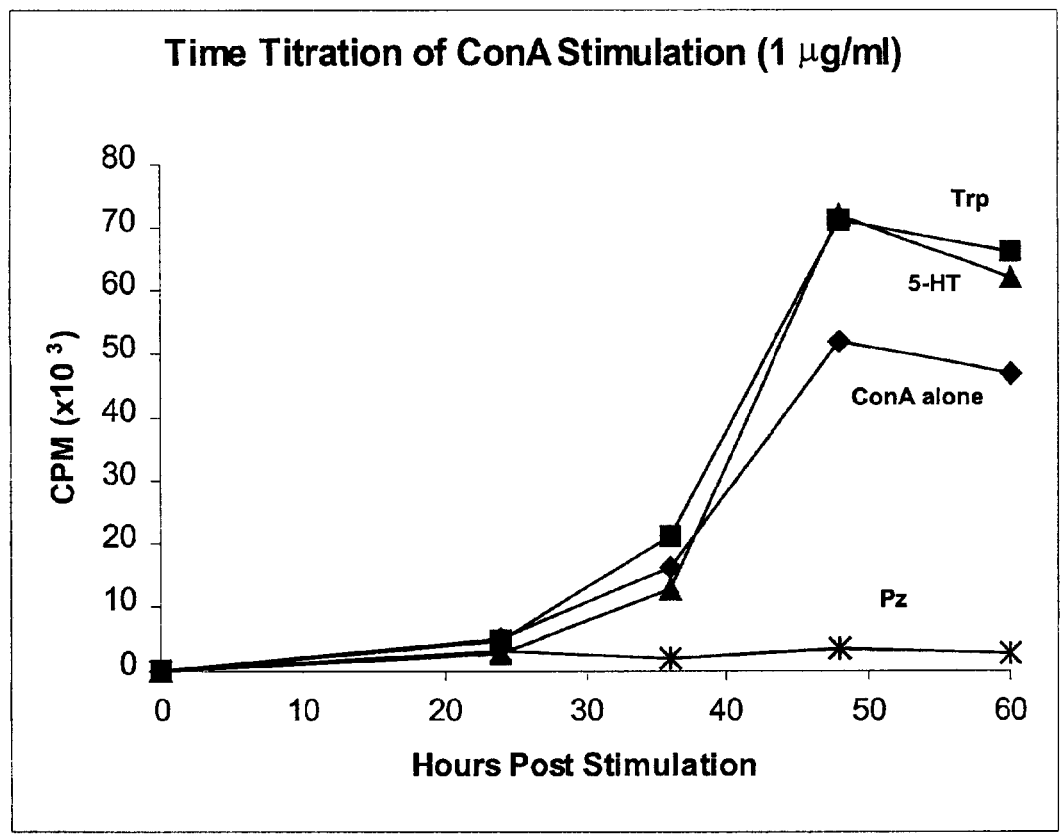
FIG. 4 is a diagram depicting the effects of serotonin, tryptophan, or phenelzine on the activation of human PBLs stimulated with ConA. The assay was harvested at the time points indicating on the graph. The reagents were added at a concentration of 400 $\mu$M.

Next, the effects of exogenously added serotonin and tryptophan were assessed, and the effects of a different metabolic block of the tryptophan-serotonin conversion was examined. Regarding the metabolic block, there is a highly sensitive feedback mechanism that shuts off the activity of the aromatic amino acid decarboxylase (the enzyme that catalyzes the conversion of 5-OH tryptophan to serotonin) in response to a build-up of intracellular serotonin caused through a blockade of the monoamine oxidase enzyme (Carlsson et al., 1976). For this study, Phenelzine (Pz) was used as the inhibitor of the monoamine oxidase. These data are depicted in FIG. 4. The high doses of serotonin and tryptophan (400 μM) enhanced the maximal stimulation of the cells, whereas the addition of the monoamine oxidase inhibitor, Pz, completely shut down the stimulation. These data are consistent with the notion that de novo synthesis of serotonin is required for mounting and maintaining an immune response. Some prior art studies demonstrated that 5-HT stimulates activated T cells (Kut et al., 1992; Young et al., 1993), while most laboratories report that high concentrations of added 5-HT inhibit the proliferation (Mossner & Lesch, 1998). Therefore, the influence of both tryptophan and 5-HT on the basic activation pathway of T cells was examined.

T cell activation and proliferation is an extraordinarily complex and highly regulated process. T cell activation, whether it is initiated using a mitogen or a specific antigen, proceeds as a function of time and activating signal strength. When the activation process is plotted as a function of time versus cell number (or DNA synthesis activity), the graph will resemble a bell-shaped curve. In general, a miltogenically stimulated proliferation assay peaks between 48 and 60 hours, depending on the strength of the initiating signal, plateaus, and then rapidly declines back to the original baseline. In fact, if one disregards the time scale, the curve for generating an immune response strongly resembles that of a nerve impulse.

The experimental set up of a mitogenic stimulation is usually designed to use a single, optimized, concentration of activating mitogen and review the data at a pre-designated endpoint. However, if an exogenously added reagent changes the shape of the bell curve, but not the peak activation level, and the investigator harvests the assay at a single time point, the results can be misleading. Consider the addition of a reagent that shortens the width of the bell curve. At the time of harvest, the shortened bell curve is already approaching it end, while the untreated cells are still in their plateau phase. The investigator would naturally conclude that the test reagent inhibited the assay, whereas the peak response of the cell may have been equivalent, only the duration of the response had changed.

The effects of various compounds under differing strengths of activating signal were examined, while harvesting at a constant time point (72 hours). Theoretically, the strongest initiating signal strength, i.e., the highest concentration of ConA used, will shift the bell curve forward in time, whereas the weaker signals will delay the curve. By using differing concentrations of ConA to stimulate the T cells, while holding the time of harvest constant, the effects of the compounds can be examined at differing points in the "bell curve" of activation. FIG. 5 depicts the effects of each reagent on the stimulated lymphocytes. At the weakest signal strength (0.1 µg/ml ConA), tryptophan augments the proliferative response and that the levels of augmentation decreases with increasing concentrations of ConA such that there is no enhancement at the highest level. Serotonin has no effect on the assay until the highest dose of ConA, corresponding to the latest part of the "bell curve". Thus, without wishing to be bound by any particular theory, it would appear that tryptophan and serotonin have similar effects on the activated cells, except the activity of the tryptophan lags behind that of serotonin.

Figure 5A:
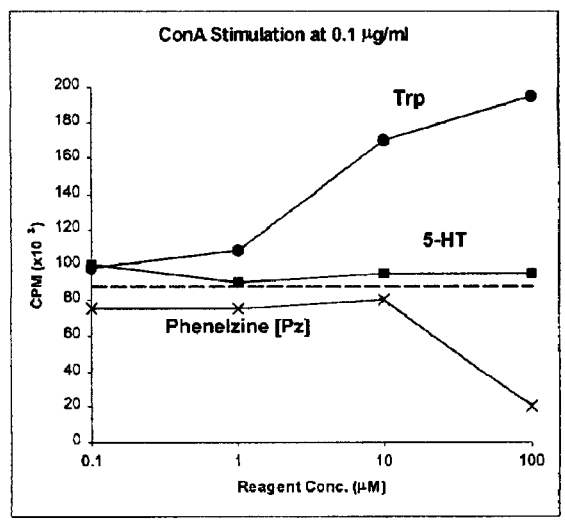
FIGS. 5A through 5C, is a diagram depicting the effects of tryptophan (trp), serotonin (5-HT), and pheneizine (Pz) on the mitogenic stimulation of human T cells at differing concentrations of ConA. That is.
Figure 5B:
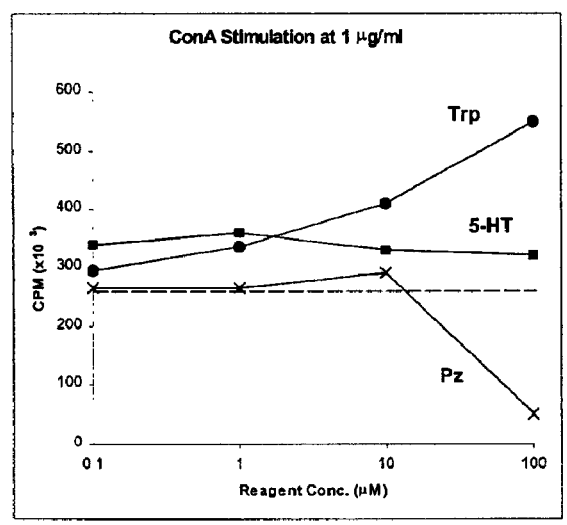
Figure 5C:
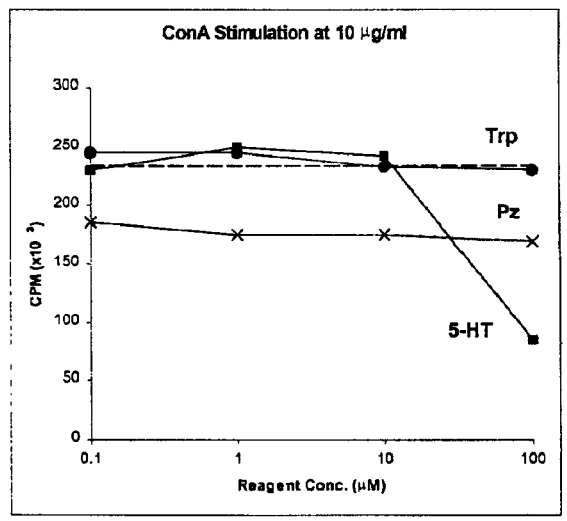

The addition of phenelzine in FIGS. 5A and 5B demonstrates significant inhibition at the highest concentrations of drug used, i.e., between 10–100 µM, as expected for feedback-inhibiting the decarboxylase enzyme. At the highest ConA dose (10 µg/ml), however, no inhibition was observed (FIG. 5C) because the phenelzine inhibition curve shifts to the right at the higher ConA stimulation and full inhibition occurs between 100–400 µM of Phenelzine.

Figure 6:
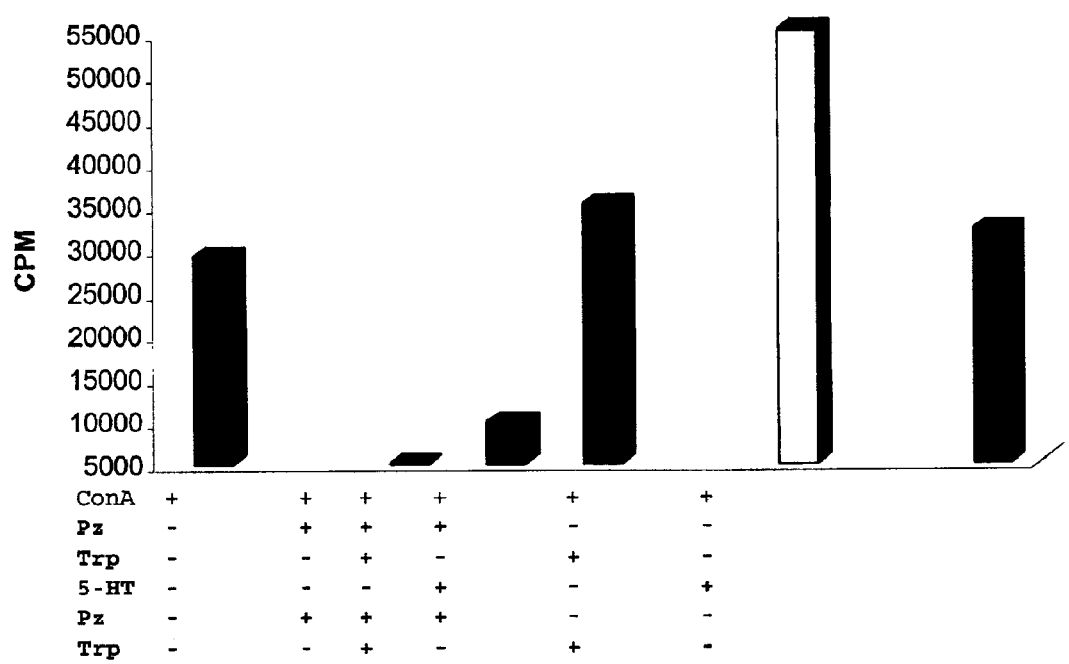
FIG. 6 is a diagram depicting the effects of tryptophan and serotonin addition to phenelzine induced inhibition of activated lymphocytes. The individual reagents (Pz, Trp, and 5-HT) were added at a concentration of 100 $\mu$M.

If the observed inhibition is due to inhibiting the L-aromatic acid decarboxylase, thereby preventing the metabolic conversion of tryptophan to serotonin, then the addition of exogenous serotonin to the assay, but not tryptophan, should relieve the blockage. In FIG. 6, human T cells were stimulated using 1 µg/ml ConA and were probed for the ability of either tryptophan or serotonin to abolish the observed inhibition. Under the conditions used in this assay, tryptophan added to the ConA stimulated cells enhanced the proliferative response, but serotonin did not. The addition of serotonin to the phenelzine-inhibited cells caused the assay to rebound to baseline levels, whereas the addition of tryptophan had very little effect (FIG. 6). Taken together, these data are consistent with and demonstrate that de novo synthesis of serotonin is required for the functional activation of T cells.

In order to assess the role of serotoninergic receptor signalling in the immune response, experiments were conducted to differentially manipulate the immune response using well-defined agonists and antagonists of the 5-HT receptor system. More specifically, the role of the type 1 receptors in the lymphocyte activation process was examined.

Figures 7A, 7B:
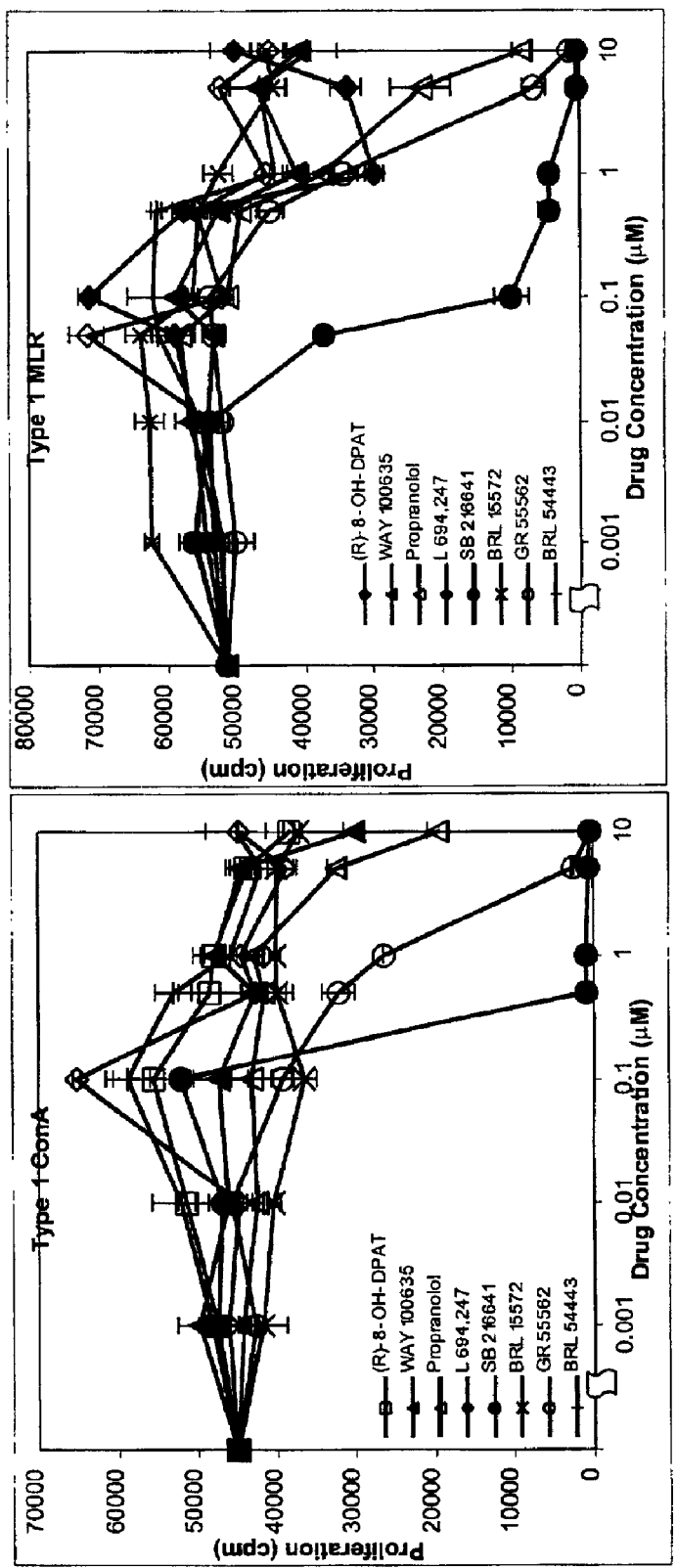
FIG. 7A is a diagram depicting the dose-response effects of titrating a panel of agonists and antagonists known to be selective for the 5-HTR 1 receptors on the activation of ConA (5 $\mu$g/ml) stimulated human lymphocytes. The cells were harvested 72 hours after initiating ConA stimulation. The drugs used for this study have the following well-defined attributes: (R) 8-OH DPAT: a selective agonist for the 5HT 1A receptor; WAY 100635: a selective antagonist for the 5HT 1A receptor; Propranolol: a general 5HT 1 receptor antagonist as well as a beta-adrenergic antagonist; L 694247: a selective 1B/1D agonist; GR 55562: a selective 1B/1D antagonist; SB 216641: a selective 1B antagonist; and BRL 15522: a selective 1D antagonist; BRL 54443: a selective 1E/1F agonist.
FIG. 7B is a diagram depicting the dose-response effects of titrating a panel of agonists and antagonists known to be selective for the 5-HTR 1 receptors on the allogeneic stimulation of human lymphocytes (otherwise known as a mixed lymphocyte reaction). The cells were harvested 120 hours after the initiating stimulation. The drugs used for this study have the following well-defined attributes: (R) 8-OH DPAT: a selective agonist for the 5HT 1A receptor; WAY 100635: a selective antagonist for the 5HT 1A receptor; Propranolol: a general 5HT 1 receptor antagonist as well as a beta-adrenergic antagonist; L 694247: a selective 1B/1D agonist; GR 55562: a selective 1B/1D antagonist; SB 216641: a selective 1B antagonist; BRL 15522: a selective 1D antagonist; BRL 54443: a selective 1E/1F agonist.

The data from these assays are shown in FIG. 7A and 7B. Panel A of this figure shows the stimulation of the human lymphocytes with 5 µg/ml ConA, while panel B shows data with respect to an allogeneic stimulation of the human lymphocytes, i.e., a mixed lymphocyte reaction. As can be clearly seen in these data, the highly selective inhibition of the 5-HT 1B receptor signal using the compound SB 216641 results in the complete inhibition of the activation response.

The data further demonstrate that the dose response curve for the selective 5-HT 1B antagonist (SB 216641) is, in part, dependent upon the signal strength intensity of the method of cellular activation. That is, using the plant lectin ConA to cross-link the extracellular receptors, bypassing the need for secondary signal input, the 5-HT 1B inhibition has an apparent $IC_{50}$ of about 200 nM, whereas using an allogeneic stimuli (of weaker signal strength), the same compound has an apparent $IC_{50}$ of about 50 nM. It should be noted that the selective 1B/1D antagonist significantly inhibited these assays at pharmacologically relevant concentrations, but the highly selective 1D antagonist (BRL 15572) had no effect upon the proliferative response. Thus, the data disclosed herein distinguished a functional difference between the human 1B and 1D receptors in the immune response and demonstrate that the selective withdrawal of the 5-HT 1B receptor signal completely abrogates the lymphocytic activation response.

In this same line of investigation, the ability of agonists and antagonists targeted at the type 2 serotonergic receptors to modulate immune responses was assessed. These data are shown in FIGS. 8A and 8B. Again, there was a comparison of the drug effects on a mitogenic stimulation (ConA) of human lymphocytes versus the same drug panel in a human mixed lymphocyte reaction, panels A and B, respectively. In these studies, several of the tested drugs inhibit the activation response at pharmacologically relevant concentrations, namely methiothepin (a general antagonist of the 5-HTRs 1, 2, 6, and 7), LY 53857 (a selective inhibitor of the 5-HT 2A/2B/2C receptors), SB 206553 (a selective inhibitor of the 5-HT 2B/2C receptors), and SB 242084 (a highly selective inhibitor of the 5-HT 2C receptor). The only common denominator among these various drugs is their ability to inhibit the 5-HT 2C receptor signal. Thus, these data demonstrate that selective withdrawal of the 5-HT 2C receptor signal completely inhibits the activation process of human lymphocytes.

FIGS. 9A and 9B depict the effect of inhibiting or agonizing receptor signaling from the 5-HTRs 3, 4, 6 and 7 (the 5-HT 5 receptors were not probed because there are no available agonists or antagonists that can be specifically used to target this receptor system). Neither agonism nor antagonism of the 5-HT 3 receptors has any effect on the proliferative ability of these cells to respond to either mitogen or allogeneic stimuli. Both agonism and antagonism of the type 4 receptor inhibits the response. In this regard, it is generally known that the agonists to the type 4 receptor induce down-regulation of the receptor, resulting in the subsequent withdrawal of these signals. Specific inhibition of the 5-HT 6 and 7 receptors had no effects on these CD4-dependent assays.

Although the most dramatic effects were seen with the use of the type 1 and type 2 antagonists, the effects of stimulating the 5HT type 3 receptor, as well as selectively inhibiting the 5HT 6 receptor were also examined. More specifically, a murine mined lymphocyte response assay (MLR) was used to assess effects. The Ro 04–679, a selective type 6 antagonist, had no effects on the outcome of the assay, whereas there was a slight enhancement with the use of 5-methyl hydroxytryptamine, the type 3 agonist thus far, no qualitative differences in inhibitor behavior between mitogenic stimulations and allogeneic stimulations have been disclosed previously or elsewhere herein.

The assays disclosed previously the incorporation of $^3$H-thymidine into growing strands of DNA, i.e., DNA synthesis. Without wishing to be bound by any particular theory, if one compound acts by leaving the cells viable but unable to grow and another compound acts by inducing apoptosis (programmed cell death), the results will be identical when DNA synthesis is used as the endpoint of the assay.

To further assess the effects of propanolol (a general 5-HTR 1 antagonist) and risperidone (a general 5-HTR 2 antagonist) on the mitogenically stimulated lymphocyte culture, the number of viable cells were manually counted as the assay progressed. These cell counts are shown in FIG. 11. If the cells were not stimulated, there was no detectable change in the number of viable cells. When the cells were stimulated with ConA, a small lag period was observed and the beginning of the growth phase compared to the stimulation response curve observed in the absence of the inhibitor. The 5HT type 1 receptor antagonist prevents the cell from growing. Apparently, there is no decrease or increase compared with the starting cell numbers. It is unclear whether or not this is due too anergy, an inability to initiate the activation pathway, or both. The risperidone, on the other hand, caused a brief cell increase, followed by the elimination of the cells in culture. It should be emphasized that these data can only be obtained through a manual counting of the cells numbers; DNA synthesis assays would have indicated equivalent results for the two compounds. Thus, based on the data presented here, the classes of antagonists that inhibit the type 2 serotonin receptors appear to be rate limiting for the lymphocyte activation processes.

Because the data disclosed herein demonstrate that the T cell activation signals were most responsive to signals generated either through the 5-HT 1B or 5HT type 2 receptors, pharmacologic studies were designed to corroborate the data concerning which of the three type 2 receptors had the greatest influence on the immune system. Consequently, a series of 5HT 2 antagonist with varying specificities that do not cross-react with any other receptor systems were assessed (FIG. 12). The first compound, LY 53857, targets all three type 2 receptors. The second compound SB 206553, selectively targets only the 5HT 2B and 5HT 2C receptors. The third compound, MDL 11939, targets only the 5HT 2A receptor. The fourth compound, SB 242084, is a highly selective antagonist of the 5HT 2C receptor. All of the drugs were dosed either at the beginning of the assay (time=0) or at the beginning of the second activation phase (time=48 hours). The data disclosed herein that the 5HT 2C-specific antagonist has retained the complete inhibitory profile (see, e.g., FIG. 12). Without wishing to be bound by any particular theory, the data disclosed herein demonstrate that the 5HT 2C receptor signal is the rate-limiting signal observing seen during the activation process in lymphocytes.

Therefore, the data disclosed herein indicates that tryptophan is actively converted to serotonin during the T cell activation response. Moreover, pharmacologic profiles indicate that the 5HT type 1 receptors, most notably the type 1A receptor, appear to initiate the activation response. This observation is surprising in light of the prior act indicating that the 5HT 1A receptor is not present on resting cells and is only up-regulated upon Tall activation. In contrast to the type 1 receptors, the 5HT type 2 receptors appear to require serotonin-mediated signaling at both early and late phases of the activation response. Interruption of this signal at any point during the response results in the immediate cessation of activation. More specifically, the data disclosed herein demonstrated, for the first time, that signaling through the 5HT 2C receptor is absolutely required for mounting and maintaining an immune response.

Mellor et al. (1998, Science 281: 1191–1193), probed the question of how a fetus manages to survive allograft rejection (considering that the fetus is half mother and half father). Approximately 8 days after the concepti forms within the womb, an enzyme (indoleamine 2,3 diooxygenase, IDO) is upregulated. This enzyme is known to catabolize indoleamines, such as tryptophan and serotonin. This time lag between conception and the upregulation of the enzyme is sufficient time to allow for the activation of a T cell response. In other words, the body allows the immune response to occur and before any damage can be done, the IDO is upregulated, suddenly withdrawing the local supply of serotonin. Although not wishing to be bound by a single hypothesis, it is possible that the sudden loss of the serotonergic signal induces apoptosis in the activated set of cells, thus functionally deleting the cells that could respond to the fetus, while leaving the resting cell population intact ready to respond to any foreign pathogen. To setup an in vivo validation of the in vitro data, a robust art-recognized allograft rejection model was selected.

Because the data disclosed herein suggests a potential mechanism used by nature to protect against an unwanted allogeneic response to a conceptus during gestation, the effect of 5-HTR activation in an allograft rejection model was examined, P815 cells (a rapidly growing cell line taken from a mastocytoma in a DBA mouse) were used to create a powerful rejection response in a C57BL6 mouse. This is an art-recognized model of allograft allergist rejection based on that described by Han et al. (2000). In this model, there is a complete MHC mismatch between the P815 cells (H-$2^d$) and the C57BL6 mouse (H-$2^b$), thus ensuring an aggressive immune response. The data disclosed in FIG. 13, depicts results of experiments that included 6 treatment groups, each group consisting of three mice. Each mouse received 5×10$^6$ P815 cells injected into the peritoneal cavity on day 0 of the study. The first group was an untreated control group, which was used to establish the baseline response of the mice against the allogeneic stimulus. These mice, without any further treatments, were sacrificed, as were the other treatment groups, on day 14 of the study and their splenocytes assayed for target-specific killing of the P815 cells.

The average kill observed for the untreated group was about 45% at an effector to target ratio of 100:1. The second group was treated with risperidone, a 5HT-2 antagonist, administered via a tail vein bolus injection (200 μg/injection) on days 6 and 8 of the study. The timing of the drug administration was selected to ensure that the T cells were fully activated prior to the drug treatment. The third group was treated with propanolol, a 5HT-1 antagonist. All of the 5HT receptor antagonist-treated groups were treated as described for the risperidone-treated group. The fourth group was treated chronically with CyclosporinA. The Cyclosporin A was administered ip at a dosage of 100 μg/injection starting two days prior to the onset of the study, i.e., at day-2, and the injections were continued on a daily basis for the duration of the study.

The Cyclosporin A effectively prevented the T cells from initiating an activation response and is currently one of the drugs of-choice for treating complications arising from transplantation procedures. The fifth and sixth groups were treated with SB206553 (a highly selective 5HT-2C antagonist) and methysergide (clinically known as Sansert™), which is a general 5HT 1 and 5HT 2 antagonist, respectively. As demonstrated by the data disclosed herein, the Cyclosporin A-treated mice did not develop a cytotoxic response to the allograft, as expected (FIG. 13). The propanolol-treated group did not protect the mice from the allograft rejection response. This observation was consistent with demonstrating that the 5HT 1 receptors primarily effect the early phases of the activation response.

The risperidone, SB206553, and methysergide-treated groups all inhibited the allograft response to varying degrees. As an illustration of the nature of the immunomodulation observed in the antagonist-treated groups, FIG. 14 depicts the individual responses of each mouse within the SB 206553-treated group. Two of the three treated mice inhibited the allograft response to a degree equivalent to that observed in the Cyclosporin A-treated animals. The one mouse that did not respond to the drug treatment required multiple injections of the drug because the initial attempts at the tail vein injection failed. The data demonstrates that the in vitro dose-inhibition curves rapidly progress from no inhibition, to 100% inhibition, almost as if it is a "threshold-type" response. Without wishing to be bound by any particular theory, it is possible that the one non-responding mouse did not receive a full dose of the drug or that the stress of multiple injections induced a serotonin response in the mouse.

As a neurotransmitter, serotonin exerts its differential effects on a given cell depending on the type of 5HT receptor presented on the surface of the responding cell. The immune response is highly regulated and subject to subtle changes in the expression of its response depending on the nature and context of the presenting antigen. Therefore, one could imagine, without wishing to be bound by any particular theory, that if responding cells express a differential array of serotonin receptors because serotonin plays a crucial role in regulating the immune response. It is clear that both monocytes and lymphocytes express serotonin-specific receptors. A review of the prior art, however, creates a confusing view of the receptor expression patterns. Table 1 shows the studies and their conclusions regarding serotonin receptors and immune system cells.

TABLE 1

| Literature Citation | 5HT Receptor(s) | Type of Evidence |
| --- | --- | --- |
| Ameisen et al., 1989 | 5HT 2 (mouse) | Pharmacologic |
| Aune et al., 1993 | 5HT 1A [no type 2] (mouse) | RT PCR |
| Meyniel et al., 1997 | 5HT 3 activated cells only (rainbow trout) | Pharmacologic |
| Stefulj et al., 2000 | Resting: 5HT 1B, 1F, 2A, 2B, 6 and 7 Activated: 5HT 3 (rat) | RT PCR |
| Marazziti et al., 2001 | 5HT 2C and 5 (human) | RT PCR |

The earliest study demonstrates the pharmacological presence of a 5HT 2 receptor on T cells, whereas a subsequent paper, published from the Miles Research Center, presents RT PCR evidence that the 5HT 1A receptor is present, but not the 5HT 2 receptors. Furthermore, they found that the 5HT 1A receptor is only present on activated T cells. Work from a laboratory in Serbo-Croatia (Stefulj et al., 2000), used reverse transcription polymerase chain reaction (RT PCR) with primers to 13 of the 14 known, pharmacologically distinct, receptors and found that neither 5HT 1A nor 5HT 2C were present. A recent paper from the University of Pisa by Marazziti et al. (2001, Neuropsychobiology 43:123–126), indicates the presence of 5HT 2C. These studies are clearly at odds with one another. The data disclosed herein are consistent with respect to the in vitro and in vivo data. Therefore, a series of studies designed to probe the 5HT receptor expression on the human cells that were used in the assays described above using sequence-specific primers for the serotonin receptors were performed.

For these studies, PCR primers were created which were specific for the 5HT 1A, 2A, 2B, 2C, 3A, 3B, and 4 receptors (see the methods section, supra, for both the experimental details as well as the individual primer sequences). Haman peripheral blood lymphocytes were purified according the protocols disclosed elsewhere herein for performing mitogenic stimulations and human MLRs. The antigen presenting cells, consisting of the monocytes, were separated from the lymphocytes. cDNA libraries were produced using these cell populations either before or after stimulation with 10 µg/ml ConA. RT PCR was used to probe for the presence of the individual receptors.

The data obtained with using the 5HT 1A-specific primers was unanticipated. The expected fragment size was 234 bp. This band was faintly observed only in the activated lymphocyte population and could not be detected after the picture of the gel was taken to produce the image depicted in FIG. 15. Instead, the major product amplified by the primer pairs was a band migrating at about 387 bp whereas all of the other amplified fragments from the other receptors depicted in FIG. 15 corresponded precisely to the expected fragment lengths. This 387 bp band cannot be accounted for by any of the known 5HT 1A receptor polymorphisms or any of the known splice variants.

In parallel with the PCR amplification depicted in FIG. 15, the individual cDNA libraries were amplified using PCR with the receptor-specific primers and cloned into an expression vector, i.e., the TA expression vector, pCR3.1 (Invitrogen), for DNA sequencing.

Although the PCR data disclosed here is not quantitative, an attempt was made to normalize condition across all PCR reactions depicted herein. The major bands depicted in FIG. 15 using the 5HT 1A specific primers appear to be qualitatively more intense in the resting lymphocytes and activated monocytes than it is in the resting monocytes and activated lymphocytes. The 387 bp band, as well as the expected size fragment, has been cloned into the TA vector. Sequencing will identify these PCR these products.

In terms of the 5HT 2 receptors, the 5HT 2A is present on the lymphocytes and the band appears to be more intense in the resting lymphocytes than on the activated cells. The 5HT 2B receptor appears to be present only in the resting monocytes and lymphocytes and disappears when the cells become activated. The 5HT 2C receptor is present on both resting and activated lymphocytes. The presence of 5HT 3 receptors was not detected. This was a surprising result considering the literature references and the pharmacologic data obtained in the experiments disclosed herein. Without wishing to be bound by any particular theory, it is possible that there is an unanticipated polymorphism or other difference in the receptor mRNA such that the designed primer pairs used herein were unable to amplify the corresponding cDNA. This RT PCR will be repeated using a different set of primer pairs.

Additionally, a clear band of the expected size in the amplifications of the 5HT 4 receptor was detected in this assay. This band appears in the resting lymphocytes and in the activated monocytes. As mentioned above, each of these bands shown in FIG. 15 has been cloned and will be sequenced for authenticity.

Serotonergic-based immunotherapies are employed by nature. This strategy can be used to devise treatments of multiple sclerosis, type 1 diabetes, rheumatoid arthritis, Crohn's disease, ulcerative colitis, as well as many other autoimmune diseases. The same drug strategies could be used to stop the immune response involved in the rejection of genetically mismatched solid organ, hematologic, and stem cell transplants, as well as the response aimed at gene therapy vectors.

Current therapies used to treat these disease states are not only toxic but also block patients' entire immune system with each daily dose, rendering them immunocompromised for the rest of their lives. While an organ remains temporarily protected, or a relapse is briefly avoided, the patient is left vulnerable to opportunistic infections.

The data disclosed herein thus enable a novel specific therapeutic approach. Essentially, cells at the fetal-maternal interface express an enzyme (IDO), which locally degrades indoleamines, such as serotonin and tryptophan. Immune cells require serotonin signaling via specific receptors on their cell surface, and thus depletion of serotonin results the sudden loss of critical activation signal(s) and the consequent functional deletion of the activated set of T cells, thus protecting the allogeneic fetus.

The enzyme involved is only necessary early in the gestation period (approximately the first trimester). It is important to note that the suppression of the immune response is limited only to those cells activated during the time of the enzyme's activity. Without wishing to be bound by any particular theory, during a pregnancy with no other infections or diseases, the only activated cells would be those targeted against the fetus; thus, these are the only cells which should be inhibited. The temporary removal of serotonin signaling is enough to block the immune response against the fetus for the remainder of the pregnancy, but once the enzyme has stopped working and serotonin levels have been locally restored, any other normal immune response can proceed.

Without wishing to be bound by any particular theory, serotonin receptor drug therapies can work similarly, by selectively mimicking the depletion of serotonin. Instead of removing serotonin to prevent its binding, receptor signal inhibitors act by either out-competing the neurotransmitter at the receptor binding sites or non-competitively inhibiting the receptor signal, with the same end result. An autoimmune disease, or transplanted state, is similar to the pregnancy in that in an otherwise healthy person, the only activated immune cells would be those targeting the "self" tissue or foreign organ. A serotonin-based therapy, which can be dosed in a pulse therapy, can analogously target activated cells in these patients, while leaving their resting immune systems ready to respond once the pulse of drug has been cleared from their circulation.

In an attempt to improve the therapeutic treatment regimens, new experimental therapies are being developed and tested. Biological applications to block the CD40/CD154 costimulatory pathway have shown, perhaps, the most promising activities of all of the experimental systems that have been evaluated to date (Diehl et al., 2000, J. Molec. Med. 78:363–366). A non-depleting anti-CD154 antibody has been used to prolong graft survival of a full MHC mismatch in rhesus monkeys (Kirk et al., 1999, Nature Medicine 5:686–693; Kenyon et al., 1999, Proc. Natl. Acad. Sci. USA. 96: 8132–8136). The antibody treatment apparently exploits activation-induced cell death (AICD) as an important feature of its therapeutic effect on prolonging allograft survival (Markees et al., 1998, J. Clin. Invest. 101: 2446–2452). Additionally, it has been shown that the tolerance induced with anti-CD 154 antibodies involves not only the deletion of potentially aggressive T cells, but also inhibits new cohorts of graft-reactive T cells (Graca et al., 2000, J. Immunol. 165: 4783–4786). Most of the studies with the anti-CD 154 antibody, however, indicate that the allografts eventually reject due to arteriosclerosis. The transplant arteriosclerosis that develops in the experimental animals apparently arises from an invasion of CD8+ cytotoxic T cells (Honey et al., 1999, J. Immunol. 163: 4805–4810). Recent data suggest that the CD8+ T cells are not effectively targeted by the CD154 blockade (Ensminger et al., 2000, Transplantation 69:2609–2612). Even though the CD8+ CTL response may slip through the CD40 ligand blockade, the therapeutic effects of anti-CD154 monoclonal antibody administration have been nothing short of spectacular and seem to be devoid of any major untoward side effects (Kenyon et al., 1999, Proc. Natl. Acad. Sci. USA 96: 8132–8136).

Monoclonal antibodies are playing and will continue to play a role as a new medical treatment regimen. These antibodies account for about a quarter of all biotech drugs in development today and, approximately, 30 products that are currently in use or being investigated (Breeveld, 2000, Lancet 355:735–740). Monoclonal antibodies, however, inherently suffer from several limitations. As is true for any relatively large protein, the cost of commercial production and purification procedures for human therapeutic use is extraordinarily high, relative to the cost of manufacturing (the more traditional) small organic drugs (Hillegass et al., 1999, Am. Heart J. 138:S24–32). Although the short-term side effects of monoclonals are tolerable and predictable, long-term safety remains to be elucidated. Although in vivo half-lives of a week or more are not uncommon, monoclonal antibodies often have problems associated with tissue penetration, such as their inability to efficiently penetrate sinovial tissues in rheumatoid arthritis (Colcher et al., 1998, Q. J. Nucl. Med. 42:225–241). In short, monoclonal antibodies will provide an immediate solution to some of the unresolved medical problems, but do not represent a long-term solution. As has been often noted by the major pharmaceutical companies, the best drug is still a classical small organic molecule.

It has been said that, "The Holy Grail of transplantation research has been to induce tolerance by a short pulse of therapy." (See Prof. Herman Waldmann, Sir William Dunn School of Pathology, Oxford, UK). The rationale employed here is to devise a strategy for engineering a short pulse therapy that exploits activation-induced cell death, AICD. The diversity of 5-HT receptors found on the lymphocytes should be sufficient to allow for both positive and negative regulation of the activation responses. It is tempting to speculate, without wishing to be bound by any particular theory, that the serotonin system represents the primordial defense system and that the participation of the diverse cellular determinants that provide the elaborate regulatory elements of the immune response were added into the system with time. In fact, there is wide spread recognition that the generation of an immune response involves an "immunological synapse", not unlike a neural junction (Bromley et al., 2001, Ann. Rev. Immunol. 19:375–396). The mechanism employed by nature to prevent fetal rejection had to have been an early event on the evolutionary time scale in order to preserve reproduction of the species. If the serotonin pathway represents a primordial defense pathway, then it might make sense that nature would choose to control the serotonin levels, via tryptophan depletion, to protect the fetus during pregnancy.

Targeting the serotonergic receptor signals for controlling "unwanted" inflammatory responses offers the advantage of being able to draw on a vast database of information regarding pharmacologically-pharmaceutically selective antagonists of the serotonin receptor system. Unlike the use of monoclonal antibody-based therapies, this strategy offers a means of functionally deleting all of the activated T cells (both helper and cytotoxic T cells) involved in generating the immune response.

The obvious benefit of using nature's pathway for controlling the immune is that a single treatment will provide, at least, several months of protection. The ultimate duration of this protection is not known. In turn, the obvious therapeutic targets encompass a plethora of diseases involving pathogenic inflammatory responses, such as multiple sclerosis and rheumatoid arthritis. Unlike the current use of COX-2 enzyme inhibitors (such as Celebrex™), the serotonin-based therapies are designed to functionally delete the cells responsible for creating the disease not just temporarily slowing the response.

In summary, serotonin receptor antagonists can be used to mimic a powerful, natural, primordial mechanism of immune protection designed for or arising out of the need for fetal survival. The data disclosed herein provide a tool for the development of methods for the treatment of autoimmune diseases and transplant immunology, as the goal of treatment in these fields is to analogously attempt to inhibit unwanted immune responses without harming the resting population of immune cells needed for future infections. This therapeutic strategy has implications in the treatment of multiple sclerosis, type 1 diabetes, rheumatoid arthritis, Crohn's disease and ulcerative colitis, as well as many other autoimmune diseases. This therapeutic strategy can also be used to protect genetically mismatched solid organ, hematologic, and stem cell transplants, as well as the vectors currently used for gene therapy.

Example 2

Differential Expression of 5-HT Receptor Subtype mRNA

Total cellular RNA was extracted using Qiagen RNAeasy minipreps, according to the manufacturer's instructions. RNA samples were quantitated by EtBr staining of the gel and approximately 1 µg of each RNA sample was used for the cDNA synthesis. cDNA synthesis was performed with Qiagen Reverse Transcriptase according to the manufacturer's instructions, using oligoT$_{12-18}$ primer. The resulting cDNA served as a template in PCR (Taq DNA polymerase, Sigma) using 5-HT receptor specific primers. PCR conditions were: 95° C. for 45 sec., 61.5° C. for 45 sec., 72° C. for 45 sec. 25 cycles will be followed by 10 min. extension step (72° C.). PCR products were analyzed by 3% agarose gel electrophoresis (TAE buffer). For additional verification, PCR products were subjected to Southern Blot Hybridization, using radioactively labeled receptor-specific internal oligonucleotides as probes. PCR products were transferred from the agarose gels to HyBond membranes and hybridizations were performed as described in the Current Protocols In Molecular Biology. Briefly, membranes were pre-blocked in 6×SSC, containing 10× Denhardt's solution, 0.5% SDS, 1 µg/ml polyA, and 100 µg/ml of SS DNA. 20 pmol of radioactively labeled probe was added per hybridization and incubated overnight (at 73° C.). The next day the excess probe was washed away and the membranes were exposed to Kodak film. Internal oligonucleotides were: 1A:

```
                                       (SEQ ID NO:1)
  ctgcagaacgtggccaattatcttattggctctttt;    1B:

(SEQ ID NO:2)
  gtggagtactcagctaaaaggactcccaagaggg;      1D:

(SEQ ID NO:3)
  ctctcttttcaaccacgtgaaaatcaagcttgct;      1E:

(SEQ ID NO:4)
  atctagatcacccaggagaacgtcagcagatctcta;    1F:

(SEQ ID NO:5)
  gagcagcaaagacattataccacaagagacaagcaa;    2A:

(SEQ ID NO:6)
  tcggctcttttgtgtcattttcattcccttaacca;     2B:

(SEQ ID NO:7)
  ctcaacgcctaacatggttgactgtgtctacagttt;    2C:

(SEQ ID NO:8)
  taactgacattttcaatacctccgatggtggacgct;    3A:

(SEQ ID NO:9)
  gggagttcagcatggaaagcagtaactactatgcag;    3B:

(SEQ ID NO:10)
  ttcaatctatcagcaactacctccaaactcaggacc;    4:

(SEQ ID NO:11)
  caccattctttgtcaccaatattgtggatcctttc;     5:

(SEQ ID NO:12)
  cttttggctggggagagacgtactctgagg;          6:

(SEQ ID NO:13)
  atcctcaacctctgcctcatcagcctggac;          7:

(SEQ ID NO:14)
  tgaaaggaaaaacatctccatctttaagcgagaaca.
```

The Results of the experiments disclosed herein are as follows.

Regarding the expression of 5-HT receptor-specific mRNAs in human lymphocytes, the data disclosed herein demonstrate, instead of characterizing the presence or absence of 5-HT receptor's mRNAs in resting cells versus cells stimulated for 48 hours, whether or not there is a kinetic regulation of the receptor mRNA levels as the activation process proceeds. For these studies, cells were treated with 5 µg/ml ConA at the beginning of the study (time=0). Time points were taken at 0, 0.5, 2, 4, 6, 12, 24, and 48 hours. For each time point 1 µg of total cellular RNA was used to make an oligo-dT-primed library. These oligo-dT libraries served as templates to amplify each of the 14 5-HT receptors. In lieu of cloning and sequencing each of the amplified products, the authenticity of the products was validated using Southern Blot hybridization, using receptor-specific internal oligonucleotides as probes as disclosed elsewhere herein. Genomic DNA amplification was used as a positive control; the negative control was the RNA amplified without the reverse transcription step in order to control for the DNA contaminations.

The data for this study is depicted in FIG. 16. The time points (in hours post-stimulation) of the various samples are shown at the top and bottom of the blots and the individual 5-HT receptors are indicated in each blot on the left-hand side. "M" indicates the marker lane. It should be noted that the data shown for the 5-HT 2C receptor is not a Southern blot, it is an ethidium bromide stained gel demonstrating that the PCR products along with the positive control run at the expected size.

The data shown in FIG. 16 indicates a uniquely coordinated expression pattern for each of the serotonin receptors-specific messages. There is no evidence of the expression of the 5-HT 1F or 3B receptors and the respective primers were re-designed and still do not amplify any products. Upon longer blot exposures there is a faint, but reproducible, band corresponding to the 3A receptor.

With regard to data relating to the 1A and 2A receptors, the studies were repeated using blood drawn from a variety of different individuals and for longer time frames. The 5-HT 1A appears at approximately 54 hours post stimulation. This time point coincides with the peak of the assay and the beginning of the down-turn of the activity. Using two rounds of PCR amplification (25 cycles each) for the 2A receptor, the expected size RT-PCR products were detected; however, the PCR product was not detected using Southern Bloting when only one round of PCR (25 cycles) was performed. In other assay data the 5-HT 2A appears as a regulated band (upregulated immediately after the onset of the stimulation and re-appearing immediately prior to the second round of cell division). These data suggest, that 5-HT 2A mRNA is present in lymphocytes. The identity of the 5-HT 2A products have been verified by Southern Blot hybridization.

Further, the data disclosed herein demonstmte the pharmacological behavior of serotonergic receptor agonist and antagonist on both human arid murine lymphocytes. FIG. 17 shows the resuhs of a panel of class 1-specific drugs on the mitogenic stimulation of human lymphocytes and equivalent results were observed within the murine system. Overall, the most striking inhibition of the response was observed with respect to the selective withdrawal of the 5-HT 1B receptor signal. Simultaneous inhibition of the 1B and 1D signals, however, does not yield the same inhibition curve, although the binding kinetics for the 1B receptor for both drugs are equivalent (for details regarding the 5-HTR drugs see World Wide Web.tocris.com.

The data depicted in FIG. 17 demonstrate the effect on $^3$H-thymidine uptake of various drugs. This should be a reflection of the DNA synthesis occurring in the CD4+ subset of cells. Thus, these data represent the in vitro drug effects on helper T cells.

Finally, studies conducted in vivo using the CD8-dependent allograft rejection model, in which P815 cells (a rapidly growing cell line taken from a mastocytoma in a DBA mouse), were expanded and used to create a robust rejection response in a C57BL6 mouse. In this study the mice received $5 \times 10^6$ P815 cells injected into their peritoneal cavity on day 0 of the study. The first group was an untreated control group (naïve animals), used to acquire the baseline response of the mice against the allogeneic stimulus. The positive controls were treated with the allogeneic cells without any further treatments. These animals were used to assess the induced allogeneic response against the P815 cells.

All treatment groups were sacrificed on day 14 of the study and their splenocytes assayed for target-specific killing of the P815 cells (the averaged overall kill observed for the positive control group was about 45% at an effector to target ratio of 100:1). The serotonin-specific compounds were administered via tail vein injection (300 µg/injection) on days 5 and 7 of the study. The timing of the drug administration was selected to ensure that the T cells were activated prior to the drug treatment.

The data shown in FIG. 18A is a representative study obtained using a single group of treated mice. The assay readout is a CPM retention of tritiated thymidine of the target cells. In other words, the targets are radiolabeled with the thymidine and incubated together with the effector cells. If these cells are successfully lysed by the activated CTLs, then their CPMs are correspondingly reduced. As demonstrated by the data disclosed herein (FIG. 18A), the Methysergide treatment abrogated the allogeneic killing response.

The full treatment study is shown in FIG. 18B. The first control group was treated chronically with Cyclosporin A (n=3). The Cyclosporin A (GsA) was administered ip at a dosage of 100 µg/injection starting two days prior to the onset of the study, i.e., day-2, and the injections were continued on a daily basis for the duration of the study. The Cyclosporin A effectively prevents the T cells from initiating an activation response and is currently one of the drugs of choice for treating the complications arising from transplantation procedures. The vehicle control is buffer alone treated exactly the same as the serotonergic drug treatments. Each bar on this graph represents the data derived from an individual animal. Thus, one can clearly see that the Cyclosporin A treatment prevented the allogeneic response, while the vehicle treatment had no effect (as expected). The Methysergide (the type 1 partial antaonist/type 2 antagonist) inhibition profile was striking, as was the profile for the type 2B/2C selective inhibitor (SB206553).

These surprising data, based on in vitro results with helper T cells, was data obtained with the selective 1B/1D inhibitor and the selective 5-HT 6 inhibitor. The 1B/1D inhibitor was the most potent and effective inhibitor of the helper T cells in vitro, yet there was no apparent effect observed in vivo with respect to the CD8-dependent response. It is unclear whether or not there was reasonable bioavailability with the 1B/1D antagonist. Further, other data indicate that the selective 1B antagonist is an effective inhibitor of the CD8-dependent allograft response, consistent with the in vitro data disclosed elsewhere herein. On the other hand, the type 6 inhibitor enhanced the in vitro proliferation of the helper T cells, yet could abrogate the in vivo CD8-dependent allogeneic response.

Example 3

Role of Serotonin in Obstructive Airway Disease Including Asthma

The data disclosed elsewhere herein strongly indicate, for the first time, that the immune component of an allergic asthma response is regulated by a known neurotransmitter—serotonin. The role of serotonin in regulating immune responses was previously unknown. The data disclosed herein demonstrate that the role of serotonin in the immune response can be used to develop a novel therapeutic approach for treating human asthmatic patients.

Recent advances in the fields of Neuroscience and Immunology provide a strong basis for believing that the nervous and immune systems diverged from one another at an earlier point in evolutionary history. Moreover, the data disclosed previously elsewhere herein indicate that serotonin plays a critical role in regulating immune responses. These data indicate that serotonin-mediated signals are rate-limiting in the generation of the immunological component of allergic asthma. This discovery suggests novel useful treatments for human asthma and several other obstructive airway diseases.

In one aspect, the experiments disclosed herein demonstrate the identification of a pattern of serotonin-specific receptors present on dendritic cells (DC) and on the CD4+ helper T cell subset. These are the major cells involved in mounting an allergic immune response. RT-PCR is used to identify which of the 14 known pharmacologically distinct serotonergic receptors are present on the cells. Because serotonin plays a major role in some psychiatric disorders, in the control of vomiting, in the generation of emotional disorders, and in the control of pain associated with migraine headaches, a vast body of pharmaceutical studies used to develop drug panels that selectively modulate the individual 5-HT receptors have been previously carried out in the art. Thus, this panel of well-characterized serotonin receptor-specific drugs is available that can be used to dissect the role of individual receptors in functional in vitro assays of dendritic cell-mediated activation of CD4+ helper T cells to identify specific serotonergic signals that are rate limiting in the generation of the activation response. Further, the experiments demonstrate the use of an in vivo model of airway hyperresponsiveness to validate the utility of the potential therapeutic drugs identified by the previous assay. These experiments should aid in our basic understanding of the regulatory process involved in mounting an allergic response and the development of new therapeutic strategies for treating patients suffering from obstructive airway disease. The strategy disclosed herein is useful for identification of drugs to treat other diseases or conditions where the cells that mediate a pathological process or response require a serotonin-mediated signal such that inhibiting the signal.

The data disclosed elsewhere herein demonstrate that serotonin is a potential mediator in antigen presentation in the asthmatic lung. Further, recent advances in immunology have helped the field to realize that the basic interaction/ communication between a T cell and an antigen presenting cell is analogous to a neural synaptic junction (for a recent review see Bromley et al., 2001, Annu. Rev. Immunol. 19:375–96.). In fact, the immune system and nervous system share a number of unique features. For instance, agrin, a well-characterized glycoprotein found in neuromuscular junctions, has recently been identified as a key modulator of the immunological synapse (Khan et al., 2001, Science 292:1681–1686). Khan et al., suggest that Agrin can participate in the clustering of the T cell antigen receptor complex.

On the other side-of-the-coin, the class I major Histocompatibility complex (MHC), known to be an important glycoprotein in the generation of an immune response, has recently been shown to play a pivotal role in the neural synapse (Huh et al., 2000, Science 290:2155–2159). Huh et al., demonstrated that the MHC class I is involved in the activity-dependent remodeling and plasticity of connection in the developing and mature nervous system. Moreover, the L1 neural adhesion protein has now been shown to be an important protein in the T cell activation response (Balaian et al., 2000, Eur. J. Immunol. 30:938–43). Major neurotransmitters, such as dopamine and norepinephrine, originally characterized because of its contribution of the "fight or flight" response, also modulate immune responses through the expression of their cognate receptors on lymphocytes (Santambrogio et al., 1993, J. Neuroimmunol. 45:113–119; Kohm and Sanders, 2000, Immunology Today 21:539–542; Saha et al., 2001, Neuroimmunomodulation 9:23–33). Taken together, these data suggest that the immune system and nervous system diverged from one another at some early point on the evolutionary time scale. Further, the data disclosed elsewhere herein, showing that serotonin plays a rate-limiting role in mounting an immune response, indicate the presence of serotonin-responsive receptors on the surface of lung dendritic cells and a critical regulatory role for serotonin in initiating asthmatic responses in the lung.

Upon encountering an inhaled antigen, airway dendritic cells (DCs) migrate to the draining lymph nodes of the lung, upregulate expression of costimulatory ligands, and interact with naïve CD4+ T lymphocytes, initiating a primary immune response (Wills-Karp, 1999, Annu. Rev. Immunol. 17:255–81). The data suggest that dendritic cell/lymphocyte interaction is regulated in response to serotonergic signaling. Although very little is known about the presence or absence of 5-HT receptors on dendritic cells, the data disclosed elsewhere herein strongly suggests their presence. Thus, dendritic cells are probed for expression of serotonergic receptors, via RT-PCR. The data disclosed herein demonstrate use of immature murine myeloid dendritic cells for the initial studies. The mRNA levels for the various 5-HT receptors in the immature cells versus dendritic populations that have been matured in the presence of LPS and IL-4 are compared. Additionally, the receptor arrays present on the resting/naïve and activated CD4+ helper T cell populations are detected. Data disclosed previously elsewhere herein with respect to human peripheral blood lymphocytes, indicate the presence of a variety of different 5-HT receptors that are up and down regulated in response to activating signals, such as Con A.

The 5-HT receptor (s) present on the cell is identified, then an appropriate serotonergic receptor modulating agents to selectively target 5-HT receptors present on dendritic cells and the CD4+ helper T cell subset. The DCs are used as antigen-presenting cells in a mixed lymphocyte reaction (MLR). In addition to monitoring DNA synthesis via $^3$H-Thymidine incorporation, the assay monitors for the production of type 1 and type 2 markers (IL-12 and IL-4, respectively).

An in vivo murine model of ovalbumin-induced airway hyperrsponsiveness (AHR) is used herein. This assay characterizes the effects of selectively blocking serotonergic signals in a whole animal model of asthma. Also, mice with different alleles of expressed 5HTR are tested for different AHR patterns, eventually by using congenic strains for critical 5HT receptors.

The data disclosed previously elsewhere herein demonstrate that a variety of distinct serotonin-specific receptors are present on resting lymphocytes and that their expression pattern changes upon activation. Signals generated from the 5-HT 2C receptor appear to be rate-limiting for the activation of both murine and human CD4+ helper T cells as well as CD8+ cytotoxic T cells. Selective inhibition of the 1B/1D receptors has a potent effect on the proliferation of both human and murine helper T cells, but no effect on the activity of the cytotoxic T cells. Selective inhibition of the 5-HT 6 receptor, on-the-other-hand, has the opposite effects.

In terms of the asthmatic response, the dendritic cells are the most likely antigen presenting cells for the allergen. In turn, these cells activate the CD4+ helper T cells, inducing a Th2-type response. The experiments disclosed elsewhere herein characterize the expression pattern of the serotonergic receptors on both the DCs and the CD4+ helper T cells. Th data based disclosed previously elsewhere herein indicate that the 5-HT 1B and 1D receptors are present on the CD4+ T cells, but not on the CD8+ T cell subset. The data suggest that there is a specific 5-HT signal that is absolutely required for the activation and maintenance of the T cell-mediated allergic response. The data disclosed elsewhere herein demonstrated that by selectively withdrawing the appropriate receptor signal, apoptosis can be induced in the activated T cell population, resulting in the functional deletion of these cells from the repertoire. This should disrupt the feedback pathway that leads to the degranulation of the eosinophils and mast cells and cause a "short circuit" in the asthmatic response.

The distribution of 5-HT receptors on immature and mature DCs as well as the distribution of receptors on the CD4+ helper T cell subset, responsible for driving the production of IL-4 and IgE during an asthmatic response are defined. Currently, there is no available information on the distribution of serotonin-specific receptors on any of these cell types. This is a direct extension of data disclosed elsewhere herein and provides a basis for understanding the signaling process that is responsible for differentially driving a CD4-dependent versus a CD8-dependent immune response.

As mentioned above, the expressed 5HT receptors in immature myeloid dendritic cells and dendritic cells that have been matured in the presence of either LPS and IL-4 or in the presence of LPS and IL-12 are identified, as are the expressed receptors in CD4+ helper T cells. These studies are performed with BALBc mice using negative selection techniques, using kits supplied by StemCell Technologies Inc (Vancouver, British Columbia), for the enrichment of the dendritic cells and helper T cells. For the dendritic cell populations, the murine hematopoietic progenitors are isolated from a bone marrow harvest (using the femur and tibia) flushing with PBS containing 5% FBS and 1 mM EDTA. After centrifugation, the nucleated cells are resuspended at $5 \times 10^7$ cells/ml in the flushing media plus 5% normal rat serum. After incubation for 15 minutes at 4° C., the cell suspension is treated according to the manufacturer's instructions for enriching the dendritic cell precursors (using the StemSep™ kit). The dendritic precursor is cultured in 1000 units/ml murine recombinant GM-CSF for 5 days according to the procedures described by Pulendran et al. (1999, Proc. Natl. Acad. Sci. USA 96:1036–1041). The maturation of these cells is performed according to the procedures described by Pulendran et al., 1999.

For the enrichment of the CD4+ T cells, the StemSep™ cell separation system is also used using protocols provided by the manufacturer. Briefly, whole mouse spleen cell suspensions are used in this procedure. The non-specific binding to the Fc receptors is blocked using normal rat serum for the murine cell preparations. For the naïve T cell purifications, the specific biotinylated antibody is added first. After samples are incubated on ice for 10–30 minutes, the appropriate lymphocyte enrichment cocktails (CD8+, CD19+, etc.) is added (30 minutes on ice), followed by the addition of magnetic colloid suspension (30 minutes on ice). During this incubation, the unwanted cells bind to tetrameric antibody coupled to the magnetic beads. The cell-antibody complexes are then loaded on the prewashed separation column (placed inside the magnet, provided by the manufacturer). The columns are washed with 3× column volume and the flowthrough, which now contains the desired cell populations, is collected. The typical purity of the enriched cells is 90–99% for most of the cell subtypes. The purity of the recovered enriched cells is verified, if necessary, by the FACS analyses using the core flow cytometry facility at the MCP Hahnemann University. The StemSep™ purification system is used to fractionate up to 1.5× $10^{10}$ total cells, therefore providing sufficient amounts of cells, required to produce a subset-specific cDNA library.

Total cellular RNA is extracted using Qiagen RNAeasy minipreps, according to the manufacturer's instructions. RNA samples are quantitated by EtBr staining of the gel and approximately 1 microgram of each RNA sample is used for the cDNA synthesis. cDNA synthesis is performed with Qiagen Reverse Transcriptase according to the manufacturer's instructions, using oligoT$_{12-18}$ primer. The resulting cDNA is a template in PCR (Taq DNA polymerase, Sigma) using 5-HT receptor specific primers. PCR conditions are: 95° C. for 45 sec., 61.5° C. for 45 sec., 72° C. for 45 sec. 35 cycles followed by 10 min. extension step (72° C.). PCR products are analyzed by 3% agarose gel electrophoresis (TAE buffer). For additional verification, PCR products are subjected to Southern Blot Hybridization, using radioactively labeled receptor-specific internal oligonucleotides as probes.

PCR products are transferred from the agarose gels to HyBond membranes and hybridizations are performed as described in the Current Protocols In Molecular Biology. Briefly, membranes are pre-blocked in 6× SSC, containing 10× Denhardt's solution, 0.5% SDS, 1 microgram/ml polyA, and 100 micrograms/ml of SS DNA. 20 pmol of radioactively labeled probe are added per hybridization and incubated overnight (at 73° C.). The next day the excess probe is washed away and the membranes are exposed to Kodak film.

For a typical cDNA library, 0.5 to 2 micrograms of the total cellular RNA is required. The RNA recovery from the mouse spleen cells is approximately 3.5 micrograms from $1 \times 10^6$ cells (350 micrograms per spleen). One mouse spleen is sufficient to make a completed set of cDNA libraries for one subset of cells (this results in total of at least 7–10 mice for completion of this experiments).

The functional dependence of selective 5-HT receptor signals is assessed in an in vitro activation of CD4+ helper T cells. Mature dendritic cells from a C57BL/6J mouse are purified as described above and used to allogeneically stimulate lymphocytes derived from a BALBc mouse. Cell activation is measured as a result of the incorporation of $^3$H-Thymidine into newly synthesized DNA. Levels of IL-4 and IL-12 are determined from cell-free tissue culture supernants by ELISA (R&D Systems, according to the manufacturer's instructions).

Serotonergic agonists and inhibitors are selected from the manufacturer (Tocris Cookson Inc., Ellisville, Mich.). The receptor-specific modulators are added to the assay either at time 0 (at the start of the assay) or at time=48 hours. In general, there is a two-day delay between the delivery of the initiating activation signal and the beginning of the first round of cell division. The data disclosed previously elsewhere herein demonstrate that the drugs have fundamentally different effects on the outcome of the assay depending on whether they have been added at t=0 or t=48 hrs. The other variable of drug addition that is addressed is the effect of drugs that have been added at time 0, then washed off at time=2 hrs. This is especially important for testing the effects of many of the 5-HT-specific agonists. Most of the agonist desensitize the receptors when left in prolonged contact (resulting in apparent inhibition). The drugs are initially tested at a concentration range of 0.1, 1, 10 and 100 micromolar.

To obtain the BALBc lymphocytes, spleens are harvested from BALBc mice (Jackson Laboratories). The spleens are mashed in the spin medium (RPMI 1640 Medium (GibcoBRL) supplemented with 2% Fetal Bovine Serum (Sigma), 1% Pen-Strep (Sigma) and 1% L-Glu (BioWhittaker)) to obtain a single-cell suspension. The cells are centrifuged for 10 minutes at 1200 RPM, and the supernatants removed. Red Blood Cells (RBC's) are lysed with ACK buffer (as described in Colligan et al., 1999, In: Current Protocols in Immunology, Section 3.1.3–3.1.5). The remaining cells are resuspended in the spin medium, and loaded onto nylon wool column to remove the adherent cells. The cells are incubated on the column (5% CO2, 37° C.) for approximately 2 hours. The non-adherent cells are washed off the column using spin medium, centrifuged, and resuspended in Sensitization medium (RPMI 1640 Medium supplemented with 10% Bovine Serum, 1% Pen-Strep and 1% L-Glu, -MKE).

The mixed lymphocyte reaction (MLR) is performed essentially as described in Current Protocols in Immunology (Section 3.12.6–3.12.7, 1999). That is, the enriched, matured dendritic cells from C57/B6J mice are used as stimulators. Primary lymphocytic cells from the BalbC/BYJ are used as the responders. Drugs are pre-plated onto 96 well, U-bottom plates. All experimental conditions are assayed at least in triplicate. 100,000 of C57/B6 cells in RPMI medium, supplemented with 10% FBS, will be plated into each well. 200,000 of BalbC/BYJ cells will be plated over the stimulator cells, to a final volume of 200 microliters/well. Background controls received either no BalbC cells, or no C57/B6 cells. 1 microCi of tritiated thymidine will be added to each well after 4 days, and the plates were harvested 12 hours later.

Data points derived from these assays are evaluated by the Mann-Whitney U test, Wilcoxon's signed-rank test for paired data, Student's t test and Spearman's rho correlation using JMP Statistics Guide (SAS Institute Inc., Cary, N.C.).

Finally, the assays describe herein provide a means of validating data obtained from the in vitro allogeneic stimulation assay. The airway hyperresponsiveness (AHR) model in BALBc mice is used to validate our drug activities. In basic terms, this model is set-up by immunizing the mice with ovalbumin (OVA) in alum over the course of two weeks. This initiates a primary immune response. At the height of this response, an aerosol of OVA is used to drive the presentation of the antigen by DCs in the lung and skew the response toward a Th2-type response. Once the mice have been sensitized, a dose of methacholine is administered to trigger the asthmatic-like response.

Ro 04–6790—a selective antagonist of the 5HT 6 receptor. Signals mediated through this receptor are positively coupled to adenyl cyclase. Thus, stimulation of the 5HT 6 receptor results in the increase of cellular cAMP, which will block the T cell activation pathway. Antagonizing this signal can alleviate this impediment and facilitate the immune response.

1-(1-Naphthyl) Piperazine—a selective agonist of the 5HT 1 class of receptors. These receptors are negatively coupled to adenyl cyclase. The stimulation of these receptors can cause a decrease in the cellular levels of cAMP and thereby aid the immune response.

Troposetron—a selective antagonist of the 5HT 3 receptor. Simulation of this receptor should aid in the flux of Ca2+ into the cell thereby facilitating the immune response. Antagonism of this signal can hinder the activation response.

WAY 100635—a selective antagonist of the 5HT 1A receptor. As previously mentioned, the type 1 receptor negatively couples to adenyl cyclase. In vitro, this drug significantly inhibits the activation response. The inhibitory effects of this drug are most pronounced when administered early in the activation response.

SB 206553—a selective antagonist of the 5HT 2B/2C receptors. The 5HT type 2 receptors are positively coupled to the activation of protein kinase C. The in vitro data disclosed elsewhere herein indicate that withdrawal of the 5HT 2B/2C signals at any point during the activation response results in the immediate cessation of proliferation (apparently, and without wishing to be bound by any particular theory, by means of inducing programmed cell death.

SB 242084—a selective antagonist of the 5HT 2C receptor. This compound has been selected to determine whether or not any advantage is gained by blocking the 2B and 2C receptor rather than the 2C receptor alone.

The drugs are administered at 300 microgram/dose in PBS via a tail vein injection and this dose and route of administration is based on the data disclosed previously elsewhere herein. One set of mice receive the drugs 3 days prior to the administration of the methacholine and one set of mice receive the drugs 3 hours after the administration of the methacholine. The time points of drug addition were selected to ensure that the T cells were fully activated at the time of the drug administration. Ideally, the activated T cell population is deleted, creating a functional hole in the immunologic repertoire. The study is divided into 4 major groups. The first 2 groups, each consisting of 3 mice each, serve as vehicle control. For the drug treated groups, 5 mice are used per drug. Thus, each group consists of 30 mice each. The numbers of mice in each group are evaluated by the Mann-Whitney U test, Wilcoxon's signed-rank test for paired data, Student's t test and Spearman's rho correlation using JMP Statistics Guide (SAS Institute Inc., Cary, N.C.) thereby ensuring the statistical significance of the data.

BALBc mice are immunized as described by Brewer et al. (1999, Am. J. Respir. Crit. Care Med. 160:1150–1156), with OVA (10 micrograms, Sigma Grade III, St. Louis, Mo.) plus 1 mg $Al(OH)_3$ in 0.2 ml saline, i.p., twice over the course of two weeks. 7–10 days after the second immunization, the mice are exposed to 6% wt/vol aerosolized OVA (delivered via an ultrasonic nebulizer). Exposure of mice for 60 minutes daily to the aerosol allergen for 7 days leads to airway sensitization.

RT-PCR primers are as described elsewhere herein for detecting various serotonin receptor subtypes, and RT PCR is performed as described elsewhere herein.

Asthma morbidity and mortality are disproportionately higher in minority children. There is inadequate knowledge about the genetic and environmental triggers of asthma. It is known that ETS (environmental tobacco smoke) contributes to early onset of asthma and is a risk factor for asthma severity (Malveaux and Fletcher-Vincent, Environmental Health Perspectives, 1995). The data disclosed herein contributes to the study of genetic factors in an art-recognized mouse model for human asthma that shares many of the features of human asthma, in order to understand the role of certain gene products that are known to be important in transduction of the allergic signal to lymphocytes, and the bronchoconstriction signals to lung smooth muscle. This mouse model system for asthma is strongly influenced by the genetic background of the mice, and as such, may illuminate the genetic constituents necessary for disease to occur both in mice, and eventually, in humans.

Using mice as the model system, the allergic and obstructive consequences of allergen exposure can be assessed in several genetically-manipulated animals. The data obtained may reveal new roles for histamine in the initial phases of allergen sensitization and also in the role of histamine in the long term secondary responses. Given the exploding rates of asthma in children, e.g., asthma is now the leading cause of school absence among children of color in impoverished urban neighborhoods (Kinney et al., 2002, Am. J. Public Health 92:24–26), any better understanding of the initial stages of allergen sensitization and consequent airway disease can lead to new targets for drug development, or at least an improvement in the timing of such therapy. Because antihistamines are considerably weaker than other drugs at ameliorating endstage asthmatic symptoms, their role in initial phases of disease can be subtle; such effects are best studied in an animal model where genetic manipulation and induction regimens are controlled.

Example 3

Apoptosis Induction in Multiple Myeloma Cells Relating to Serotonin Receptors Multiple myeloma (MM) is the second most common hematologic malignancy in the United States, with approximately 15,000 new cases diagnosed each year. The disease is progressive and typically fatal, accounting for 15% of all deaths from malignant white cell disease and 2% of all cancer deaths in Western countries. Despite considerable advances in the understanding of the pathophysio Logy of multiple myeloma, the molecular basis of the disease has remained elusive.

Clinically, multiple myeloma represents a B-cell neoplasm characterized by bone marrow infiltration of malignant plasma cells, which secrete monoclonal immunoglobulin fragments. Patients typically present with lytic bone lesions at multiple sites along with resultant hypercalcemia, due to the myeloma cells' ability to both stimulate osteoclastic bone resorbtion and inhibit osteoblastic remodeling. The disease itself proceeds through three distinct phases: an inactive phase in which mature, nonproliferating, malignant cells predominate; an active phase in which a small percentage of less differentiated, proliferative, plasmablastic cells appear; and a fulminant phase in which an extramedullary proliferation of immature plasmablastic cells predominates. The presence of these distinct disease phases lends support to recent proposals of a stepwise malignant transformation during multiple myeloma pathogenesis.

Karyotypic changes are detected in virtually all MM cases, with translocations most commonly involving illegal switch rearrangements of immunoglobulin heavy chain loci with various partner genes. Aberrant expression of oncogenes (c-myc, ras), tumor suppressor genes (p16, p15) and regulators of apoptosis (BCL-2, Fas) have also been implicated as being involved in the complex cascade of events thought to contribute to the transformation of a follicular center B-cell to a malignant plasmablastic clone.

The initial clone from which the myeloma cells are derived is believed to be a post-germinal center B-cell. The expression of rearranged immunoglobulin genes which are extensively hypermutated suggests that the initial oncogenic events occur after, or do not interfere with normal, long-lived plasma cell differentiation. A striking feature of multiple myeloma is the tendency for the transformed plasmablastic cell to reside in the bone marrow during the main course of the disease, where the micro-environment can provide the appropriate cytokines (i.e., IL-6 and IL-10) and adhesion molecules for the growth and survival of a slowly dividing tumor cell population. However, in the fulminant phase of the disease, the myeloma cells develop a stromal-independency, and extramedullary proliferation of the plasmablasts ensues.

MM is best viewed as a heterogeneous disease, with a different biology, prognosis, clinical course and response to therapeutic intervention in individual patients. An understanding of not only the events leading to the establishment of a stable malignant plasma cell population, but also the signals which drive this cell population to clonally expand and the factors necessary for these cells to escape stromal dependency in establishing extramedullary disease, are crucial to the understanding central mechanisms underlying disease progression.

If the MM cells are able to escape stromal dependency and clonally expand outside of the bone marrow, then it stands to reason that these cells must self-produce all of the elements required for survival and expansion. Furthermore, if these cells are still dependent upon serotonergic signaling pathways, then the MM cells have, most likely, acquired the ability to synthesize and release their own serotonin. The data disclosed herein provides a novel therapeutic strategy for treating MM patients in which 5HT antagonist(s) are used to suddenly withdraw an essential signal (the serotonergic signal) required for the constitutive activation of the MM cell and, thereby, induce apoptosis.

In sum, MM is a cancerous condition of the mature (terminally-differentiated) B cells. This type of B cell should normally be found within the circulatory system. One of the hallmarks of MM is that these (cancerous) B cells return to the bone marrow, where they do substantial damage. Without wishing to be bound by any particular theory, the process of becoming a 'fully developed' cancer cell occurs in discrete steps. As the B cell cancer develops in an afflicted individual, the cancerous B cells develop survival modes that are independent of their local environment. Currently, there is no effective means of treating MM patients, other than bone marrow transplants. Most patients initially respond to a treatment regimen of corticosteriods, such as dexamethasone, but in almost all cases, the disease develops a complete resistance to these drugs. Most often, a diagnosis of multiple myeloma is synonymous with a death sentence. The methods disclosed herein exploit the growth independence of the cells and the discovery that the cell cycle response requires signaling via a serotonin receptor such that if the signal is inhibited, the cell dies.

That is to say, taken together with recent developments in the field, the data disclosed elsewhere herein strongly indicate that the immune and nervous systems diverged from one another during evolutionary development. Moreover, the activation pathways of the immunologically relevant cells appear to depend upon signaling induced through serotonin. Thus, these data suggest, without wishing to be bound by any particular theory, that these cancer cells cannot depend upon an external source of serotonin and, therefore, must have turned-on the synthetic machinery for producing their own stores of serotonin. It is well established that all activated or proliferating cells depend on the fidelity and timing of growth/activation-related signals in order to maintain their integrity. Sudden withdrawal of a rate-limiting signal, especially in cancer cells, results in the activation of a programmed cell death pathway (apoptosis). Based on the data disclosed herein, and without wishing to be bound by any particular theory, the three most likely rate-limiting signal sources (and, hence, the three most likely targets), are the 5HT1, 5HT2 and/or 5HT4 receptors. This study is intended to examine the effects on MM cells of withdrawing these signals through the use of a selective, non-competitive antagonists (or cocktail of antagonists) of these receptor signals.

The following experiments demonstrate the dependence of multiple myeloma cells (malignant plasma cells) on signals induced through serotonin (5-HT), in an in vitro system. The human multiple myeloma cell line, RPMI 8226, was the in vitro system employed. Initially, assays of cell viability and cell proliferation were used to monitor the effects of numerous 5-HT receptor modulating agents on RPMI 8226 cells in culture. After identifying compounds that affected the growth and viability of the myeloma cell line, experiments were designed to characterize the mechanism though which some of the receptor modulating agents induced cell death in the RPMI 8226 cells. Specifically, affected cells were assayed for hallmarks of apoptosis (morphology, DNA fragmentation, and extracellular phosphatidylserine expression.)

It is clear, as the data disclosed herein demonstrate, that myeloma cells are dependent on signaling through the serotonin receptors. Most notable is the effect of withdrawal of the 5-HT1B receptor signal. In the absence of signal from the 5-HT1B receptor, the myeloma cells underwent a violent cell death. Morphologically, the cell death was different than traditional apoptosis, in which the cells pyknose, condense their nuclei and form membrane blebs. Instead, upon the withdrawal of the 5-HT1B signal, the cells swelled drastically, burst, and the culture was virtually 100% dead within 3 hours. However, upon further characterization, these cells demonstrated certain characteristic traits typical and/or associated with apoptosis (e.g., internucleosomal DNA fragmentation and phosphatidylserine expression on the cell surface). These data demonstrate therefore that withdrawal of a serotonin signal mediates cell death via apoptosis and/or an apoptosis-like process.

Cell Lines

The human plasmacytoma (multiple myeloma) cell line, RPMI 8226 (American Type Culture Collection, Manassas, Va.), was cultured in RPMI 1640 supplemented with 10 mM HEPES, 1 mM sodium pyruvate, 4.5 g/L glucose, 1.5 g/L bicarbonate and 20% FBS (non-heat inactivated).

Cell Proliferation Assays

Cell proliferation was assayed by three methods—Trypan Blue Exclusion was used to quantify the number of viable cells in culture; 3-(4,5-dimethylthiazol-2-yl)-2,5-diphenyl tetrazolium bromide (MTT) reduction was used to assay mitochondrial activity (and thus cell viability); and $^3$H-Thymidine uptake was employed to assay for active DNA synthesis.

In vitro Testing of 5-HT Receptor Modulation

The following 5-HT receptor modulating compounds were tested for their effects on RPMI 8226 cells in vitro cultured at the described densities and across the indicated concentration ranges.

TABLE 2

| Compound | Primary Action |
| --- | --- |
| WAY 100635 | 5-HT(1A) Receptor Antagonist |
| 8-OH-DPAT | 5-HT(1A) Agonist |
| SB 216641 | 5-HT(1B) Receptor Antagonist |
| L 694247 | 5-HT(1B/1D) Receptor Agonist |
| GR 55567 | 5-HT(1B/1D) Receptor Antagonist |
| BRL 54443 | 5-HT(1E/F) Receptor Agonist |
| Methysergide | 5-HT(2) and 5HT(1) Antagonist |
| LY 53857 | 5-HT(2A/2B/2C) Receptor Antagonist |
| SB 206553 | 5-HT(2B/2C) Receptor Antagonist |
| MDL 11939 | 5-HT(2A) Receptor Antagonist |
| SB 242084 | 5-HT(2C) Receptor Antagonist |
| DOI | 5-HT(2A/2C) Agonist |
| RO 046790 | 5-HT(6) Receptor Antagonist |
| SB 269970 | 5-HT(7) Receptor Antagonist |
| HMBA | Induction of terminal differentiation in cells |

DNA Fragmentation

Cells ($8 \times 10^5$) were washed with ice-cold PBS following experimental treatments and pelleted by centrifugation (500×g, 5 min). Cell pellets were incubated for 5 minutes on ice in lysis buffer (1% IGEPAL-CA630, 20 mM EDTA, 50 mM Tris-HCL, pH 7.5). Lysates were centrifuged at about 1,600×g for 5 minutes. 50 µL of lysis buffer was added to the supernatant. The extract was brought to 1% SDS and treated for 2 hours with 5 µg/µAL Rnase A (57° C.) followed by treatment with 2.5 µg/µL proteinase K for 2 hours (37° C.). After digestion of RNA and protein, half volume of 10 M ammonium acetate was added and the DNA was precipitated using 2.5 volumes of ethanol, washed in 70% ethanol, air-dried, and dissolved in TE buffer. DNA fragments were separated by electrophoresis in 1.5% agarose gels using a protocol adapted from Siegel et al. (1998, Proc. Natl. Acad. Sci. USA 95:162–166).

Flow Cytometry

Early apoptotic cells were detected by co-staining cells previously exposed to each experimental condition. Briefly, cells were incubated during a time course in the presence of various concentrations of each experimental or control apoptosis inducing agent as set forth elsewhere herein. After incubation, the cells were washed with ice-cold PBS, stained with Annexin V-Alexa flour 488 and Propidium Iodide (Molecular Probes, Eugene, Oreg.) and analyzed by dual-color flow cytometry. Annexin $V^+$ and $PI^-$ cells were considered as early apoptotic cells. The known terminal differentiator of myeloma cells, HMBA (hexamethylene-bis-acetamide), and the topoisomerase inhibitor, camtothecin, were used as positive controls for apoptosis at 5 mM and 2 µM, respectively.

Three separate indicators of cell proliferation were employed to study the effects of 5-HT receptor modulating agents on the human multiple myeloma cell line, RPMI 8226. Cells were plated at 4 separate densities and were treated with LY53587 (an antagonist of the 5-HT2A/2B/2C receptors) at a range of concentrations. The exclusion of trypan blue dye was used as an indicator of cell viability. Cell numbers were then plotted against the concentration of drug added.

MTT reduction was also used as an indicator of cell viability (more specifically, mitochondrial activity). Absorbance values at $OD_{570}$ were then plotted against drug concentration. Finally, DNA synthesis was assayed, through the measurement of $^3$H-thymidine uptake, and counts per minute (CPMs) were plotted against drug concentration. All three assays yielded clear dose-response curves. Furthermore, the shapes of the curves were not dependent on the assay used (i.e., no method was better than another in assaying the effects of the drug on the cell population) (see FIGS. 19A, 19B, and 20A–D).

The effects of antagonists to different subtypes of the 5-HT2 receptors was examined by measuring DNA synthesis via $^3$H-Thymidine uptake (FIG. 21).

Various other 5-HT receptor modulating compounds have also been assayed for their effect on RPMI-8226 cells. Cell proliferation was again measured through the monitoring of thymidine uptake, as a surrogate marker of DNA synthesis. FIG. 22 demonstrates the effects of each of these 5-HT receptor antagonists or agonists, expressed as percent proliferation relative to vehicle treated controls. Antagonism at the 5-HT1B receptor produced the most marked inhibition of the myeloma cells across the broadest concentration range. Treatment of the cells with the 5-HT1B/D specific antagonist was not as efficient at inhibiting the cell growth as was the 5-HT1B antagonist alone.

Low dose-titration of the various agonists and antagonists of the 5-HT receptors were tested against the human Multiple Myeloma RPMI-8226 cells (FIGS. 23, 24 and 25). As can be seen form these data, low doses of the highly selective 5-HT 1B antagonist (SB216641) completely inhibited the growth of the cancer cells. Additionally, strong inhibition of growth was observed with using Methiothepin (a general 5-HTR 1, 2, 6 and 7 antagonist) or the highly selective 5-HT 2C antagonist, SB 242084. Thus, the data disclosed herein clearly demonstrate that growth of Multiple Myeloma cells can be inhibited by the selective withdrawal of either the 5-HT 1B receptor signal or the 5-HT 2C receptor signal.

The mechanism through which the withdrawal of 5-HT receptor signaling induces cell death in RPMI 8226 cells was explored further. Specifically, it was determined whether any of the hallmark events of apoptosis occurred throughout the cell death occurring upon the 5-HT1B/D signal withdrawal. 5-HT receptor antagonists which were known to induce cell death in the RPMI 8226 cell line, as shown by trypan exclusion cell counting data, were assayed for their ability to induce internucleosomal cleavage in the dying cells.

The results of this experiment are illustrated in FIG. 26. The data disclosed herein demonstrate that the terminal differentiator, HMBA (hexamethylene-bis-acetamide), which is known to induce apoptosis in a percentage of myeloma cells (approximately 30%) shows a very faint DNA ladder. However, withdrawal of 5-HT receptor signaling with drugs specific for the 1B/D, 2A/B/C, and 2B/C receptors, produced clear DNA laddering as early as 24 hours with some compounds.

Co-staining of cells with AnnexinV and propidium iodide after treatment with the 5-HT(1A), 5-HT(1B), and 5-HT(1B/D) antagonists was also used to characterize the cell death occurring upon signal withdrawal. Annexin V binds specifically to phosphatidylserine, a membrane lipid expressed only on the internal membrane leaflet of viable cells. However, upon apoptosis, phosphatidylserine is no longer localized to the inner membrane leaflet and can be used as a marker for one of the very earliest events in apoptosis. The dye propidium iodide, on the other hand, gains access to the cytoplasm and nucleus only once the membranes have been compromised, an event associated with late apoptosis or necrosis. Therefore, dual color flow cytometry was used to identify populations of cells which were Annexin$^+$ but PI$^-$ indicating the cell death occurring was due to apoptosis.

The analysis of the flow cytometry data disclosed herein clearly demonstrates that the cells became apoptotic in a dose and time dependent manner upon treatment of RPMI-8226 cells with an 5-HT(1B) antagonist, and not when 5-HT(1A) or 5-HT-(1B/D) specific antagonists were used, at the time points assayed (FIG. 27). That is, treatment of the cells with a type 1B/D antagonist causes a shift in the cells that are stained by annexin. Further treatment demonstrated the increased staining of the cells by propidium iodine, demonstrating that the cells were not only dead, but were lysed or necrotic.

The data disclosed herein (e.g., FIGS. 28 and 29) demonstrate conclusively that withdrawing either the 5-HT 1B receptor signal (FIG. 28) or the 5-HT 2C receptor signal (FIG. 29) in the Multiple Myeloma cells results in a classical apoptosis as is evidenced by condensed and fragmented chromatin structures shown in these micrographs. The results suggest that the growth of the RPMI-8226 cells is dependent on signaling through both the 5HT(1B) and 5HT(2C) receptors, and withdrawal of signal at either of the two receptors with the specific 5HT receptor antagonists used, i.e., SB 242084 (2C) or SB 216641 (1B), induced programmed cell death comparable to that induced by the topoisomerase I inhibitor, camptothecin. However, the extent and time course of apoptosis induced by the two compounds differed. These data suggest, without wishing to be bound by any particular theory, a possible mechanistic difference in apoptosis induction for the two serotonin receptors subtypes.

The data disclosed herein strongly suggest that malignant plasma cells are dependent on signals transduced through the 5-HT receptors, and that the withdrawal of signals at individual receptors produces markedly different responses. Furthermore, inhibition of single receptor signals produces different responses than the inhibition of a combination of receptors. Inhibition of the essential signals transduced via these 5-HT receptors in malignant plasma cells can serve an effective treatment of multiple myeloma where, prior to the present invention, an effective treatment to this disease was not available in the art.

Furthermore, the data disclosed elsewhere herein clearly demonstrate that a variety of cell processes are involved in, or mediated by, serotonergic signaling. More particularly, the data demonstrate that blocking of 5-HTR1B or 1B/1D receptor mediates apoptosis in a cell line (RPMI 8226), which is an art-recognized model for multiple myeloma. Thus, the present invention includes methods of affecting a cellular process such as, but not limited to, cell proliferation and apoptosis of a cell. This is because, as demonstrated herein, various non-neural cells comprise a serotonin receptor on their surface and, when the serotogenic signal is blocked from signaling, which is crucial for cell survival, the cell is affected and, eventually, the lack of 5HTR signaling causes cell death.

Thus, the present invention provides an effective method for mediating cell death or inhibition of cell growth in a target cell of interest by inhibiting transmission of a serotonin signal otherwise transmitted via a serotonin receptor on the cell surface. Accordingly, the presence of a serotonin receptor on a cell of interest can be readily determined using methods well-known in the art and/or taught herein. Further, it can be determined whether withdrawal of a serotonin signal to that cell is deleterious to the cell, as demonstrated herein for RPMI8226 cells, and various inhibitors of serotonin signaling can be used to specifically inhibit the signal thereby killing the cell or inhibiting the functioning, growth and/or division thereof, while not affecting other cells that either do not express a serotonin receptor or which express a different serotonin receptor than that expressed on the surface of the target cell.

The surprising results disclosed elsewhere herein were not suggested by the prior art probably since, without wishing to be bound by any particular theory, previous studies relating to inhibition of serotonergic signaling were performed in neural and/or muscle cells, which cells do not grow or divide and which do not constitutively go through the cell cycle. Rather, contacting muscle and neural cells with 5-HTR antagonists mediates cell depolarization and the effect of inhibiting serotonergic signaling on cell cycle process, including its effect on immune cells to modulate the immune response, was entirely unexpected, unprecedented, and previously unobserved. Therefore, the present discovery that signaling via a serotonin receptor present on a cell is required for cell proliferation and/or survival, provides an important novel tool for the development of therapeutics for use in diseases or conditions where inhibiting growth of a cell comprising a serotonin receptor can provide a therapeutic benefit.

Example 4

Assay Relating to Cell Changes Mediated by Inhibition of Signal Transmission via Serotonin Receptors The data disclosed elsewhere herein demonstrate, for the first time, that inhibiting transmission of a signal via a serotonin receptor can induce, mediate, or is associated with detectable change in a cell. More specifically, cells contacted with certain serotonin antagonists exhibited changed cell morphology and/or other altered physical characteristics which were detectable by a variety of methods known in the art, including, light microscopy.

Briefly, cells were incubated with a 5-HTR antagonist (e.g., a selective type 1B inhibitor SD 216641) and the effects of treatment were assessed after 24 hours. Changes is cell morphology, e.g., an increase in cell size, were readily detected (FIG. 30). These data demonstrate that the effect of serotonin signal inhibition can be assayed by assessing changes in cell shape, morphology, and the like, using methods well known in the art, or to be developed in the future. For instance, detection of cell changes can be assessed using optical instruments (electron and light microscopy, as well as fluorescence activated cell sorting, and the like), or any other device that assesses and detects changes in cell size, density, morphology, and the like. Such devices are well known in the art and are not recounted here.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing apoptosis in a multiple myeloma cell, said method comprising inhibiting transmission of a serotonin signal via a serotonn receptor on said cell wherein said inhibition induces apoptosis, and further wherein said inhibition comprises contacting said cell with an effective amount of a scrotonin type 1B receptor antagonist, thereby inducing apoptosis in said cell.

2. A method of inducing cell death in a multiple myeloma cell, said method comprising inhibiting transmission of a serotonin signal via a serotonin receptor on said multiple myeloma cell wherein said inhibition induces death of said cell, further wherein said inhibition comprises contacting said cell with an effective amomt of a serotonin type 1B receptor antagonist, thereby inducing death of said cell.

3. A method of inducing apoptosis in a multiple myeloma cell expressing a serotonin receptor, said method comprising contacting said cell with an effective amount of a serotonin type 1B receptor antagonist, thereby inducing apoptosis in said cell.

4. The method of claim 3, wherein said antagonist is selected from the group consisting of SB216641, methiothepin, and methysergide.

5. The method of claim 1, wherein said antagonist is selected from the group consisting of SB216641, methiothepin, and methysergide.

6. The method of claim 1, wherein said effective amount ranges from about 200 nanomolar to 20 micromolar.

7. The method of claim 2, wherein said antagonist is selected from the group consisting of SB216641, methiothepin, and methysergide.

8. The method of claim 2, wherein said effective amount ranges from about 200 nanomolar to 20 micromolar.

9. The method of claim 4, wherein said effective amount ranges from about 200 nanomolar to 20 micromolar.

* * * * *

```
                       SEQUENCE LISTING

<160> NUMBER OF SEQ ID NOS: 30

<210> SEQ ID NO 1
<211> LENGTH: 35
<212> TYPE: DNA
<213> ORGANISM: Homo sapiens

<400> SEQUENCE: 1
ctgcagaacg tggccaatta tcttattggc tcttt                            35

<210> SEQ ID NO 2
<211> LENGTH: 34
<212> TYPE: DNA
<213> ORGANISM: Homo sapiens

<400> SEQUENCE: 2
gtggagtact cagctaaaag gactcccaag aggg                             34

<210> SEQ ID NO 3
<211> LENGTH: 35
<212> TYPE: DNA
<213> ORGANISM: Homo sapiens

<400> SEQUENCE: 3
ctctcttttt caaccacgtg aaaatcaagc ttgct                            35

<210> SEQ ID NO 4
<211> LENGTH: 36
<212> TYPE: DNA
<213> ORGANISM: Homo sapiens

<400> SEQUENCE: 4
atctagatca cccaggagaa cgtcagcaga tctcta                           36

<210> SEQ ID NO 5
<211> LENGTH: 36
<212> TYPE: DNA
<213> ORGANISM: Homo sapiens

<400> SEQUENCE: 5
gagcagcaaa gacattatac cacaagagac aagcaa                           36

<210> SEQ ID NO 6
<211> LENGTH: 36
<212> TYPE: DNA
<213> ORGANISM: Homo sapiens

<400> SEQUENCE: 6
```

| | |
|---|---|
| tcggctcttt tgtgtcattt ttcattccct taacca | 36 |

<210> SEQ ID NO 7
<211> LENGTH: 36
<212> TYPE: DNA
<213> ORGANISM: Homo sapiens

<400> SEQUENCE: 7

| | |
|---|---|
| ctcaacgcct aacatggttg actgtgtcta cagttt | 36 |

<210> SEQ ID NO 8
<211> LENGTH: 36
<212> TYPE: DNA
<213> ORGANISM: Homo sapiens

<400> SEQUENCE: 8

| | |
|---|---|
| taactgacat tttcaatacc tccgatggtg gacgct | 36 |

<210> SEQ ID NO 9
<211> LENGTH: 36
<212> TYPE: DNA
<213> ORGANISM: Homo sapiens

<400> SEQUENCE: 9

| | |
|---|---|
| gggagttcag catggaaagc agtaactact atgcag | 36 |

<210> SEQ ID NO 10
<211> LENGTH: 36
<212> TYPE: DNA
<213> ORGANISM: Homo sapiens

<400> SEQUENCE: 10

| | |
|---|---|
| ttcaatctat cagcaactac ctccaaactc aggacc | 36 |

<210> SEQ ID NO 11
<211> LENGTH: 35
<212> TYPE: DNA
<213> ORGANISM: Homo sapiens

<400> SEQUENCE: 11

| | |
|---|---|
| caccattctt tgtcaccaat attgtggatc ctttc | 35 |

<210> SEQ ID NO 12
<211> LENGTH: 31
<212> TYPE: DNA
<213> ORGANISM: Homo sapiens

<400> SEQUENCE: 12

| | |
|---|---|
| cttttttggct ggggagagac gtactctgag g | 31 |

<210> SEQ ID NO 13
<211> LENGTH: 30
<212> TYPE: DNA
<213> ORGANISM: Homo sapiens

<400> SEQUENCE: 13

| | |
|---|---|
| atcctcaacc tctgcctcat cagcctggac | 30 |

<210> SEQ ID NO 14
<211> LENGTH: 36
<212> TYPE: DNA
<213> ORGANISM: Homo sapiens

<400> SEQUENCE: 14
tgaaaggaaa aacatctcca tctttaagcg agaaca                            36

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
taatacgact cactataggg                                              20

<210> SEQ ID NO 16
<211> LENGTH: 18
<212> TYPE: DNA
<213> ORGANISM: Artificial Sequence
<220> FEATURE:
<223> OTHER INFORMATION: PCR primer

<400> SEQUENCE: 16
tagaaggcac agtcgagg                                                18

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
cggtcaaaaa ggtggagaag                                              20

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
gaggcaagtg ctctttggag                                              20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
agtcctcctg cctgtgtagg                                              20

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
cgccgatgat aactttgtcc                                              20

<210> SEQ ID NO 21
<211> LENGTH: 20
<212> TYPE: DNA

-continued

```
<213> ORGANISM: Artificial Sequence
<220> FEATURE:
<223> OTHER INFORMATION: PCR primer

<400> SEQUENCE: 21
actggctgcc ttcttcacac                                               20

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
tgtcctttcg agaaccatcc                                               20

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
atggtgaacc tgaggaatgc                                               20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
ttccatgctt actgccatga                                               20

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
caatgagttc gtggatgtgg                                               20

<210> SEQ ID NO 26
<211> LENGTH: 20
<212> TYPE: DNA
<213> ORGANISM: Artificial Sequence
<220> FEATURE:
<223> OTHER INFORMATION: PCR primer

<400> SEQUENCE: 26
tgaccacata gaagaggggc                                               20

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
acaccgtctt cagggtcaac                                               20
```

```
<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
acaccgtctt cagggtcaac                                               20

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
gagaccaaag cagccaagac                                               20

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ttgtggttga acaagggaca                                               20
```